US012643906B2

(12) United States Patent
Mi et al.

(10) Patent No.: US 12,643,906 B2
(45) Date of Patent: Jun. 2, 2026

(54) FUSED AZA-HETEROCYCLIC AMIDE COMPOUND AND USE THEREOF

(71) Applicant: CSPC ZHONGQI PHARMACEUTICAL TECHNOLOGY (SHIJIAZHUANG) CO., LTD, Shijiazhuang (CN)

(72) Inventors: Guorui Mi, Shijiazhuang (CN); Yan Zhang, Shijiazhuang (CN); Chunhua Jiang, Shijiazhuang (CN); Yanxia Xu, Shijiazhuang (CN); Lixue Fan, Shijiazhuang (CN); Xuejiao Zhang, Shijiazhuang (CN); Yanan Qin, Shijiazhuang (CN)

(73) Assignee: CSPC ZHONGQI PHARMACEUTICAL TECHNOLOGY (SHIJIAZHUANG) CO., LTD, Shijiazhuang (CN)

( * ) Notice: Subject to any disclaimer, the term of this patent is extended or adjusted under 35 U.S.C. 154(b) by 757 days.

(21) Appl. No.: 17/998,827

(22) PCT Filed: May 14, 2021

(86) PCT No.: PCT/CN2021/093930
§ 371 (c)(1),
(2) Date: Nov. 15, 2022

(87) PCT Pub. No.: WO2021/228248
PCT Pub. Date: Nov. 18, 2021

(65) Prior Publication Data

US 2023/0227460 A1 Jul. 20, 2023

(30) Foreign Application Priority Data

May 15, 2020 (CN) ........................ 202010411386.0

(51) Int. Cl.
*C07D 487/14* (2006.01)
*A61P 35/00* (2006.01)
*C07D 519/00* (2006.01)

(52) U.S. Cl.
CPC ............ *C07D 487/14* (2013.01); *A61P 35/00* (2018.01); *C07D 519/00* (2013.01)

(58) Field of Classification Search
CPC ...... C07D 487/14; C07D 519/00; A61P 35/00
See application file for complete search history.

(56) References Cited

FOREIGN PATENT DOCUMENTS

| | | | | |
|---|---|---|---|---|
| CN | 104114553 A | | 10/2014 | |
| CN | 107652293 A | | 2/2018 | |
| CN | 111039946 | * | 10/2018 | ........... C07D 498/22 |
| CN | 108794484 A | | 11/2018 | |
| CN | 111039946 A | | 4/2020 | |
| WO | 2012034095 A1 | | 3/2012 | |
| WO | 2013088257 A1 | | 6/2013 | |
| WO | 2019029629 A1 | | 2/2019 | |

OTHER PUBLICATIONS

Bernard-Gauthier, Vadim et al., "A Kinome-Wide Selective Radiolabeled TrkB/C Inhibitor for in Vitro and in Vivo Neuroimaging: Synthesis, Preclinical Evaluation, and First-in-Human", Journal of Medicinal Chemistry, vol. 60, No. 16, Jul. 11, 2017, pp. 6897-6910.
Cross, L. C. et al.; "Rules for the Nomenclature of Organic Chemistry, Section E: Stereochemistry"; International Union of Pure and Applied Chemistry(IUPAC) 1974 Recommendations for Section E, "Fundamental Stereochemistry"; Pure & Appl.Chem.; vol. 45, No. 1-B; Year: 1976; pp. 11-30.
Brickner, Steven J. et al.; "Synthesis and Antibacterial Activity of U-100592 and U-100766, Two Oxazolidinone Antibacterial Agents for the Potential Treatment of Multidrug-Resistant Gram-Positive Bacterial Infections"; J. Med. Chem.; vol. 39, No. 3; Year: 1996; pp. 673-679.
Mallesham, B. et al.; "Highly Efficient Cul-Catalyzed Coupling of Aryl Bromides with Oxazolidinones Using Buchwald's Protocol: A Short Route to Linezolid and Toloxatone"; Organic Letters; vol. 5, No. 7; Year: 2003; pp. 963-965.
Blake, Martin I. et al.; "Studies with Deuterated Drugs"; Journal of Pharmaceutical Sciences; vol. 64, No. 3; Mar. 1975; pp. 367-391.
Kushner, D. J. et al.; "Pharmacological uses and perspectives of heavy water and deuterated compounds"; Can. J. Physiol. Pharmacol.; vol. 77; year: 1999; pp. 79-88.
Kato, Shiro et al.; "Synthesis of Deuterated Mosapride Citrate"; Journal of Labelled Compounds and Radiopharmaceuticals; vol. 36, No. 10; Year: 1995; pp. 927-932.

* cited by examiner

*Primary Examiner* — Erich A Leeser
(74) *Attorney, Agent, or Firm* — NKL Law; Allen Xue

(57) ABSTRACT

A compound of formula (I) or a tautomer, a stereoisomer, a solvate, a nitrogen oxide, a prodrug, an isotope derivative or a pharmaceutically acceptable salt thereof exhibit kinase inhibitory activity against a variety of kinases (such as TRK, ALK and ROS1) and mutants thereof, in particular TRK and a mutant form thereof. An in vitro cell inhibitory activity test and an in vivo anti-tumor model test show that the compounds have a strong inhibitory effect on a variety of cells containing TRK mutations and tumors, have a good safety, and have a good clinical value as drugs.

(I)

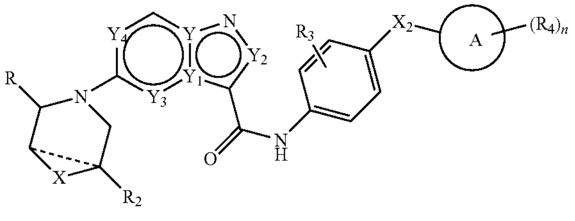

20 Claims, 1 Drawing Sheet

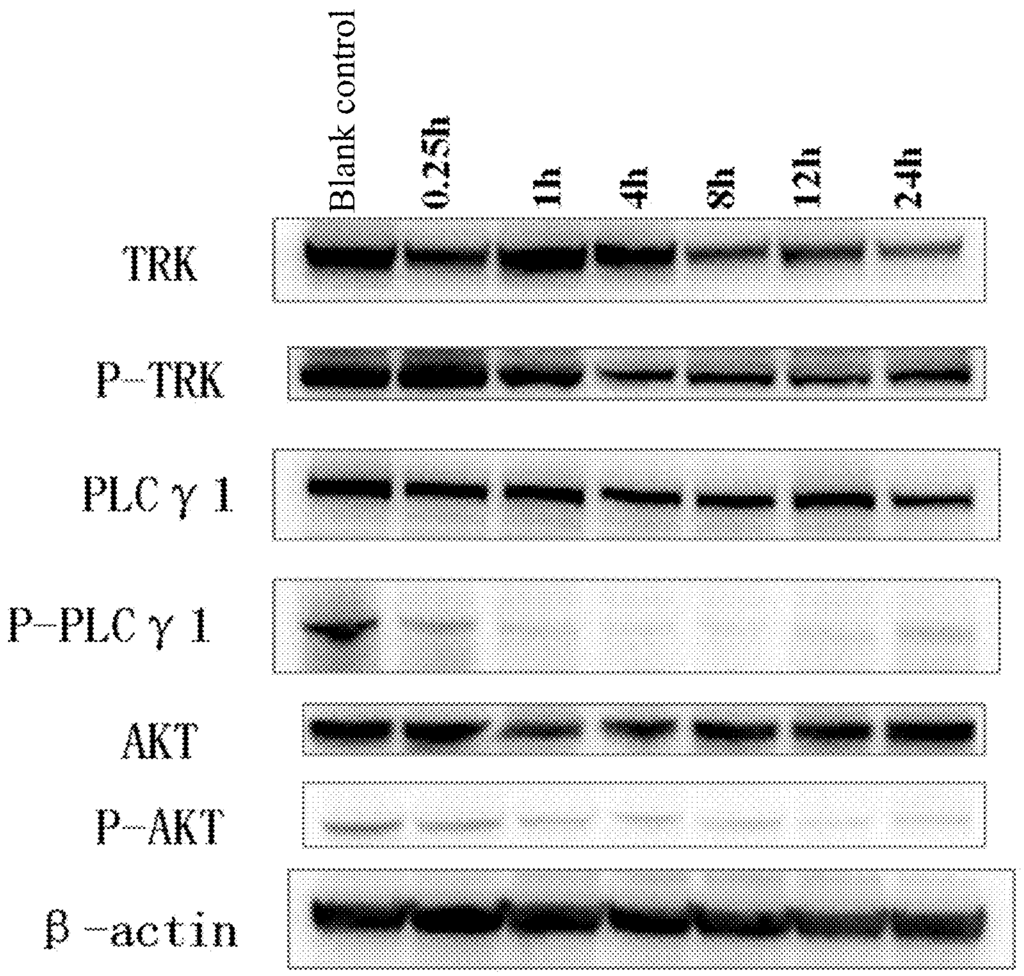
Blank control
0.25h
1h
4h
8h
12h
24h
TRK
P-TRK
PLCγ1
P-PLCγ1
AKT
P-AKT
β-actin

FUSED AZA-HETEROCYCLIC AMIDE COMPOUND AND USE THEREOF

CROSS-REFERENCE TO RELATED APPLICATIONS

This application is a U.S. national stage entry of PCT International Application No. PCT/CN2021/093930, filed on May 14, 2021, which claims priority to Chinese Patent Application No. 202010411386.0 filed on May 15, 2020 and entitled "PYRAZOLOPYRIMIDINE AMIDE COMPOUND AND USE THEREOF", the content of which is incorporated herein by reference in its entirety.

TECHNICAL FIELD

The present disclosure belongs to the technical field of pharmaceuticals, and particularly relates to a fused aza-heterocyclic amide compound with kinase inhibitory activity, or a tautomer, a stereoisomer, an optical isomer, a solvate, an isotopic derivative, a nitrogen oxide, a prodrug or a pharmaceutically acceptable salt thereof, and a pharmaceutical composition containing the same, and use thereof as a medicament for preventing and/or treating TRK-mediated diseases.

BACKGROUND

Tropomyosin-related kinase or tropomyosin receptor kinase (TRK) is a type of nerve growth factor receptor, the family of which consists of three highly homologous subtypes TRKA, TRKB and TRKC, encoded by neurotrophic tyrosine receptor kinase type 1 (NTRK 1), NTRK2 and NTRK3 genes, respectively. When a TRK receptor protein binds to a corresponding ligand, different physiological functions can be achieved by the activation of downstream signaling pathways, such as RAS/MAPK pathway, PLC γ pathway, and PI3K pathway. The TRK family proteins are normally mainly expressed in nerve tissues, are involved in differentiation and survival of nerve cells and formation of axons and dendrites, and play an important role in embryonic development and maintenance of normal functions of the nervous system.

TRK kinase is activated in malignancies by a variety of mechanisms, mainly structural rearrangements and changed expression. For example, the gene NTRK coding TRK kinase is rearranged with other genes to generate a fusion oncogene, which causes the TRK kinase to be changed in structure and expression and no longer regulated and controlled by nerve growth factor ligand, namely constitutively activated, and hence promotes tumorigenesis and development. In addition, the gene sequencing result also shows that the TRK kinase has close relation with the occurrence, metastasis and deterioration of various tumors, and is expressed in various tumors, such as non-small cell lung cancer, colorectal cancer, melanoma, gall bladder cancer, thyroid cancer, malignant glioma, and the like.

Currently, the first generation of TRK inhibitor Larotrectinib (LOXO-101) and Entrectinib (RXDX-101) were approved by the U.S. Food and Drug Administration (FDA) in 2018 and 2019, respectively. Larotrectinib is a potent, oral, and selective inhibitor of tropomyosin receptor kinase, with efficacy data published at the ASCO (the American Society of Clinical Oncology) meeting as early as June, 2017. In a total of 55 subjects enrolled in phase I and phase II clinical trials, of which 46 evaluable patients had an Overall Response Rate (ORR) of 78%. Entrecteinib is a potent inhibitor of TRK, ROS1 and ALK proteins and can pass through the blood-brain barrier, with an ORR of 79% in 24 evaluable patients in phase I clinical trials.

Like other targeted drugs, TRK inhibitors also face drug-resistance problems. Mutation in NTRK kinase domain can cause change in conformation of TRK family protein kinase domain or in binding affinity for ATP, thereby affecting the binding of TRK inhibitors to targets, and the mutation types are G595R, G639R, G667C, and the like. In order to solve the drug-resistance problem of the first generation of TRK inhibitors, the second generation of TRK inhibitors have been studied, such as LOXO-195, TPX-005, and the like.

LOXO-101

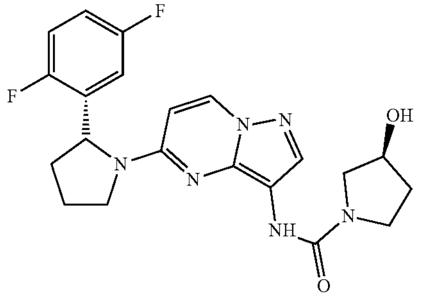

RXDX-101

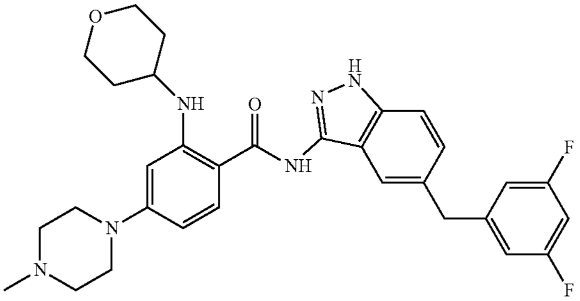

LOXO-195

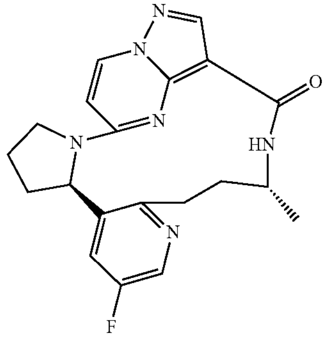

TPX-0005

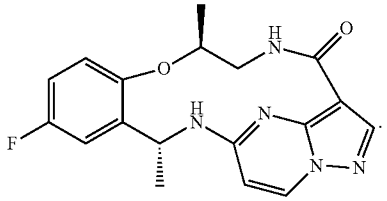

SUMMARY

One aspect of the present disclosure is to provide a type of fused aza-heterocyclic amide compound with excellent TRK (wild-type and mutant-type) inhibition activity and a novel structure, or a tautomer, a stereoisomer, a solvate, an isotopic derivative, a nitrogen oxide, a prodrug or a pharmaceutically acceptable salt thereof.

Another aspect of the present disclosure is to provide a type of fused aza-heterocyclic amide compound with better TRK mutant tumor cell inhibition activity compared with the known compound and a novel structure, or a tautomer, a stereoisomer, a solvate, an isotopic derivative, a nitrogen oxide, a prodrug or a pharmaceutically acceptable salt thereof.

Another aspect of the present disclosure is to provide a type of fused aza-heterocyclic amide compound with better TRK (wild-type and mutant-type) inhibition activity and TRK mutant tumor cell inhibition activity compared with the known compound and a novel structure, or a tautomer, a stereoisomer, a solvate, an isotopic derivative, a nitrogen oxide, a prodrug or a pharmaceutically acceptable salt thereof.

Another aspect of the present disclosure is to provide a type of fused aza-heterocyclic amide compound with better TRK mutation tumor cell inhibitory activity and in vivo anti-tumor activity compared with the known compound, or a tautomer, a stereoisomer, a solvate, an isotopic derivative, a nitrogen oxide, a prodrug or a pharmaceutically acceptable salt thereof.

Another aspect of the present disclosure is to provide a type of fused aza-heterocyclic amide compound with better TRK mutation tumor cell inhibitory activity and in vivo anti-tumor activity as well as better safety compared with the known compound, or a tautomer, a stereoisomer, a solvate, an isotopic derivative, a nitrogen oxide, a prodrug or a pharmaceutically acceptable salt thereof.

Another aspect of the present disclosure is to provide a type of fused aza-heterocyclic amide compound with better TRK (wild-type and mutant-type) inhibition activity, TRK mutant tumor cell inhibition activity and in vivo anti-tumor activity as well as better safety compared with the known compound, or a tautomer, a stereoisomer, a solvate, an isotopic derivative, a nitrogen oxide, a prodrug or a pharmaceutically acceptable salt thereof.

Specifically, the present disclosure provides a compound of formula (I) or a tautomer, a stereoisomer, an optical isomer, a solvate, an isotopic derivative, a nitrogen oxide, a prodrug or a pharmaceutically acceptable salt thereof, (I)

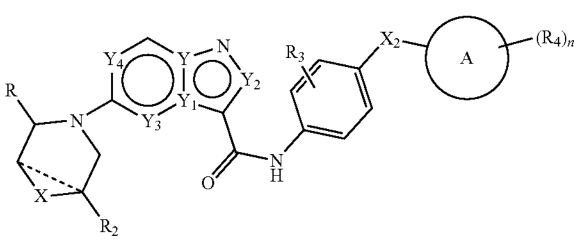

wherein, X is selected from: a bond, —O—, —S—, —NH—, and —$CH_2$—;

Y, $Y_1$, $Y_2$, $Y_3$, and $Y_4$ are each independently selected from: —CH—, N, and C;

$X_2$ is selected from: a bond, —$(CH_2)_p$—, and —NH—, wherein p is 1, 2, 3 or 4;

------ represents that the bond is absent or is present;

R is selected from: $C_{5-12}$ aryl or heteroaryl, wherein each aryl or heteroaryl is unsubstituted or substituted with at least one substituent selected from $R_1$;

$R_1$, when present, is each independently selected from: hydrogen, halogen, —OH, amino, —$NHC_{1-6}$ alkyl, —$N(C_{1-6}$ alkyl$)_2$, cyano, $C_{1-6}$ alkyl unsubstituted or substituted with at least one $R_{1a}$, $C_{1-6}$ alkoxy unsubstituted or substituted with at least one $R_{1a}$, $C_{3-6}$ cycloalkyl unsubstituted or substituted with at least one $R_{1a}$, $C_{3-6}$ cycloalkoxy unsubstituted or substituted with at least one $R_{1a}$, and —$SC_{1-6}$ alkyl;

$R_{1a}$, when present, is each independently selected from: $C_{1-6}$ alkyl, $C_{1-6}$ alkoxy, nitro, halogen, —OH, amino, —$NHC_{1-6}$ alkyl, —$N(C_{1-6}$ alkyl$)_2$, and cyano;

$R_2$ is selected from: H, halogen, hydroxyl, amino, and substituted or unsubstituted $C_{1-6}$ alkyl, wherein "substituted" means substituted with 1, 2 or 3 substituent(s) selected from halogen and hydroxyl; $R_3$ is selected from: H, halogen, —OH, amino, $C_{1-6}$ alkyl, and $C_{1-6}$ alkoxy;

ring A is selected from: cycloalkyl, heterocycloalkyl, bridged cyclyl, heterobridged cyclyl, fused cyclyl, heterofused cyclyl, spiro cyclyl, and heterospiro cyclyl, wherein heteroatoms in the heterocycloalkyl, the heterobridged cyclyl, the heterofused cyclyl, and the heterospiro cyclyl are independently selected from O, S, and N, and the number of the heteroatoms is selected from 1, 2, 3, and 4;

$R_4$ is at any substitutable position on ring A and is independently selected from: —H, —OH, halogen, —CN, oxo, substituted or unsubstituted $C_{1-6}$ alkyl, —$(CH_2)_m$—OH, —$(CH_2)_m$—COOH, —$(CH_2)_m$—CO—$NH_2$, —CO—$(CH_2)_m$—$NH_2$, —CO—$CR_{4a}R_{4b}$—OH, and —CO—$R_{4b}$; wherein, the oxo means that two H of the same substitution site are substituted with the same O to form a double bond; m is selected from 1, 2, 3, and 4;

$R_{4a}$ is selected from hydrogen and unsubstituted or substituted $C_{1-4}$ alkyl;

$R_{4b}$ is selected from H, unsubstituted or substituted $C_{1-6}$ alkyl, and unsubstituted or substituted $C_{3-6}$ cycloalkyl, a substituent for the substitution is independently selected from —OH, —$NH_2$, and halogen, and the number of the substituents is selected from 1, 2, and 3;

n is selected from 1, 2, 3, and 4.

In one embodiment, the present disclosure provides a compound of formula (I), or a tautomer, a stereoisomer, an optical isomer, a solvate, an isotopic derivative, a nitrogen oxide, a prodrug or a pharmaceutically acceptable salt thereof, wherein R is selected from: $C_{5-9}$ aryl and heteroaryl, wherein each aryl or heteroaryl is unsubstituted or substituted with at least one substituent selected from $R_1$; or, R is selected from: $C_{5-6}$ aryl and heteroaryl, wherein each aryl or heteroaryl is unsubstituted or substituted with at least one substituent selected from $R_1$.

In one embodiment, the compound has a structure of formula (I-1) or formula (I-2):

(I-1)

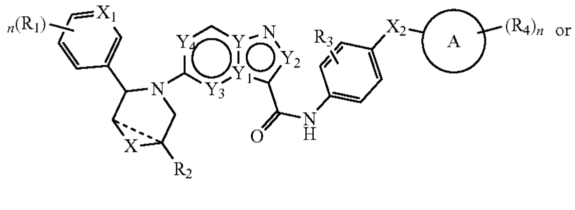

or

-continued (I-2)

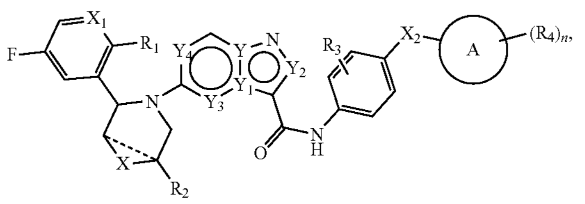

wherein, $R_1$, $R_2$, $R_3$, $R_4$, X, $X_2$, Y, $Y_1$, $Y_2$, $Y_3$, $Y_4$, ring A and n are as described for the compound of formula (I) of the present disclosure, and $X_1$ is selected from: —CH— and N.

In one embodiment, the compound has a structure of formula (I-A):

(I-A)

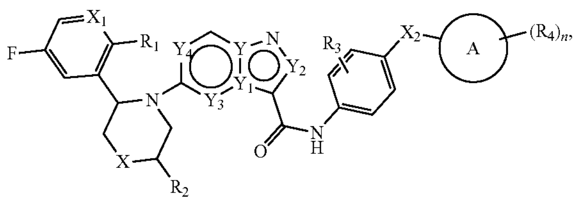

wherein, $R_1$, $R_2$, $R_3$, $R_4$, X, $X_1$, $X_2$, Y, $Y_1$, $Y_2$, $Y_3$, $Y_4$, ring A and n are as described for the compound of formula (I-1) or formula (I-2) of the present disclosure.

In one embodiment, the compound has a structure of formula (I-A-1a), formula (I-A-1b), or formula (I-A-1c):

(I-A-1a)

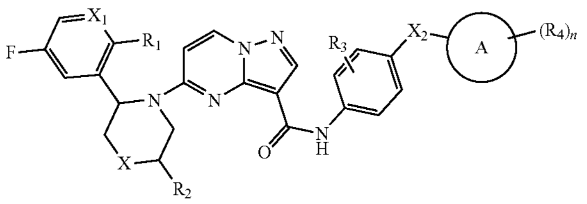

(I-A-1b)

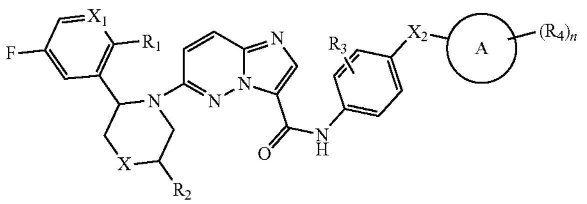

(I-A-1c)

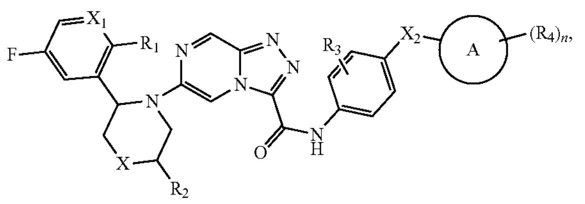

wherein, $R_1$, $R_2$, $R_3$, $R_4$, X, $X_1$, $X_2$, ring A and n are as described for the compound of formula (I-1) or formula (I-2) of the present disclosure.

In one embodiment, the compound has a structure of formula (I-B):

(I-B)

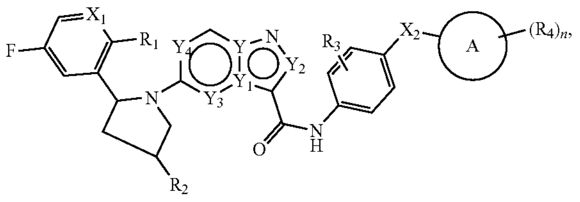

wherein, $R_1$, $R_2$, $R_3$, $R_4$, $X_1$, $X_2$, Y, $Y_1$, $Y_2$, $Y_3$, $Y_4$, ring A and n are as described for the compound of formula (I-1) or formula (I-2) of the present disclosure.

In one embodiment, the compound has a structure of formula (I-B-1a), formula (I-B-1b), or formula (I-B-1c):

(I-B-1a)

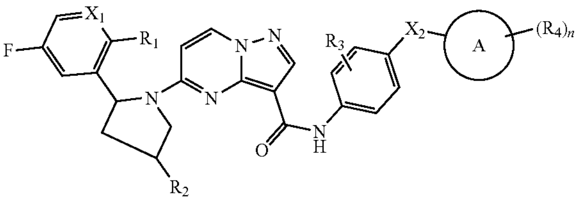

(I-B-1b)

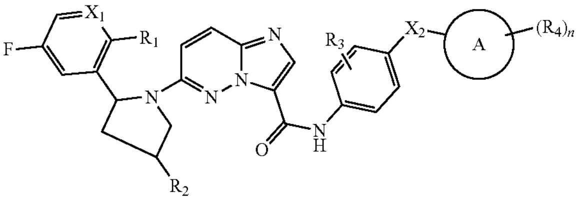

(I-B-1c)

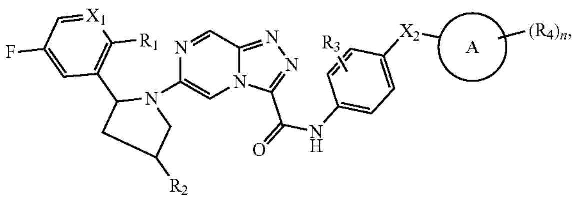

wherein, $R_1$, $R_2$, $R_3$, $R_4$, $X_1$, $X_2$, ring A and n are as described for the compound of formula (I-1) or formula (I-2) of the present disclosure.

In one embodiment, the compound has a structure of formula (I-C):

(I-C)

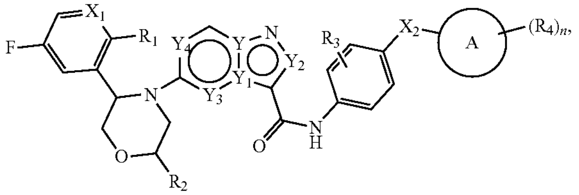

wherein, $R_1$, $R_2$, $R_3$, $R_4$, $X_1$, $X_2$, Y, $Y_1$, $Y_2$, $Y_3$, $Y_4$, ring A and n are as described for the compound of formula (I-1) or formula (I-2) of the present disclosure.

In one embodiment, the compound has a structure of formula (I-C-1a), formula (I-C-1b), or formula (I-C-1c):

(I-C-1a)

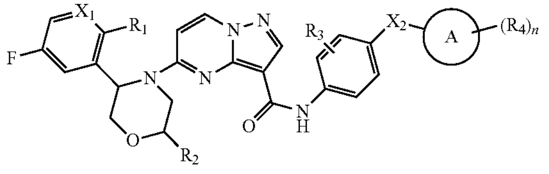

(I-C-1b)

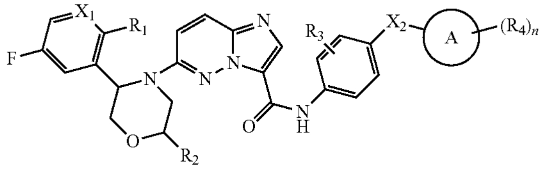

(I-C-1c)

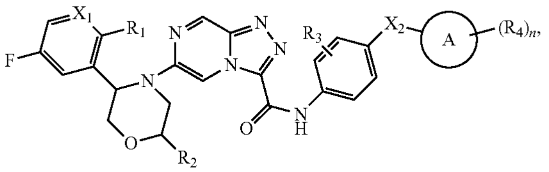

wherein, $R_1$, $R_2$, $R_3$, $R_4$, $X_1$, $X_2$, ring A and n are as described for the compound of formula (I-1) or formula (I-2) of the present disclosure.

In one embodiment, the present disclosure provides a compound (a compound of formula (I), a compound of formula (I-1), a compound of formula (I-2), a compound of formula (I-A), a compound of formula (I-A-1a), a compound of formula (I-A-1b), a compound of formula (I-A-1c), a compound of formula (I-B), a compound of formula (I-B-1a), a compound of formula (I-B-1b), a compound of formula (I-B-1c), a compound of formula (I-C), a compound of formula (I-C-1a), a compound of formula (I-C-1b), a compound of formula (I-C-1c)), or a tautomer, a stereoisomer, an optical isomer, a solvate, an isotopic derivative, a nitrogen oxide, a prodrug or a pharmaceutically acceptable salt thereof, wherein, $R_1$, when present, is each independently selected from: hydrogen, halogen, —OH, amino, cyano, $C_{1-6}$ alkyl unsubstituted or substituted with at least one $R_{1a}$, $C_{1-6}$ alkoxy unsubstituted or substituted with at least one $R_{1a}$, $C_{3-6}$ cycloalkyl unsubstituted or substituted with at least one $R_{1a}$, and $C_{3-6}$ cycloalkoxy unsubstituted or substituted with at least one $R_{1a}$; or, $R_1$, when present, is each independently selected from: hydrogen, halogen, —OH, amino, cyano, $C_{1-6}$ alkyl unsubstituted or substituted with at least one $R_{1a}$, and $C_{1-6}$ alkoxy unsubstituted or substituted with at least one $R_{1a}$; or, $R_1$, when present, is each independently selected from: hydrogen, halogen, —OH, amino, $C_{1-6}$ alkyl, and $C_{1-6}$ alkoxy; or, $R_1$, when present, is each independently selected from: hydrogen, halogen, —OH, amino, $C_{1-3}$ alkyl, and $C_{1-3}$ alkoxy; or, $R_1$, when present, is each independently selected from: hydrogen, halogen, —OH, amino, methyl, ethyl, methoxy, and ethoxy; or, $R_1$, when present, is each independently selected from: hydrogen, F, $C_1$, —OH, methyl, and methoxy; or, $R_1$, when present, is each independently selected from: F. —OH, methyl, and methoxy.

In one embodiment, $R_{1a}$, when present, is each independently selected from: $C_{1-3}$ alkyl, $C_{1-3}$ alkoxy, nitro, halogen, —OH, amino, —NH$C_{1-6}$ alkyl, —N($C_{1-6}$ alkyl)$_2$, and cyano; or, $R_{1a}$ is selected from: halogen, —OH, amino, —NH$C_{1-3}$ alkyl, —N($C_{1-3}$ alkyl)$_2$, and cyano; or, $R_{1a}$ is selected from: halogen, —OH, amino, and cyano; or, $R_{1a}$ is selected from: F, $C_1$, and —OH.

In one embodiment, the present disclosure provides a compound (a compound of formula (I), a compound of formula (I-1), a compound of formula (I-2), a compound of formula (I-A), a compound of formula (I-A-1a), a compound of formula (I-A-1b), a compound of formula (I-A-1c), a compound of formula (I-B), a compound of formula (I-B-1a), a compound of formula (I-B-1b), a compound of formula (I-B-1c), a compound of formula (I-C), a compound of formula (I-C-1a), a compound of formula (I-C-1b), a compound of formula (I-C-1c)), or a tautomer, a stereoisomer, an optical isomer, a solvate, an isotopic derivative, a nitrogen oxide, a prodrug or a pharmaceutically acceptable salt thereof, wherein, $R_2$ is selected from: H, F, OH, and substituted or unsubstituted $C_{1-6}$ alkyl, wherein "substituted" means substituted with 1, 2 or 3 substituents selected from halogen and hydroxyl; or, $R_2$ is selected from H, F, —OH, and $C_{1-6}$ alkyl; or, $R_2$ is selected from H, F, —OH, and $C_{1-3}$ alkyl; or, $R_2$ is selected from H and F.

In one embodiment, the present disclosure provides a compound (a compound of formula (I), a compound of formula (I-1), a compound of formula (I-2), a compound of formula (I-A), a compound of formula (I-A-1a), a compound of formula (I-A-1b), a compound of formula (I-A-1c), a compound of formula (I-B), a compound of formula (I-B-1a), a compound of formula (I-B-1b), a compound of formula (I-B-1c), a compound of formula (I-C), a compound of formula (I-C-1a), a compound of formula (I-C-1b), a compound of formula (I-C-1c)), or a tautomer, a stereoisomer, an optical isomer, a solvate, an isotopic derivative, a nitrogen oxide, a prodrug or a pharmaceutically acceptable salt thereof, wherein, $X_1$ is selected from —CH— and N, and $R_1$ is selected from F and —$OCH_3$.

In one embodiment, $X_1$ is selected from —CH—, and $R_1$ is selected from F; or, $X_1$ is selected from N, and $R_1$ is selected from —$OCH_3$.

In one embodiment, the compound has a structure of formula (I-D):

(I-D)

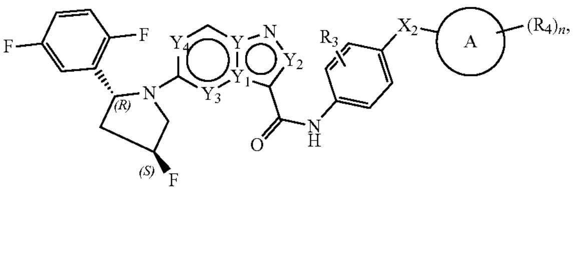

wherein, $R_3$, $R_4$, $X_2$, Y, $Y_1$, $Y_2$, $Y_3$, $Y_4$, ring A and n are as described for the compound of formula (I) of the present disclosure.

In one embodiment, the compound has a structure of formula (I-D-a), formula (I-D-b), or formula (I-D-c):

(I-D-a)

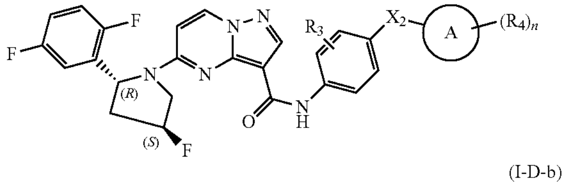

(I-D-b)

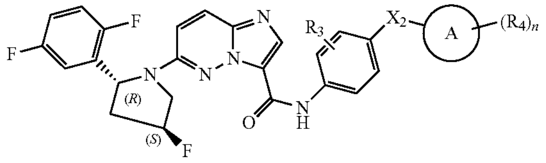

(I-D-c)

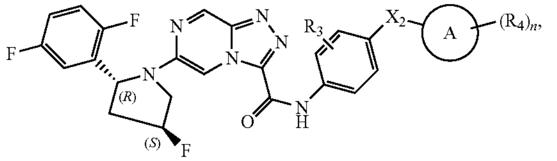

wherein, $R_3$, $R_4$, $X_2$, ring A and n are as described for the compound of formula (I) of the present disclosure.

In one embodiment, the present disclosure provides a compound (a compound of formula (I), a compound of formula (I-1), a compound of formula (I-2), a compound of formula (I-A), a compound of formula (I-A-1a), a compound of formula (I-A-1b), a compound of formula (I-A-1c), a compound of formula (I-B), a compound of formula (I-B-1a), a compound of formula (I-B-1b), a compound of formula (I-B-1c), a compound of formula (I-C), a compound of formula (I-C-1a), a compound of formula (I-C-1b), a compound of formula (I-C-1c), a compound of formula (I-D), a compound of formula (I-D-a), a compound of formula (I-D-b), a compound of formula (I-D-c)), or a tautomer, a stereoisomer, an optical isomer, a solvate, an isotopic derivative, a nitrogen oxide, a prodrug or a pharmaceutically acceptable salt thereof, wherein, $R_3$ is selected from: H, halogen, —OH, amino, $C_{1-3}$ alkyl, and $C_{1-3}$ alkoxy; or, $R_3$ is selected from: H, F, $C_1$, —OH, methyl, and methoxy; or, $R_3$ is selected from: H and F.

In one embodiment, the compound has a structure of formula (I-D-1a), formula (I-D-1b), or formula (I-D-1c):

(I-D-1a)

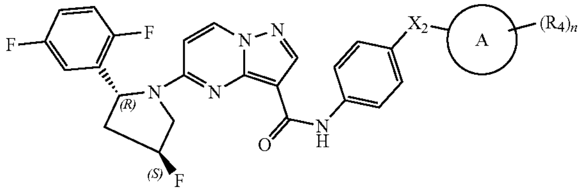

-continued (I-D-1b)

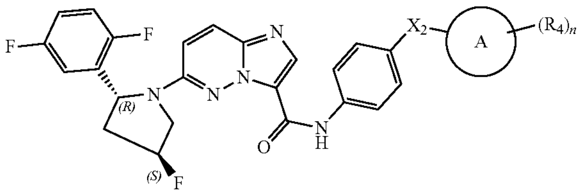

(I-D-1c)

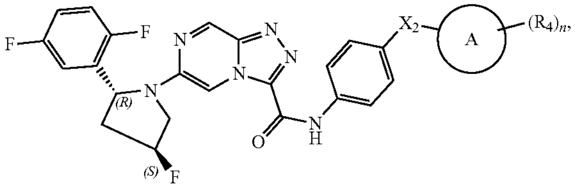

wherein, $R_4$, $X_2$, ring A and n are as described for the compound of formula (I) of the present disclosure.

In one embodiment, the compound has a structure of formula (I-C-1a-1):

(I-C-1a-1)

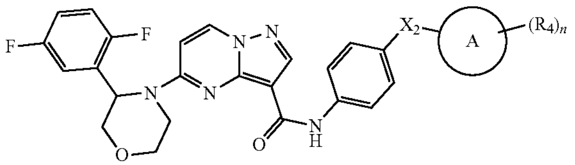

wherein, $R_4$, $X_2$, ring A and n are as described for the compound of formula (I) of the present disclosure.

In one embodiment, the compound has a structure of formula (I-C-1a-2):

(I-C-1a-2)

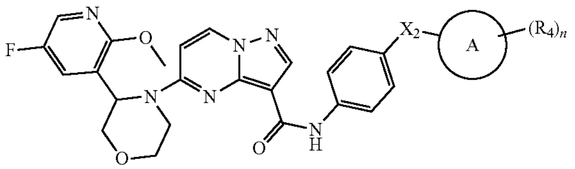

wherein, $R_4$, $X_2$, ring A and n are as described for the compound of formula (I) of the present disclosure.

In one embodiment, the present disclosure provides a compound (a compound of formula (I), a compound of formula (I-1), a compound of formula (I-2), a compound of formula (I-A), a compound of formula (I-A-1a), a compound of formula (I-A-1b), a compound of formula (I-A-1c), a compound of formula (I-B), a compound of formula (I-B-1a), a compound of formula (I-B-1b), a compound of formula (I-B-1c), a compound of formula (I-C), a compound of formula (I-C-1a), a compound of formula (I-C-1b), a compound of formula (I-C-1c), a compound of formula (I-D), a compound of formula (I-D-a), a compound of formula (I-D-b), a compound of formula (I-D-c), a compound of formula (I-D-1a), a compound of formula (I-D-1b), a compound of formula (I-D-1c), a compound of formula (I-C-1a-1), a compound of formula (I-C-1a-2), the same below), or a tautomer, a stereoisomer, an optical isomer, a solvate, an isotopic derivative, a nitrogen oxide, a prodrug or a pharmaceutically acceptable salt thereof, wherein, ring A is selected from: $C_{3-6}$ cycloalkyl, 4-6 membered heterocycloalkyl, $C_{6-8}$ bridged cyclyl, 6-8 membered heterobridged cyclyl, $C_{8-10}$ fused cyclyl, 8-10 membered heterofused cyclyl, $C_{7-12}$ monospiro cyclyl, and 7-12 membered heteromonospiro cyclyl; or, ring A is selected from: 4-6 membered heterocycloalkyl, 6-8 membered heterobridged cyclyl, 8-10 membered heterofused cyclyl, and 7-12 membered heteromonospiro cyclyl; wherein heteroatoms in the heterocycloalkyl, the heterobridged cyclyl, the heterofused cyclyl and the heteromonospiro cyclyl are independently selected from O, S, and N, and the number of the heteroatoms is selected from 1, 2, 3, and 4; or, ring A is selected from the following structures:

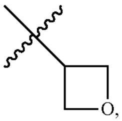, 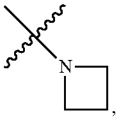, 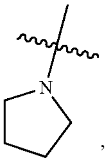, 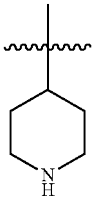, 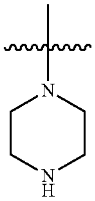, 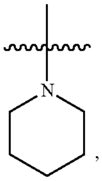, 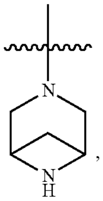, 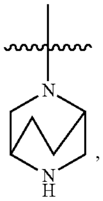, 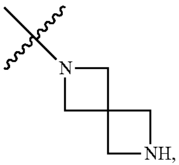, 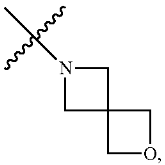, 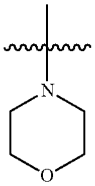, 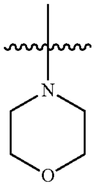, 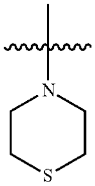, 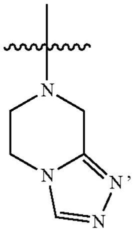, and 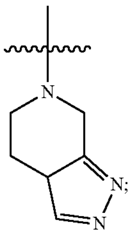;

or, ring A is selected from the following structures:

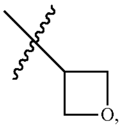, 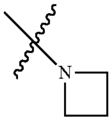, 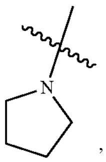, 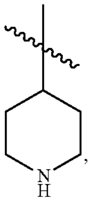, 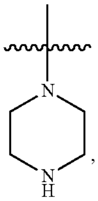, 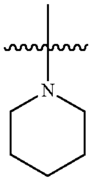, 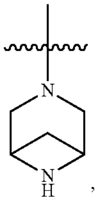, 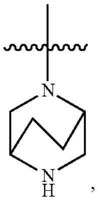, and 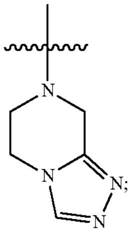;

or, ring A is selected from the following structures:

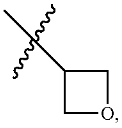, 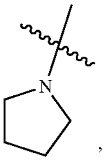, 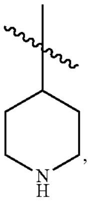, 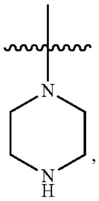, 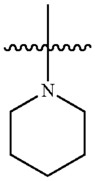, and 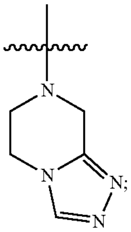;

or, ring A is selected from the following structures:

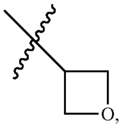, 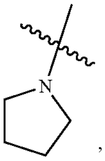, 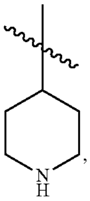, 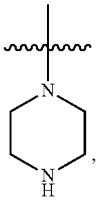, and 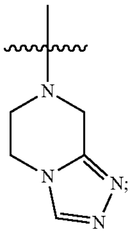;

or, ring A is selected from the following structures:

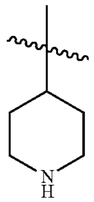
and
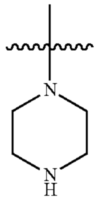
.

In one embodiment, the present disclosure provides a compound (a compound of formula (I), a compound of formula (I-1), a compound of formula (I-2), a compound of formula (I-A), a compound of formula (I-A-1a), a compound of formula (I-A-1b), a compound of formula (I-A-1c), a compound of formula (I-B), a compound of formula (I-B-1a), a compound of formula (I-B-1b), a compound of formula (I-B-1c), a compound of formula (I-C), a compound of formula (I-C-1a), a compound of formula (I-C-1b), a compound of formula (I-C-1c), a compound of formula (I-D), a compound of formula (I-D-a), a compound of formula (I-D-b), a compound of formula (I-D-c), a compound of formula (I-D-1a), a compound of formula (I-D-1b), a compound of formula (I-D-1c), a compound of formula (I-C-1a-1), and a compound of formula (I-C-1a-2)), or a tautomer, a stereoisomer, an optical isomer, a solvate, an isotopic derivative, a nitrogen oxide, a prodrug or a pharmaceutically acceptable salt thereof, wherein, $R_4$ is independently selected from: —H, —OH, halogen, —CN, oxo, substituted or unsubstituted $C_{1-6}$ alkyl, —COOH, —$CONH_2$, —CO—$CR_{4a}R_{4b}$—OH, and —CO—$R_{4b}$; or, $R_4$ is independently selected from: —H, —OH, halogen, —CN, oxo, substituted or unsubstituted $C_{1-6}$ alkyl, —CO—$CR_{4a}R_{4b}$—OH, and —CO—$R_{4b}$; or, $R_4$ is independently selected from: —H, —OH, halogen, substituted or unsubstituted $C_{1-6}$ alkyl, —CO—$CR_{4a}R_{4b}$—OH, and —CO—$R_{4b}$; or, $R_4$ is independently selected from: —H, —OH, halogen, substituted or unsubstituted $C_{1-3}$ alkyl, —CO—$CR_{4a}R_{4b}$—OH, and —CO—$R_{4b}$; or, $R_4$ is independently selected from: —H, —OH, substituted or unsubstituted $C_{1-3}$ alkyl, —CO—$CR_{4a}R_{4b}$—OH, and —CO—$R_{4b}$; or, $R_4$ is independently selected from: —CO—$CR_{4a}R_{4b}$—OH and —CO—$R_{4b}$; wherein, the oxo means that two H of the same substitution site are substituted with the same O to form a double bond; $R_{4a}$ is selected from hydrogen and unsubstituted or substituted $C_{1-4}$ alkyl; $R_{4b}$ is selected from unsubstituted or substituted $C_{1-6}$ alkyl and unsubstituted or substituted $C_{3-6}$ cycloalkyl, a substituent for the substitution is independently selected from —OH, —$NH_2$, and halogen, and the number of the substituents is selected from 1, 2, and 3; or, the substituent for the substitution are independently selected from —OH and F, and the number of substituents is selected from 1, 2, and 3.

In one embodiment, the present disclosure provides a compound, or (and) a tautomer, an optical isomer, a solvate, an isotopic derivative or a pharmaceutically acceptable salt thereof, wherein the compound has a structure of formula (I-A-1a):

(I-A-1a)

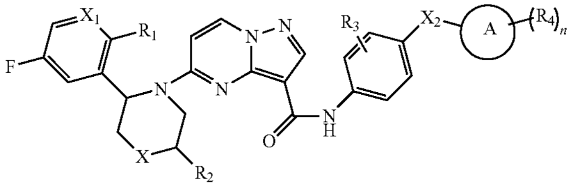

wherein, X is selected from: a bond, —O—, —S—, —NH—, and —$CH_2$—;

$X_1$ is selected from: —CH— and N;

$X_2$ is selected from: a bond, —$(CH_2)_p$—, and —NH—, wherein p is 1, 2, 3 or 4;

$R_1$ is selected from: H, halogen, —OH, amino, $C_{1-6}$ alkyl, and $C_{1-6}$ alkoxy;

$R_2$ is selected from: H, F, OH, and substituted or unsubstituted $C_{1-6}$ alkyl, wherein “substituted” means substituted with 1, 2 or 3 substituents selected from halogen and hydroxyl;

$R_3$ is selected from: H, halogen, —OH, amino, $C_{1-6}$ alkyl, and $C_{1-6}$ alkoxy;

ring A is selected from: cycloalkyl, heterocycloalkyl, bridged cyclyl, heterobridged cyclyl, fused cyclyl, heterofused cyclyl, spiro cyclyl, and heterospiro cyclyl, wherein heteroatoms in the heterocycloalkyl, the heterobridged cyclyl, the heterofused cyclyl, and the heterospiro cyclyl are independently selected from O, S, and N, and the number of the heteroatoms is selected from 1, 2, 3, and 4;

$R_4$ is at any substitutable position on ring A and is independently selected from: —H, —OH, halogen, —CN, oxo, substituted or unsubstituted $C_{1-6}$ alkyl, —$(CH_2)_m$—OH, —$(CH_2)_m$—COOH, —$(CH_2)_m$—CO—$NH_2$, —CO—$(CH_2)_m$—$NH_2$, —CO—$CR_{4a}R_{4b}$—OH, and —CO—$R_{4b}$; wherein, the oxo means that two H of the same substitution site are substituted with the same O to form a double bond; m is selected from 1, 2, 3, and 4; $R_{4a}$ is selected from hydrogen and unsubstituted or substituted $C_{1-4}$ alkyl; $R_{4b}$ is selected from H, unsubstituted or substituted $C_{1-6}$ alkyl, and unsubstituted or substituted $C_{3-6}$ cycloalkyl, a substituent for the substitution is independently selected from —OH, —$NH_2$, and halogen, and the number of the substituents is selected from 1, 2, and 3;

n is selected from 1, 2, 3, and 4.

In one embodiment, the present disclosure provides a compound, or a tautomer, an optical isomer, a solvate, an isotopic derivative or a pharmaceutically acceptable salt thereof, wherein the compound has a structure of formula (I-B-1a):

(I-B-1a)

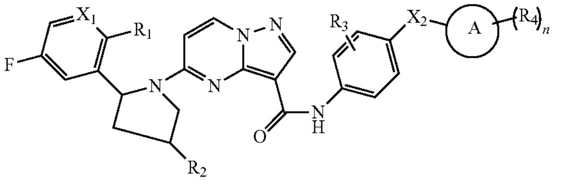

wherein, $R_1$, $R_2$, $R_3$, $R_4$, $X_1$, $X_2$, ring A and n are as described for the compound of formula (I-A-1a) of the present disclosure.

In one embodiment, the present disclosure provides a compound, or a tautomer, an optical isomer, a solvate, an isotopic derivative or a pharmaceutically acceptable salt thereof, wherein the compound has a structure of formula (I-D-1a):

(I-D-1a)

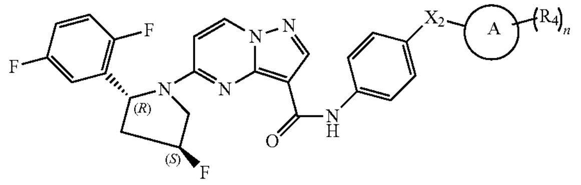

wherein, $R_1$, $R_3$, $R_4$, $X_1$, $X_2$, ring A and n are as described for the compound of formula (I-A-1a) of the present disclosure.

In one embodiment, the present disclosure provides a compound, or a tautomer, an optical isomer, a solvate, an isotopic derivative or a pharmaceutically acceptable salt thereof, wherein the compound has a structure of formula (I-C-1a):

(I-C-1a)

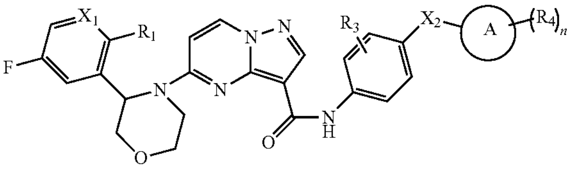

wherein, $R_1$, $R_3$, $R_4$, $X_1$, $X_2$, ring A and n are as described for the compound of formula (I-A-1a) of the present disclosure.

In one embodiment, the present disclosure provides a compound, or a tautomer, an optical isomer, a solvate, an isotopic derivative or a pharmaceutically acceptable salt thereof, wherein the compound has a structure of formula (I-C-1a-1):

(I-C-1a-1)

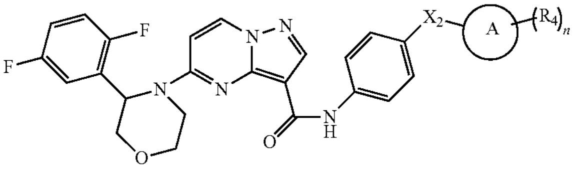

wherein, $R_4$, $X_2$, ring A and n are as described for the compound of formula (I-A-1a) of the present disclosure.

In one embodiment, the present disclosure provides a compound, or a tautomer, an optical isomer, a solvate, an isotopic derivative or a pharmaceutically acceptable salt thereof, wherein the compound has a structure of formula (I-C-1a-2):

(I-C-1a-2)

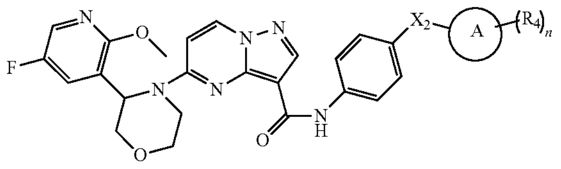

wherein, $R_4$, $X_2$, ring A and n are as described for the compound of formula (I-A-1a) of the present disclosure.

In one embodiment, the present disclosure provides a compound, or a tautomer, an optical isomer, a solvate, an isotopic derivative or a pharmaceutically acceptable salt thereof, wherein, ring A is selected from: $C_{3-6}$ cycloalkyl, 4-6 membered heterocycloalkyl, $C_{6-8}$ bridged cyclyl, 6-8 membered heterobridged cyclyl, $C_{8-10}$ fused cyclyl, 8-10 membered heterofused cyclyl, $C_{7-12}$ monospiro cyclyl, and 7-12 membered heteromonospiro cyclyl, wherein heteroatoms in the heterocycloalkyl, the heterobridged cyclyl, the heterofused cyclyl, and the heteromonospiro cyclyl are independently selected from O, S, and N, and the number of the heteroatoms is selected from 1, 2, and 3.

In one embodiment, the present disclosure provides a compound, or a tautomer, an optical isomer, a solvate, an isotopic derivative or a pharmaceutically acceptable salt thereof, wherein ring A is selected from the following structures:

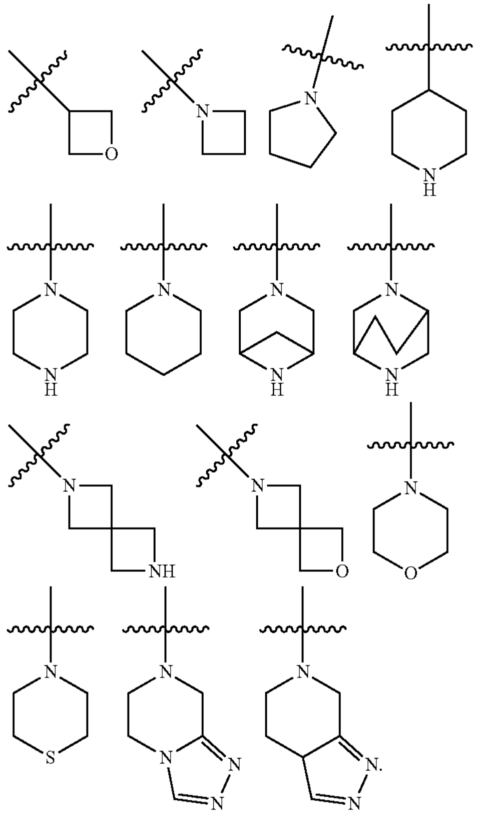

In one embodiment, the present disclosure provides a compound, or a tautomer, an optical isomer, a solvate, an isotopic derivative or a pharmaceutically acceptable salt thereof, wherein, $R_4$ is independently selected from: —H, —OH, halogen, —CN, oxo, substituted or unsubstituted $C_{1-6}$ alkyl, —COOH, —$CONH_2$, —CO—$CR_{4a}R_{4b}$—OH, and —CO—$R_{4b}$, wherein the oxo means that two H of the same substitution site are substituted with the same O to form a double bond; $R_{4a}$ is selected from hydrogen and unsubstituted or substituted $C_{1-4}$ alkyl; $R_{4b}$ is selected from unsubstituted or substituted $C_{1-6}$ alkyl and unsubstituted or substituted $C_{3-6}$ cycloalkyl, a substituent for the substitution is independently selected from —OH, —$NH_2$, and halogen, and the number of the substituents is selected from 1, 2, and 3.

In one embodiment, the present disclosure provides a compound, or a tautomer, an optical isomer, a solvate, an isotopic derivative or a pharmaceutically acceptable salt thereof, wherein the compound has the following structures:

| Serial number | Structural formulas |
| --- | --- |
| 1 | 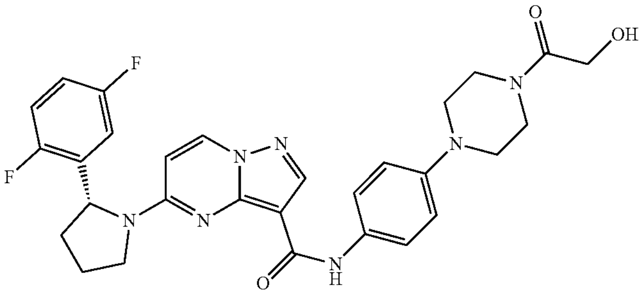 [SMILES: O=C(Nc1ccc(N2CCN(C(=O)CO)CC2)cc1)c1cnn2ccc(N3CCC[C@@H]3c3cc(F)ccc3F)nc12] |
| 2 | 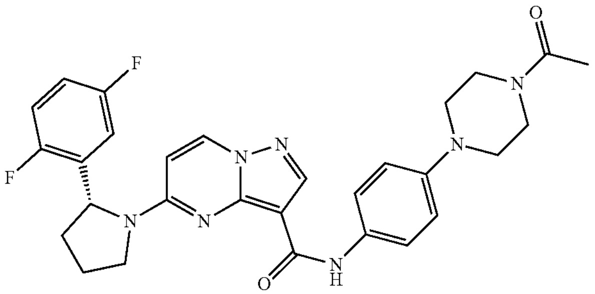 [SMILES: CC(=O)N1CCN(c2ccc(NC(=O)c3cnn4ccc(N5CCC[C@@H]5c5cc(F)ccc5F)nc34)cc2)CC1] |
| 3 | 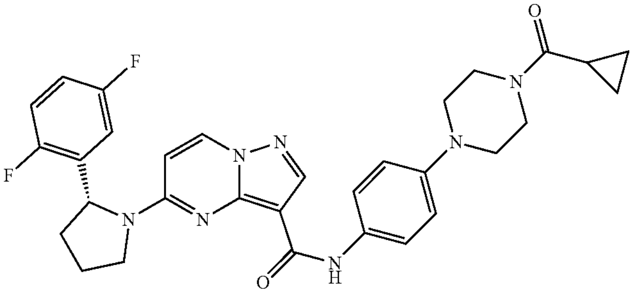 [SMILES: O=C(Nc1ccc(N2CCN(C(=O)C3CC3)CC2)cc1)c1cnn2ccc(N3CCC[C@@H]3c3cc(F)ccc3F)nc12] |
| 4 | 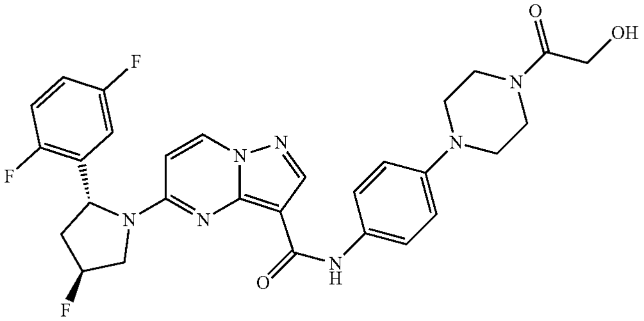 [SMILES: O=C(Nc1ccc(N2CCN(C(=O)CO)CC2)cc1)c1cnn2ccc(N3C[C@@H](F)C[C@@H]3c3cc(F)ccc3F)nc12] |

-continued
| Serial number | Structural formulas |
| --- | --- |
| 5 | 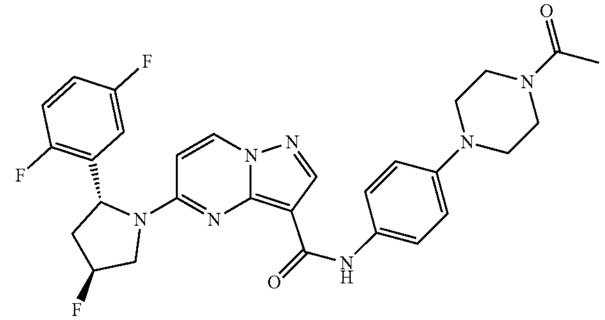 [SMILES: CC(=O)N1CCN(c2ccc(NC(=O)c3cnn4ccc(N5C[C@@H](F)C[C@@H]5c5cc(F)ccc5F)nc34)cc2)CC1] |
| 6 | 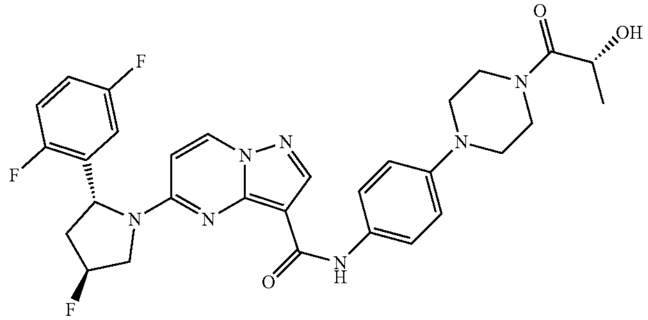 [SMILES: C[C@@H](O)C(=O)N1CCN(c2ccc(NC(=O)c3cnn4ccc(N5C[C@@H](F)C[C@@H]5c5cc(F)ccc5F)nc34)cc2)CC1] |
| 7 | 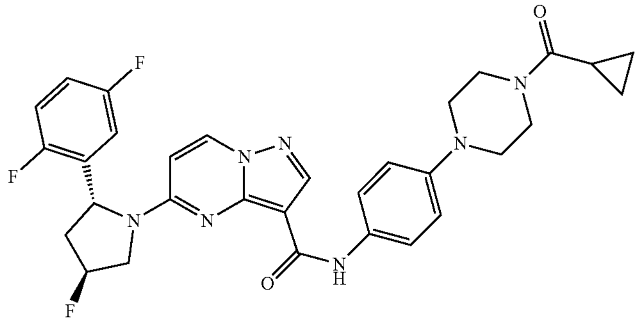 [SMILES: O=C(Nc1ccc(N2CCN(C(=O)C3CC3)CC2)cc1)c1cnn2ccc(N3C[C@@H](F)C[C@@H]3c3cc(F)ccc3F)nc12] |
| 8 | 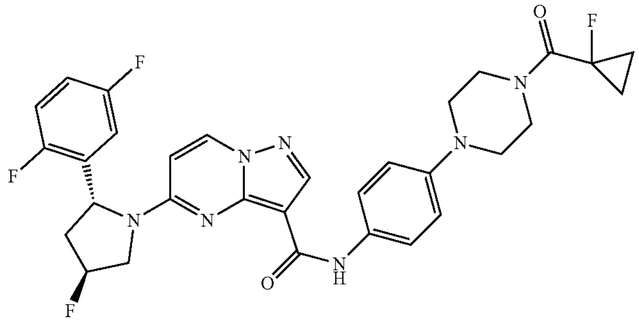 |

-continued
| Serial number | Structural formulas |
|---|---|
| 9 | 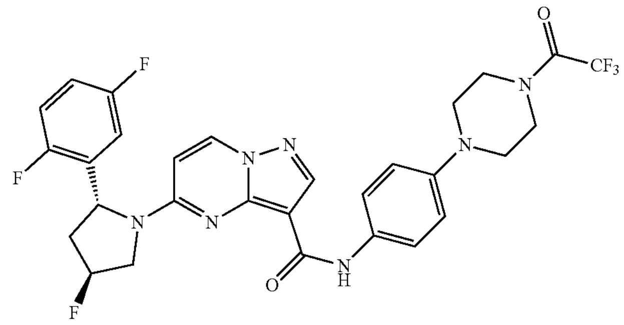 |
| 10 | 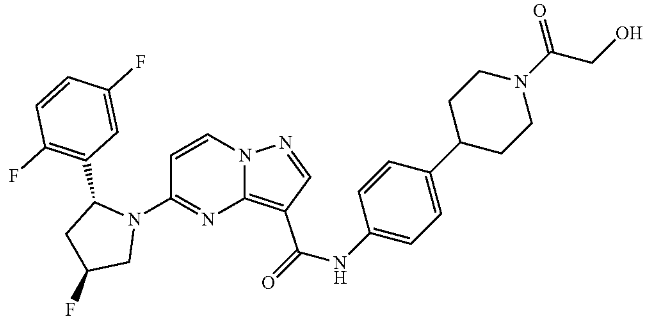 [SMILES: O=C(Nc1ccc(C2CCN(C(=O)CO)CC2)cc1)c1cnn2ccc(N3C[C@@H](F)C[C@@H]3c3cc(F)ccc3F)nc12] |
| 11 | 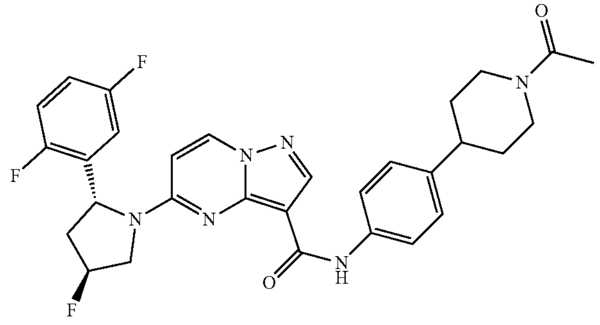 |
| 12 | 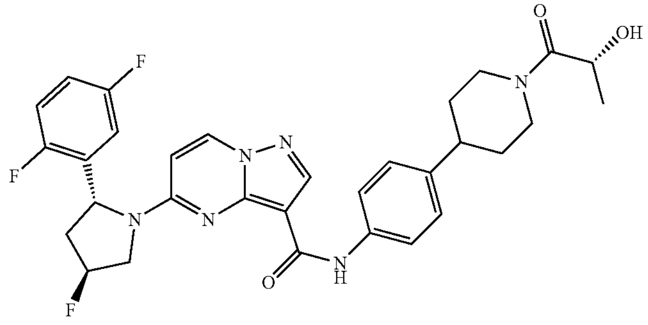 |

-continued
| Serial number | Structural formulas |
| --- | --- |
| 13 | 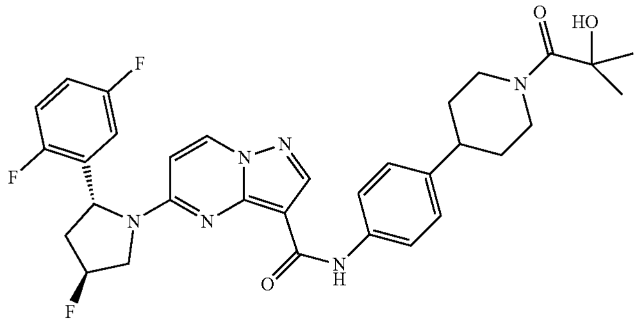 [SMILES: CC(C)(O)C(=O)N1CCC(c2ccc(NC(=O)c3cnn4ccc(N5C[C@@H](F)C[C@@H]5c5cc(F)ccc5F)nc34)cc2)CC1] |
| 14 | 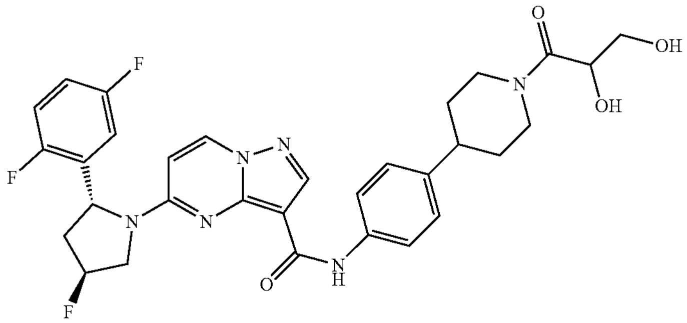 [SMILES: O=C(Nc1ccc(C2CCN(C(=O)C(O)CO)CC2)cc1)c1cnn2ccc(N3C[C@@H](F)C[C@@H]3c3cc(F)ccc3F)nc12] |
| 15 | 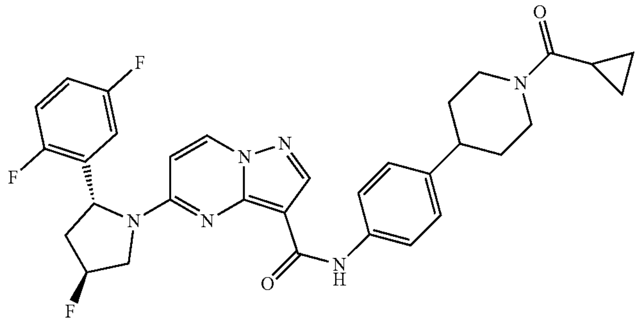 [SMILES: O=C(Nc1ccc(C2CCN(C(=O)C3CC3)CC2)cc1)c1cnn2ccc(N3C[C@@H](F)C[C@@H]3c3cc(F)ccc3F)nc12] |
| 16 | 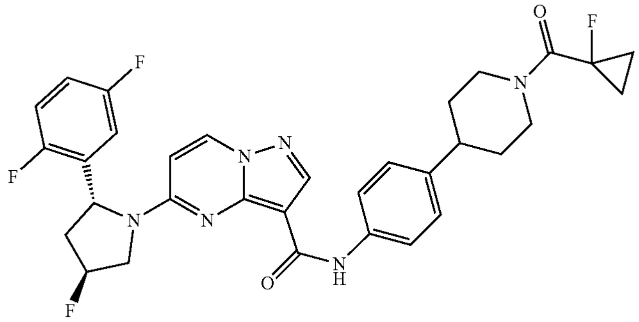 [SMILES: O=C(Nc1ccc(C2CCN(C(=O)C3(F)CC3)CC2)cc1)c1cnn2ccc(N3C[C@@H](F)C[C@@H]3c3cc(F)ccc3F)nc12] |

-continued
| Serial number | Structural formulas |
|---|---|
| 17 | 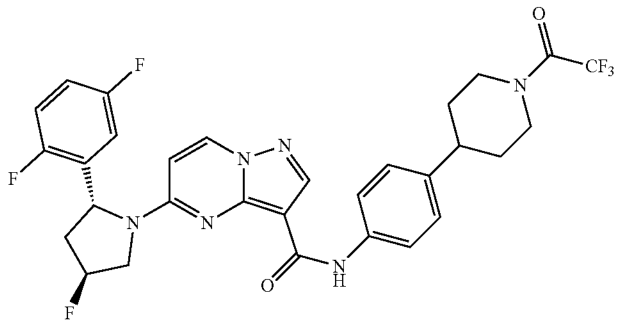 |
| 18 | 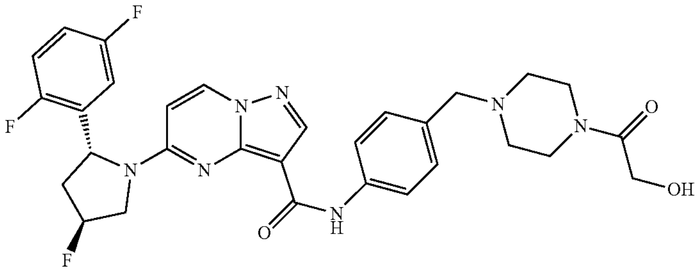 [SMILES: O=C(Nc1ccc(CN2CCN(C(=O)CO)CC2)cc1)c1cnn2ccc(N3C[C@@H](F)C[C@@H]3c3cc(F)ccc3F)nc12] |
| 19 | 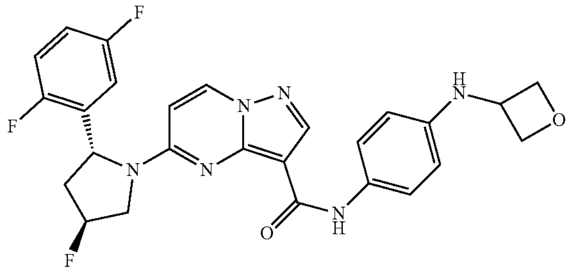 [SMILES: O=C(Nc1ccc(NC2COC2)cc1)c1cnn2ccc(N3C[C@@H](F)C[C@@H]3c3cc(F)ccc3F)nc12] |
| 20 | 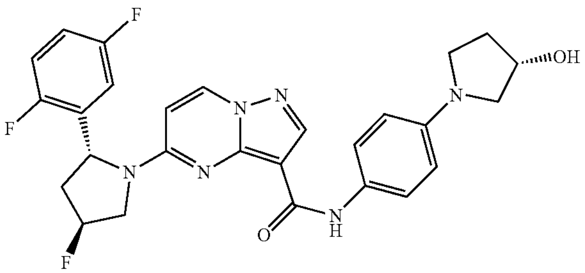 [SMILES: O=C(Nc1ccc(N2CC[C@H](O)C2)cc1)c1cnn2ccc(N3C[C@@H](F)C[C@@H]3c3cc(F)ccc3F)nc12] |
| 21 | 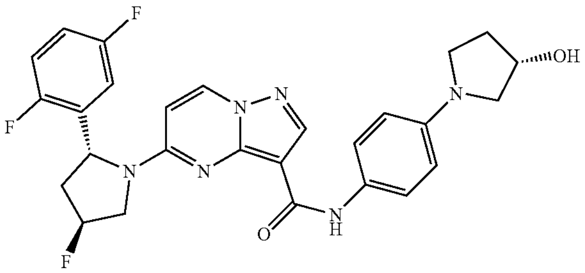 [SMILES: O=C(Nc1ccc(N2CC[C@H](O)C2)cc1)c1cnn2ccc(N3C[C@@H](F)C[C@@H]3c3cc(F)ccc3F)nc12] |

-continued
| Serial number | Structural formulas |
|---|---|
| 22 | 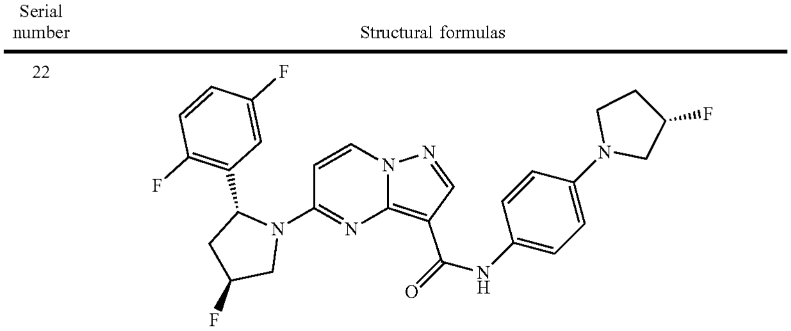 |
| 23 | 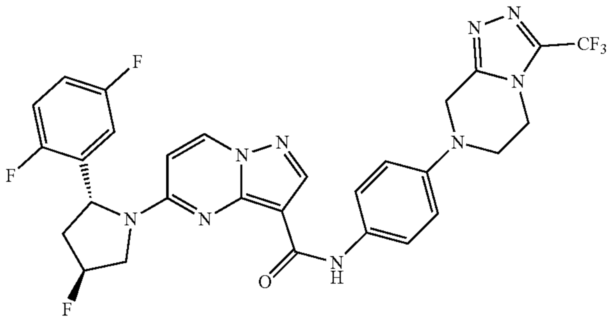 [SMILES: O=C(Nc1ccc(N2CCn3c(nnc3C(F)(F)F)C2)cc1)c1cnn2ccc(N3C[C@@H](F)C[C@@H]3c3cc(F)ccc3F)nc12] |
| 24 | 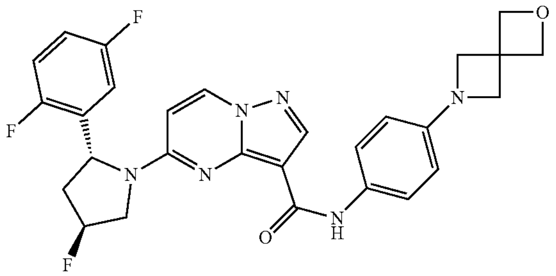 [SMILES: O=C(Nc1ccc(N2CC3(COC3)C2)cc1)c1cnn2ccc(N3C[C@@H](F)C[C@@H]3c3cc(F)ccc3F)nc12] |
| 25 | 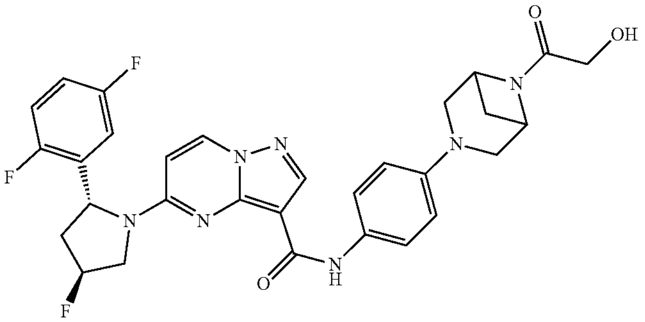 [SMILES: O=C(Nc1ccc(N2CC3CC(C2)N3C(=O)CO)cc1)c1cnn2ccc(N3C[C@@H](F)C[C@@H]3c3cc(F)ccc3F)nc12] |
| 26 | 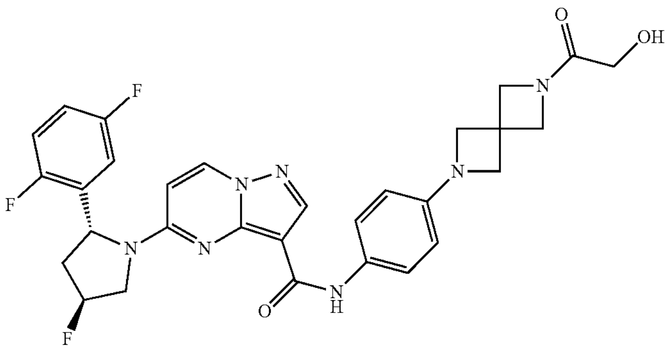 [SMILES: O=C(Nc1ccc(N2CC3(CN(C(=O)CO)C3)C2)cc1)c1cnn2ccc(N3C[C@@H](F)C[C@@H]3c3cc(F)ccc3F)nc12] |

-continued
| Serial number | Structural formulas |
|---|---|
| 27 | 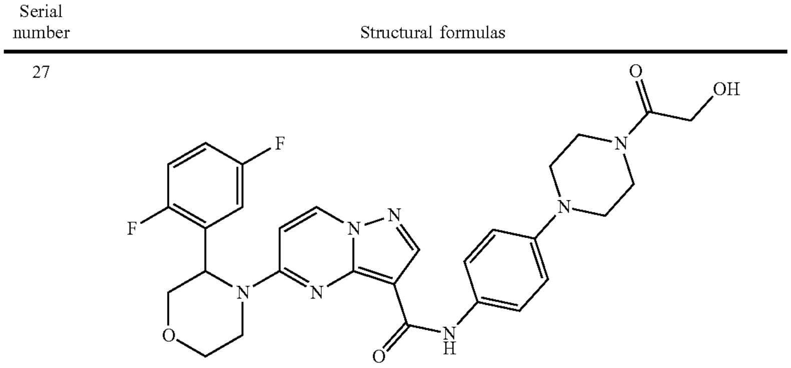 |
| 28 | 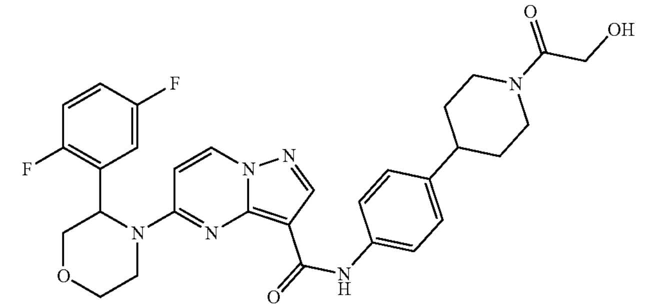 [SMILES: O=C(Nc1ccc(C2CCN(C(=O)CO)CC2)cc1)c1cnn2ccc(N3CCOCC3c3cc(F)ccc3F)nc12] |
| 29 | 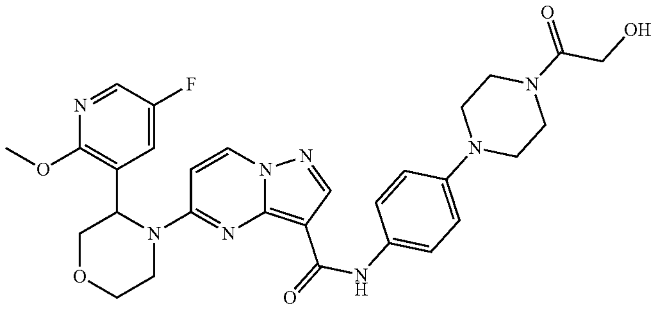 [SMILES: COc1ncc(F)cc1C1COCCN1c1ccn2ncc(C(=O)Nc3ccc(N4CCN(C(=O)CO)CC4)cc3)c2n1] |
| 30 | 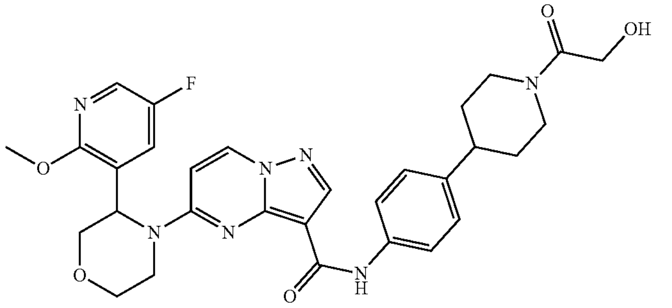 [SMILES: COc1ncc(F)cc1C1COCCN1c1ccn2ncc(C(=O)Nc3ccc(C4CCN(C(=O)CO)CC4)cc3)c2n1] |
| 31 | 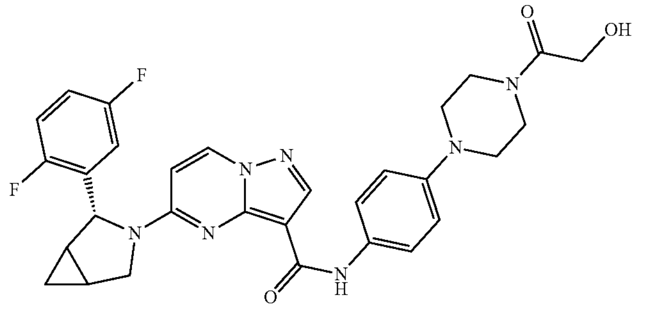 [SMILES: O=C(Nc1ccc(N2CCN(C(=O)CO)CC2)cc1)c1cnn2ccc(N3CC4CC4[C@@H]3c3cc(F)ccc3F)nc12] |

-continued
| Serial number | Structural formulas |
|---|---|
| 32 | 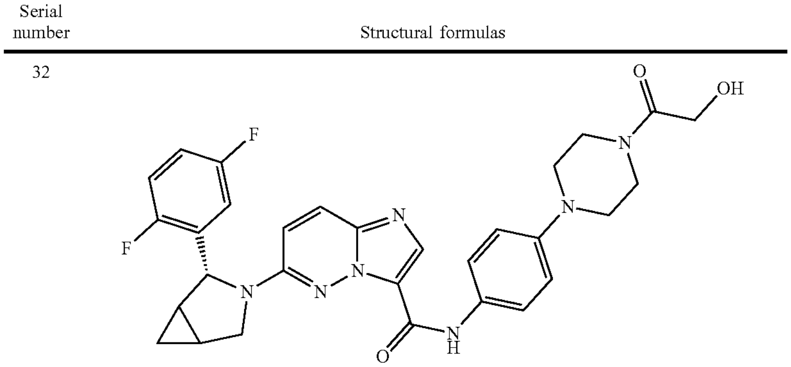 |
| 33 | 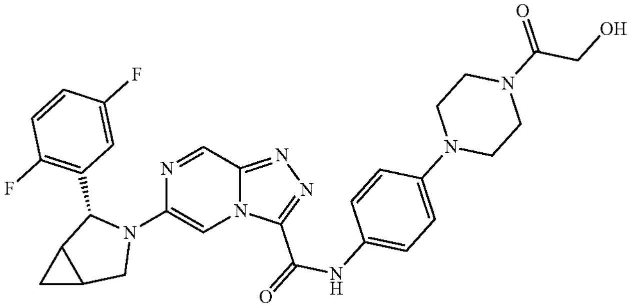 [SMILES: O=C(Nc1ccc(N2CCN(C(=O)CO)CC2)cc1)c1nnc2cnc(N3CC4CC4[C@@H]3c3cc(F)ccc3F)cn12] |
| 34 | 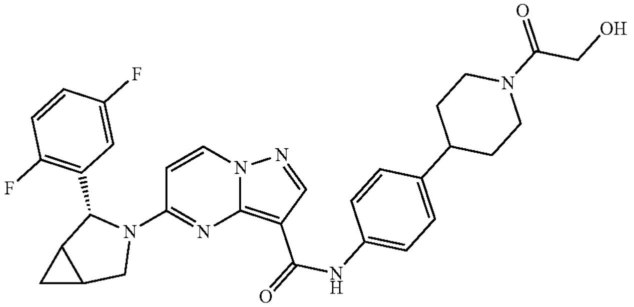 [SMILES: O=C(Nc1ccc(C2CCN(C(=O)CO)CC2)cc1)c1cnn2ccc(N3CC4CC4[C@@H]3c3cc(F)ccc3F)nc12] |
| 35 | 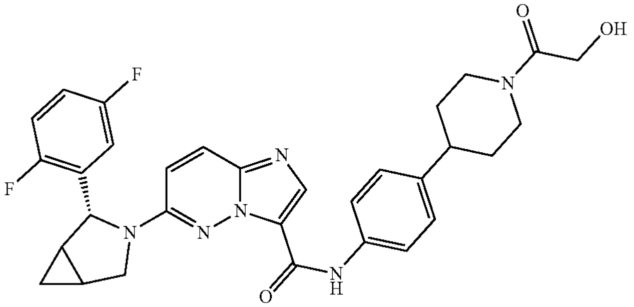 [SMILES: O=C(Nc1ccc(C2CCN(C(=O)CO)CC2)cc1)c1cnc2ccc(N3CC4CC4[C@@H]3c3cc(F)ccc3F)nn12] |
| 36 | 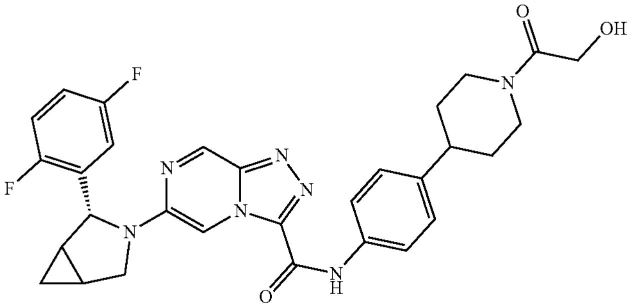 [SMILES: O=C(Nc1ccc(C2CCN(C(=O)CO)CC2)cc1)c1nnc2cnc(N3CC4CC4[C@@H]3c3cc(F)ccc3F)cn12] |

-continued
| Serial number | Structural formulas |
| --- | --- |
| 37 | 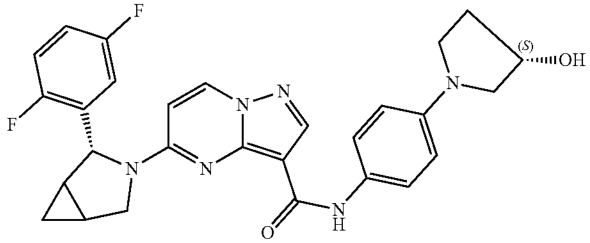 |
| 38 | 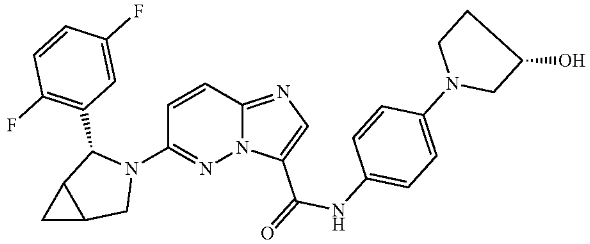 [SMILES: O=C(Nc1ccc(N2CC[C@H](O)C2)cc1)c1cnc2ccc(N3CC4CC4[C@@H]3c3cc(F)ccc3F)nn12] |
| 39 | 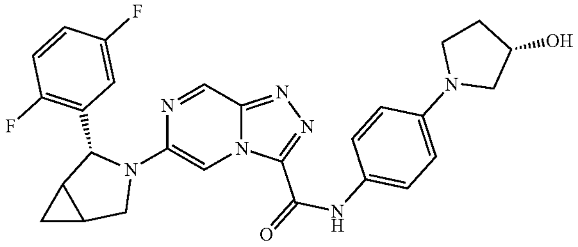 [SMILES: O=C(Nc1ccc(N2CC[C@H](O)C2)cc1)c1nnc2cnc(N3CC4CC4[C@@H]3c3cc(F)ccc3F)cn12] |
| 40 | 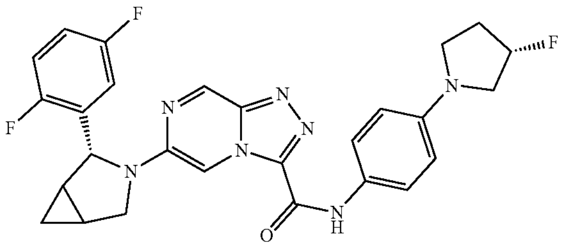 [SMILES: O=C(Nc1ccc(N2CC[C@H](F)C2)cc1)c1nnc2cnc(N3CC4CC4[C@@H]3c3cc(F)ccc3F)cn12] |
| 41 | 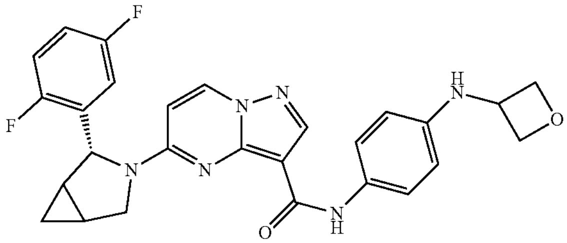 [SMILES: O=C(Nc1ccc(NC2COC2)cc1)c1cnn2ccc(N3CC4CC4[C@@H]3c3cc(F)ccc3F)nc12] |
| 42 | 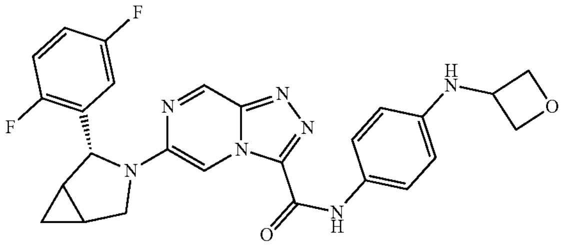 [SMILES: O=C(Nc1ccc(NC2COC2)cc1)c1nnc2cnc(N3CC4CC4[C@@H]3c3cc(F)ccc3F)cn12] |

-continued
| Serial number | Structural formulas |
|---|---|
| 43 | 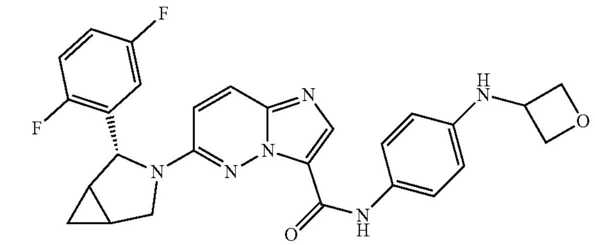 [SMILES: O=C(Nc1ccc(NC2COC2)cc1)c1cnc2ccc(N3CC4CC4[C@@H]3c3cc(F)ccc3F)nn12] |
| 44 | 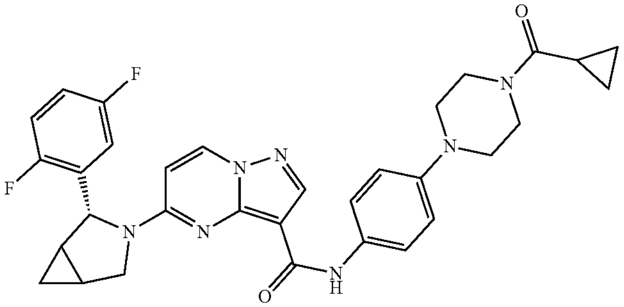 [SMILES: O=C(Nc1ccc(N2CCN(C(=O)C3CC3)CC2)cc1)c1cnn2ccc(N3CC4CC4[C@@H]3c3cc(F)ccc3F)nc12] |
| 45 | 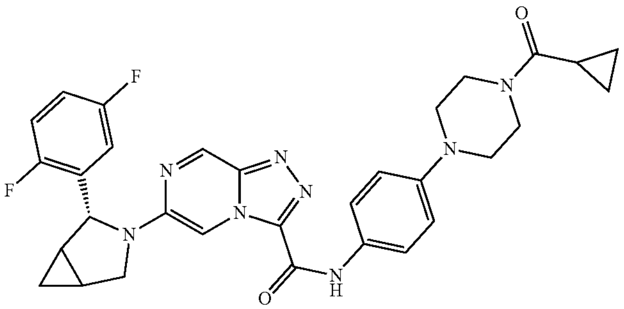 [SMILES: O=C(Nc1ccc(N2CCN(C(=O)C3CC3)CC2)cc1)c1nnc2cnc(N3CC4CC4[C@@H]3c3cc(F)ccc3F)cn12] |
| 46 | 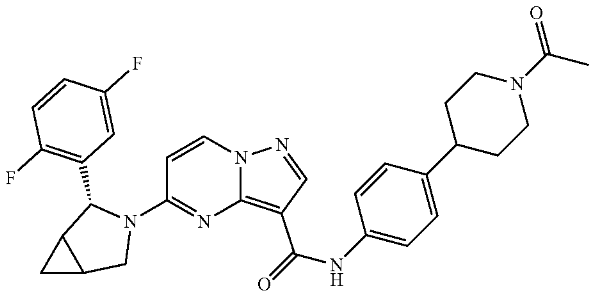 [SMILES: CC(=O)N1CCC(c2ccc(NC(=O)c3cnn4ccc(N5CC6CC6[C@@H]5c5cc(F)ccc5F)nc34)cc2)CC1] |
| 47 | 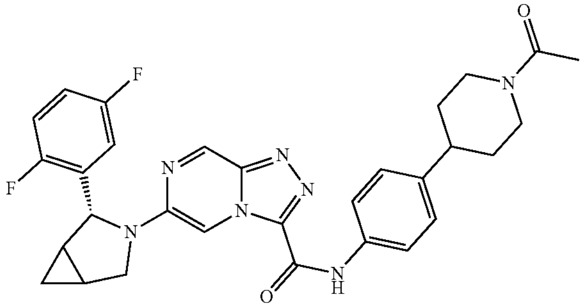 [SMILES: CC(=O)N1CCC(c2ccc(NC(=O)c3nnc4cnc(N5CC6CC6[C@@H]5c5cc(F)ccc5F)cn34)cc2)CC1] |

-continued
| Serial number | Structural formulas |
|---|---|
| 1a | 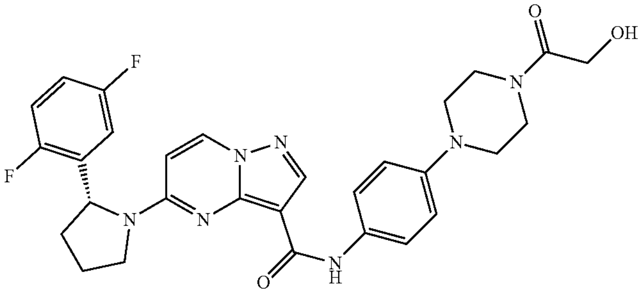 [SMILES: O=C(Nc1ccc(N2CCN(C(=O)CO)CC2)cc1)c1cnn2ccc(N3CCC[C@@H]3c3cc(F)ccc3F)nc12] |
| 1b | 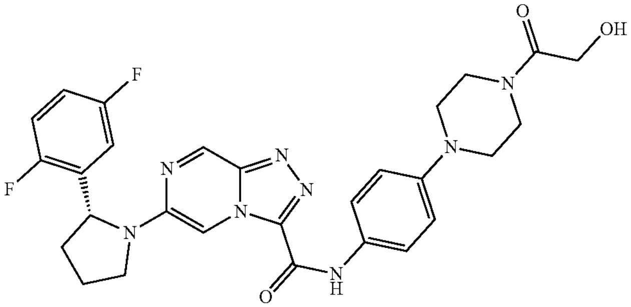 [SMILES: O=C(Nc1ccc(N2CCN(C(=O)CO)CC2)cc1)c1nnc2cnc(N3CCC[C@@H]3c3cc(F)ccc3F)cn12] |
| 4a | 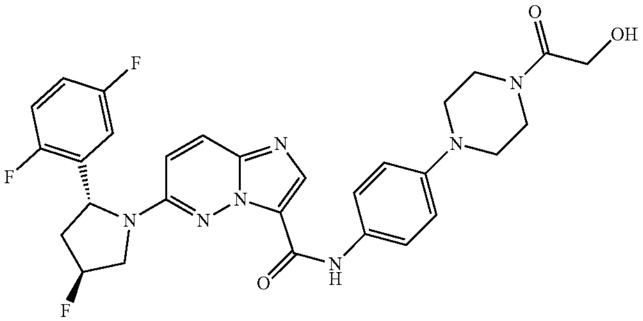 [SMILES: O=C(Nc1ccc(N2CCN(C(=O)CO)CC2)cc1)c1cnc2ccc(N3C[C@@H](F)C[C@@H]3c3cc(F)ccc3F)nn12] |
| 4b | 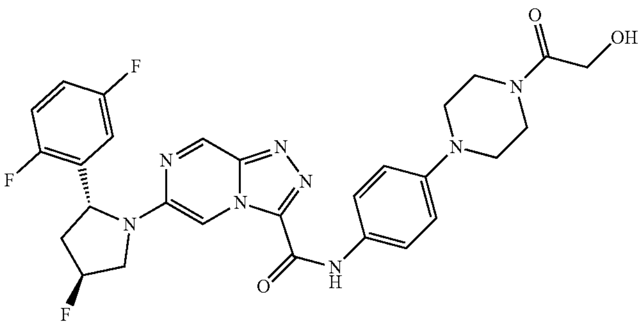 |

-continued
| Serial number | Structural formulas |
| --- | --- |
| 5a | 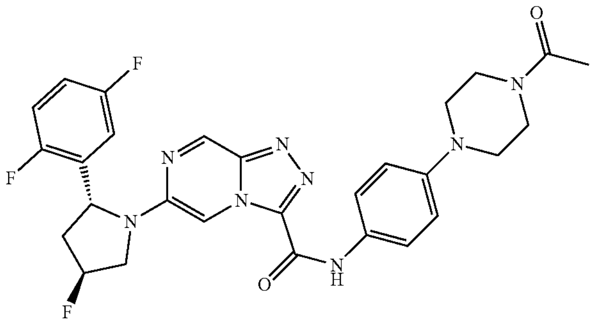 [SMILES: CC(=O)N1CCN(c2ccc(NC(=O)c3nnc4cnc(N5C[C@@H](F)C[C@@H]5c5cc(F)ccc5F)cn34)cc2)CC1] |
| 7a | 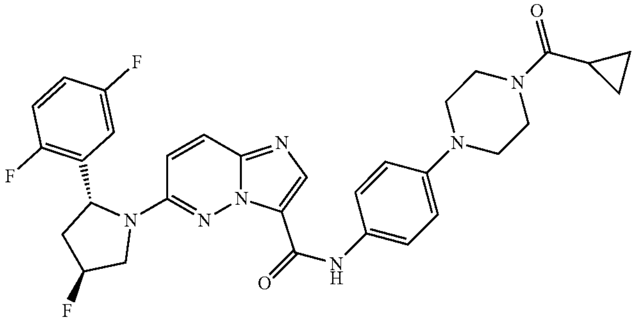 [SMILES: O=C(Nc1ccc(N2CCN(C(=O)C3CC3)CC2)cc1)c1cnc2ccc(N3C[C@@H](F)C[C@@H]3c3cc(F)ccc3F)nn12] |
| 7b | 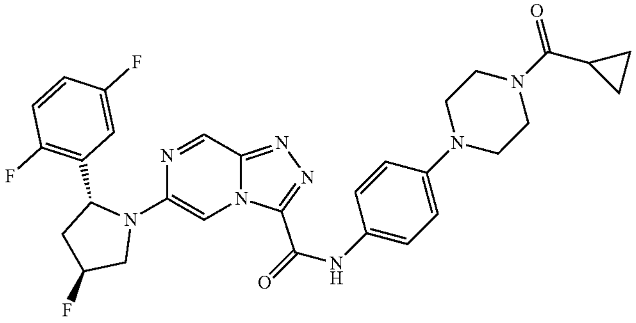 [SMILES: O=C(Nc1ccc(N2CCN(C(=O)C3CC3)CC2)cc1)c1nnc2cnc(N3C[C@@H](F)C[C@@H]3c3cc(F)ccc3F)cn12] |
| 10a | 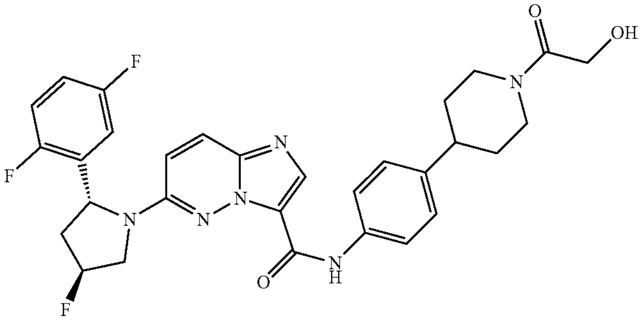 [SMILES: O=C(Nc1ccc(C2CCN(C(=O)CO)CC2)cc1)c1cnc2ccc(N3C[C@@H](F)C[C@@H]3c3cc(F)ccc3F)nn12] |

-continued
| Serial number | Structural formulas |
| --- | --- |
| 10b | 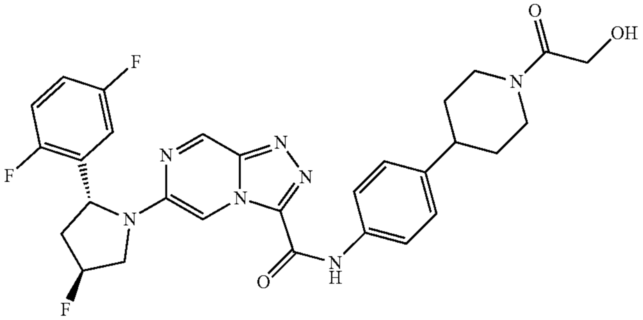 |
| 11a | 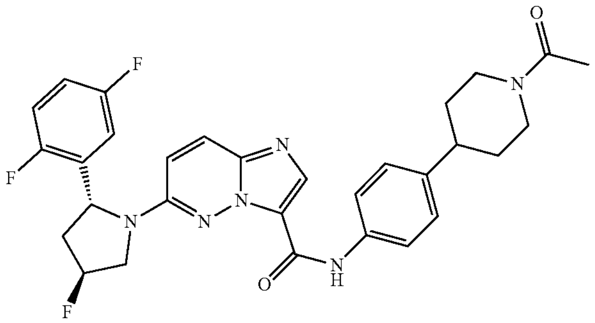 [SMILES: CC(=O)N1CCC(c2ccc(NC(=O)c3cnc4ccc(N5C[C@@H](F)C[C@@H]5c5cc(F)ccc5F)nn34)cc2)CC1] |
| 11b | 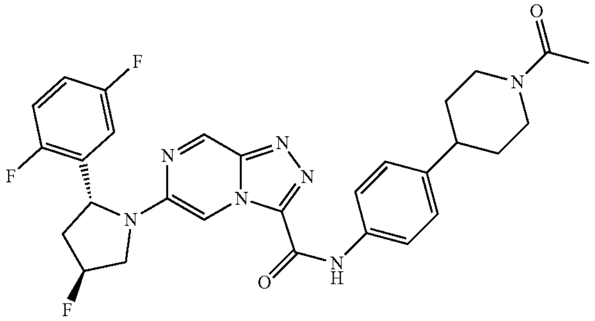 |
| 19a | 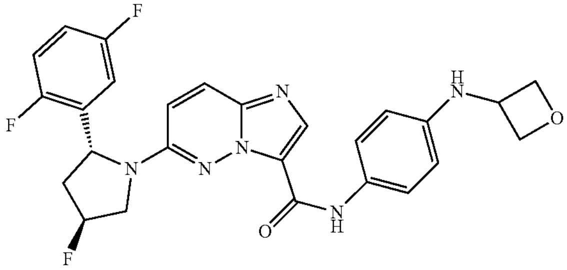 [SMILES: O=C(Nc1ccc(NC2COC2)cc1)c1cnc2ccc(N3C[C@@H](F)C[C@@H]3c3cc(F)ccc3F)nn12] |
| 19b | 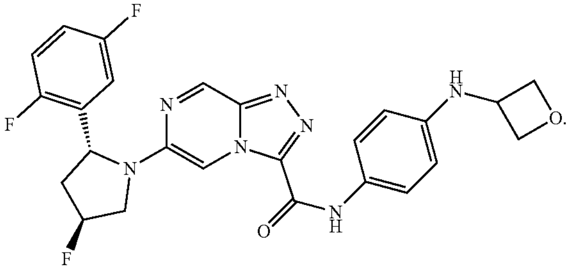 [SMILES: O=C(Nc1ccc(NC2COC2)cc1)c1nnc2cnc(N3C[C@@H](F)C[C@@H]3c3cc(F)ccc3F)cn12] |

In another aspect, the present disclosure further provides a pharmaceutical composition comprising the compound, or the tautomer, the stereoisomer, the optical isomer, the solvate, the nitrogen oxide, the prodrug, the isotopic derivative or the pharmaceutically acceptable salt thereof disclosed herein.

In another aspect, the present disclosure further provides a pharmaceutical composition comprising the compound, or the tautomer, the stereoisomer, the optical isomer, the solvate, the nitrogen oxide, the prodrug, the isotopic derivative or the pharmaceutically acceptable salt thereof disclosed herein, and a pharmaceutically acceptable auxiliary material.

In another aspect, the present disclosure further provides use of the compound, or the tautomer, the stereoisomer, the optical isomer, the solvate, the nitrogen oxide, the prodrug, the isotopic derivative or the pharmaceutically acceptable salt thereof disclosed herein, or the pharmaceutical composition disclosed herein for manufacturing a medicament for preventing and/or treating a disease mediated by TRK.

In one embodiment, the disease is selected from a pain disease, a cell proliferative disease, an inflammatory disease, a neurodegenerative disease, and an infectious disease.

In one embodiment, the disease is mediated by one, two or three of TRKA, TRKB and TRKC.

In one embodiment, the disease relates to dysregulation of an NTRK gene, a TRK protein, or the expression, activity or level thereof; preferably, it relates to the fusion, amplification, rearrangement, mutation or high expression of the NTRK gene; and further preferably, it relates to the fusion or mutation of the NTRK gene.

In another aspect, the present disclosure further provides the compound, or the tautomer, the stereoisomer, the optical isomer, the solvate, the nitrogen oxide, the prodrug, the isotopic derivative or the pharmaceutically acceptable salt thereof disclosed herein, or the pharmaceutical composition disclosed herein for use in the prevention and/or treatment of a disease mediated by TRK.

In another aspect, the present disclosure further provides a method for preventing and/or treating a disease mediated by TRK, comprising: administering to a patient the compound, or the tautomer, the stereoisomer, the optical isomer, the solvate, the nitrogen oxide, the prodrug, the isotopic derivative or the pharmaceutically acceptable salt thereof disclosed herein, or the pharmaceutical composition disclosed herein.

In another aspect, the present disclosure further provides use of the compound, or the tautomer, the stereoisomer, the optical isomer, the solvate, the nitrogen oxide, the prodrug, the isotopic derivative or the pharmaceutically acceptable salt thereof disclosed herein, or the pharmaceutical composition disclosed herein as a medicament.

In one embodiment, the medicament is used for treating a disease mediated by TRK, ALK, ROS1, or a combination thereof.

In one embodiment, the medicament is used for treating a pain disease, a cell proliferative disease, an inflammatory disease, a neurodegenerative disease, or an infectious disease.

In another aspect, the present disclosure further provides use of the compound, or the tautomer, the stereoisomer, the optical isomer, the solvate, the nitrogen oxide, the prodrug, the isotopic derivative or the pharmaceutically acceptable salt thereof disclosed herein, or the pharmaceutical composition disclosed herein for manufacturing a TRK kinase inhibitor, an ALK kinase inhibitor, or an ROS1 kinase inhibitor.

In one embodiment, the inhibitor is used for treating a disease mediated by TRK, ALK, ROS1, or a combination thereof.

In one embodiment, the inhibitor is used for treating a pain disease, a cell proliferative disease, an inflammatory disease, a neurodegenerative disease, or an infectious disease.

In another aspect, the present disclosure further provides use of the compound, or the tautomer, the stereoisomer, the optical isomer, the solvate, the nitrogen oxide, the prodrug, the isotopic derivative or the pharmaceutically acceptable salt thereof disclosed herein, or the pharmaceutical composition disclosed herein for manufacturing a medicament for treating a pain disease, a cell proliferative disease, an inflammatory disease, a neurodegenerative disease, or an infectious disease.

In one embodiment, the pain disease, the cell proliferative disease, the inflammatory disease, the neurodegenerative disease or the infectious disease relates to dysregulation of an NTRK gene, a TRK protein, or the expression, activity or level thereof; preferably, it relates to the fusion, amplification, rearrangement, mutation or high expression of the NTRK gene; and further preferably, it relates to the fusion or mutation of the NTRK gene.

In one embodiment, the pain disease, the cell proliferative disease, the inflammatory disease, the neurodegenerative disease or the infectious disease relates to dysregulation of an ROS1 gene, an ROS1 protein, or the expression, activity or level thereof; preferably, it relates to the fusion, amplification, rearrangement, mutation or high expression of the ROS1 gene; and further preferably, it relates to the fusion or mutation of the ROS1 gene.

In one embodiment, the pain disease, the cell proliferative disease, the inflammatory disease, the neurodegenerative disease or the infectious disease relates to dysregulation of a gene, a protein, or the expression, activity or level of TRK, ALK, ROS1, or a combination thereof; preferably, it relates to the fusion, amplification, rearrangement, mutation or high expression of the gene of NTRK, ALK, ROS1, or a combination thereof; and further preferably, it relates to the fusion or mutation of the gene of NTRK, ALK, ROS1, or a combination thereof.

In one embodiment, the cell proliferative disease is a tumor or cancer.

In one embodiment, the tumor or cancer is a solid tumor and a hematological tumor, preferably a solid tumor.

In one embodiment, the tumor or cancer is a hematological malignancy, lung cancer, breast cancer, ovarian cancer, prostate cancer, pancreatic cancer, brain glioma, colorectal cancer, melanoma, head and neck cancer, gallbladder cancer, thyroid cancer, glioblastoma, gastric cancer, neuroblastoma, or salivary gland cancer; preferably, the lung cancer is non-small cell lung cancer.

In another aspect, the present disclosure further provides the compound, or the tautomer, the stereoisomer, the optical isomer, the solvate, the nitrogen oxide, the prodrug, the isotopic derivative or the pharmaceutically acceptable salt thereof disclosed herein, or the pharmaceutical composition disclosed herein for use in the treatment of pain, a cell proliferative disease, inflammation, a neurodegenerative disease or an infectious disease.

In another aspect, the present disclosure further provides a method for treating a disease, comprising: administering to a patient the compound, or the tautomer, the stereoisomer, the optical isomer, the solvate, the nitrogen oxide, the prodrug, the isotopic derivative or the pharmaceutically acceptable salt thereof disclosed herein, or the pharmaceutical composition disclosed herein, wherein, the disease is pain, a cell proliferative disease, inflammation, a neurodegenerative disease or an infectious disease.

In one embodiment, the compound, or the tautomer, the stereoisomer, the optical isomer, the solvate, the nitrogen oxide, the prodrug, the isotopic derivative or the pharmaceutically acceptable salt thereof disclosed herein, or the pharmaceutical composition disclosed herein is used in combination with another one, two or more drug(s) having the effect of treating a cell proliferative disease.

In another aspect, the present disclosure further provides use of the compound, or the tautomer, the optical isomer, the stereoisomer, the solvate, the nitrogen oxide, the prodrug, the isotopic derivative or the pharmaceutically acceptable salt thereof disclosed herein, or the pharmaceutical composition disclosed herein for manufacturing a medicament for preventing and/or treating a disease mediated by TRK, ALK, ROS1, or a combination thereof.

In one embodiment, the disease is selected from a pain disease, a cell proliferative disease, an inflammatory disease, a neurodegenerative disease, and an infectious disease.

In one embodiment, the disease relates to dysregulation of a gene, a protein, or the expression, activity or level of TRK, ALK, ROS1, or a combination thereof.

In one embodiment, the disease relates to the fusion, amplification, rearrangement, mutation or high expression of the gene of NTRK, ALK, ROS1, or a combination thereof preferably, it relates to the fusion or mutation of the gene of NTRK, ALK, ROS1, or a combination thereof.

In another aspect, the present disclosure further provides a method for preventing and/or treating a disease mediated by TRK, ALK, ROS1, or a combination thereof, comprising: administering to a patient the compound, or the tautomer, the stereoisomer, the optical isomer, the solvate, the nitrogen oxide, the prodrug, the isotopic derivative or the pharmaceutically acceptable salt thereof disclosed herein, or the pharmaceutical composition disclosed herein.

Definitions

Unless otherwise specified, the following terms, as referred to herein, have the following definitions. The term "alkyl" refers to a monovalent saturated aliphatic hydrocarbon group, i.e., a linear or branched group containing 1 to 20 carbon atoms, preferably containing 1 to 10 carbon atoms (i.e., $C_{1-10}$ alkyl), further preferably containing 1 to 8 carbon atoms ($C_{1-8}$ alkyl), and more preferably containing 1 to 6 carbon atoms (i.e., $C_{1-6}$ alkyl), for example, "$C_{1-6}$ alkyl" means that the group is alkyl and the number of carbon atoms on the carbon chain is between 1 and 6 (specifically 1, 2, 3, 4, 5, or 6). Examples of the alkyl include, but are not limited to, methyl, ethyl, n-propyl, isopropyl, n-butyl, isobutyl, tert-butyl, sec-butyl, n-pentyl, neopentyl, 1,1-dimethylpropyl, 1,2-dimethylpropyl, 2,2-dimethylpropyl, 1-ethylpropyl, 2-methylbutyl, 3-methylbutyl, n-hexyl, n-heptyl, n-octyl, and the like. The term "carbocyclyl" or "carbocycle" refers to a monovalent or multivalent, saturated or partially unsaturated monocyclic, bicyclic, or tricyclic system containing 3 to 12 carbon atoms, wherein the monocyclic, bicyclic, or tricyclic system does not contain an aromatic ring. The carbon bicyclyl includes bridged cyclyl, spiro cyclyl, fused cyclyl, and the like. Bridged cyclyl means that any two rings share two atoms which may or may not be directly linked.

The term "cycloalkyl" refers to a monocyclic saturated aliphatic hydrocarbon group containing a specific number of carbon atoms, preferably containing 3 to 12 carbon atoms (i.e., $C_{3-12}$ cycloalkyl), more preferably containing 3 to 10 carbon atoms ($C_{3-10}$ cycloalkyl), and further preferably containing 3 to 6 carbon atoms ($C_{3-6}$ cycloalkyl), 4 to 6 carbon atoms ($C_{4-6}$ cycloalkyl), or 5 to 6 carbon atoms ($C_{5-6}$ cycloalkyl). Examples of the cycloalky include, but are not limited to, cyclopropyl, cyclobutyl, cyclopentyl, cyclohexyl, methylcyclopropyl, 2-ethyl-cyclopentyl, dimethylcyclobutyl, and the like. The term "alkoxy" refers to —O-alkyl, wherein the alkyl is defined as above, i.e., the alkyl contains 1 to 20 carbon atoms, preferably 1 to 10 carbon atoms, more preferably 1 to 8 carbon atoms, and further more preferably 1 to 6 carbon atoms (specifically 1, 2, 3, 4, 5, or 6). Representative examples of the alkoxy include, but are not limited to, methoxy, ethoxy, propoxy, isopropoxy, butoxy, 1-methylpropoxy, 2-methylpropoxy, tert-butoxy, pentyloxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, and the like.

The term "halogen" or "halo" refers to F, Cl, Br, and I.

The term "haloalkyl" means that one, two or more hydrogen atoms or all hydrogen atoms in the alkyl defined as above are substituted with halogen. Representative examples of the haloalkyl include $CCl_3$, $CF_3$, $CHCl_2$, $CH_2C_1$, $CH_2Br$, $CH_2I$, $CH_2CF_3$, $CF_2CF_3$, and the like.

The term "heterocyclyl" refers to a saturated or partially unsaturated monocyclic, bicyclic, or polycyclic hydrocarbon substituent, and has a non-aromatic structure containing 3 to 20 ring atoms, wherein 1, 2, 3, or more ring atoms are selected from N, O, and S, and the remaining ring atoms are C. The heterocyclyl contains preferably 3 to 12 ring atoms ($C_{3-12}$ heterocyclyl), further preferably 3 to 10 ring atoms ($C_{3-10}$ heterocyclyl), or 3 to 8 ring atoms ($C_{3-8}$ heterocyclyl), or 3 to 6 ring atoms ($C_{3-6}$ heterocyclyl), or 4 to 6 ring atoms ($C_{4-6}$ heterocyclyl), or 5 to 6 ring atoms ($C_{5-6}$ heterocyclyl). The number of the heteroatoms is preferably 1-4, more preferably 1-3 (i.e., 1, 2, or 3). Examples of the monocyclic heterocyclyl include pyrrolidinyl, imidazolidinyl, tetrahydrofuranyl, dihydropyrrolyl, piperidinyl, piperazinyl, pyranyl, and the like. Polycyclic heterocyclyl includes heterocyclyls such as heterospiro cyclyl, heterofused cyclyl, heterobridged cyclyl, and the like.

The term "heterocycloalkyl" refers to a saturated "heterocyclyl" defined as above, containing 3 to 20 ring atoms, wherein, 1, 2, 3 or more ring atoms are selected from N, O, and S, and the remaining ring atoms are C. The heterocycloalkyl contains preferably 3 to 12 ring atoms ($C_{3-12}$ heterocycloalkyl), further preferably 3 to 10 ring atoms ($C_{3-10}$ heterocycloalkyl), or 3 to 8 ring atoms ($C_{3-8}$ heterocycloalkyl), or 3 to 7 ring atoms ($C_{3-7}$ heterocycloalkyl), or 3 to 6 ring atoms ($C_{3-6}$ heterocycloalkyl), or 4 to 6 ring atoms ($C_{4-6}$ heterocycloalkyl), or 5 to 6 ring atoms ($C_{5-6}$ heterocycloalkyl). The number of the heteroatoms is preferably 1-4, more preferably 1-3 (i.e., 1, 2, or 3). Examples of the heterocycloalkyl include azacyclopropyl, ozacyclopropyl, thiocyclopropyl, azacyclobutyl, oxacyclobutyl, thiocyclobutyl, pyrrolidinyl, tetrahydrofuranyl, oxocyclohexane, piperidinyl, piperazinyl, morpholinyl, thiomorpholinyl, dioxanyl, dithiacyclohexyl, oxazolidinyl, thiazolidinyl, pyrazolidinyl, imidazolinidinyl, and the like.

The term "aryl" refers to a monocyclic, bicyclic and tricyclic aromatic carbocyclic systems containing 6 to 16 carbon atoms, or 6 to 14 carbon atoms, or 6 to 12 carbon atoms, or 6 to 10 carbon atoms, preferably 6 to 10 carbon atoms, and the term "aryl" are used interchangeably with the term "aromatic ring". Examples of the aryl group may include, but are not limited to, phenyl, naphthyl, anthryl, phenanthryl, pyrenyl, or the like.

The term “heteroaryl” refers to an aromatic monocyclic or polycyclic ring system containing a 5-12 membered structure, or preferably a 5-10 membered structure, or a 5-8 membered structure, and more preferably a 5-6 membered structure, wherein, 1, 2, 3 or more ring atoms are heteroatoms and the remaining atoms are carbon, the heteroatoms are independently selected from O, N, and S, and the number of the heteroatoms is preferably 1, 2, or 3. Examples of the heteroaryl include, but are not limited to, furanyl, thienyl, oxazolyl, thiazolyl, isoxazolyl, oxadiazolyl, thiadiazolyl, pyrrolyl, pyrazolyl, imidazolyl, triazolyl, tetrazolyl, pyridyl, pyrimidinyl, pyrazinyl, pyridazinyl, thiadiazolyl, triazinyl, phthalazinyl, quinolinyl, isoquinolinyl, pteridinyl, purinyl, indolyl, isoindolyl, indazolyl, benzofuranyl, benzothienyl, benzopyridyl, benzopyrimidinyl, benzopyrazinyl, benzimidazolyl, benzophthalizinyl, pyrrolo[2,3-b]pyridyl, imidazo[1,2-c]pyridyl, pyrazolo[1,5-c]pyridinyl, pyrazolo[1,5-c]pyrimidinyl, imidazo[1,2-b]pyridazinyl, [1,2,4]triazolo[4,3-b]pyridazinyl, [1,2,4]triazolo[1,5-a]pyrimidinyl, [1,2,4]triazolo[1,5-a]pyridinyl, and the like.

The term “pharmaceutically acceptable salt” refers to a salt which is, within the scope of sound medical judgment, suitable for use in contact with the tissues of mammals, especially humans, without excessive toxicity, irritation, allergic response and the like and commensurates with a reasonable benefit/risk ratio.

The term “salt” includes a salt prepared from inorganic acids and also includes a salt prepared from organic acids. If the compound of the present disclosure are acidic, pharmaceutically acceptable non-toxic basic salts include a salt prepared from inorganic and organic bases.

The term “stereoisomer” refers to isomers resulting from different spatial arrangement of atoms in a molecule, including configurational isomers and conformational isomers, wherein the configurational isomers include geometric isomers (or cis-trans isomers) and optical isomers (including enantiomers and diastereoisomers).

Geometric isomers may be present in the compound disclosed herein. The compound of the present disclosure may contain a carbon-carbon double bond or a carbon-nitrogen double bond in either E or Z configuration, wherein the term “E” refers to a more sequential substituent on the opposite side of the carbon-carbon or carbon-nitrogen double bond and the term “Z” represents a more sequential substituent on the same side of the carbon-carbon or carbon-nitrogen double bond (as determined using Cahn-Ingold Prelog priority rules). The compound of the present disclosure may also be present as mixtures of “E” and “Z” isomers. Substituents around cycloalkyl or heterocycloalkyl are referred to as cis- or trans-configurations.

Optical isomers refer to substances that have completely identical molecular structures and similar physicochemical properties, but different optical rotation. The compound of the present disclosure may contain asymmetrically substituted carbon atoms in the R or S configuration, wherein the terms “R” and “S” are as defined by IUPAC 1974 Recommendations for Section E, Fundamental Stereochemistry, *Pure Appl. Chem.* (1976) 45, 13-10. Compounds with asymmetrically substituted carbon atoms (with equal number of R and S configurations) are racemic at those carbon atoms. Having an excess of atoms with one configuration (relative to the other) allows the configuration to be present in higher amounts, preferably in an excess of about 85% to 90%, more preferably in an excess of about 95% to 99%, and even more preferably in an excess of greater than about 99%. Accordingly, the present disclosure includes racemic mixtures, relative and absolute optical isomers, and mixtures of relative and absolute optical isomers.

The term “nitrogen oxide” refers to an N-oxide formed by oxidizing one or more nitrogen atoms when the compound contains several amine functional groups. Specific examples of N-oxides are N-oxides of tertiary amines or N-oxides of a nitrogen atom of a nitrogen-containing heterocycle.

The term “solvate” refers to an association compound formed by one or more solvent molecules bind(s) to a compound of the present disclosure.

The term “tautomer” refers to structural isomers having different energies that are interconvertible by a lower energy barrier. If a tautomer is possible (e.g., in solution), the chemical equilibrium of the tautomer can be achieved. For example, a proton tautomer (also known as a prototropic tautomer) includes interconversion by proton migration, such as keto-enol isomerism and imine-enamine isomerism. A valence tautomer includes the interconversion by recombination of some bonding electrons. Unless otherwise indicated, all tautomeric forms of the compounds disclosed herein are within the scope of the present disclosure.

The term “isotopic derivative” means that the compound of the present disclosure can be present in an isotopically labeled or enriched form, containing one or more atoms whose atomic mass or mass number is different from that of the largest amount of atoms found in nature. The isotope may be a radioactive or non-radioactive isotope. Isotopes of atoms such as hydrogen, carbon, phosphorus, sulfur, fluorine, chlorine, and iodine include, but are not limited to: $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. The compound containing other isotopes of these and/or other atoms are within the scope of the present disclosure.

In another embodiment, isotopically labeled compounds contain deuterium ($^{2}H$), tritium ($^{3}H$), or $^{14}C$ isotopes. The isotopically labeled compounds of the present disclosure can be prepared by conventional methods well known to those skilled in the art. In this regard, relevant references include: Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003).

Isotope-containing compounds have been used in pharmaceutical research to investigate the in vivo metabolic fate of the compounds by the evaluation of the mechanism of action and metabolic pathway of the non-isotopically labeled parent compound (Blake et al., *J Pharm. Sci.* 64, 3, 367-391 (1975)). Such metabolic studies are important in the design of safe and effective therapeutic drugs, either because the in vivo active compound administered to the patient or because the metabolites produced from the parent compound prove to be toxic or carcinogenic (Kushner et al., *Can. J. Physiol. Pharmacol.,* 77, 79-88(1999); Foster et al., *Advances in Drug Research* Vol. 14, pp. 2-36, Academic press, London, 1985; Kato et al., J. *Labelled Comp. Radiopharmaceut.,* 36(10):927-932 (1995); Kushner et al., *Can. J. Physiol. Pharmacol.,* 77, 79-88 (1999)).

In addition, drugs containing non-radioactive active isotope, such as deuterated drugs called “heavy drugs”, can be used for the treatment of related diseases and conditions. Increasing the amount of an isotope present in the above compound above its natural abundance is called enrichment. Examples of the amount of enrichment include about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

Any possible site in the molecular structure can be substituted with an isotope to obtain an isotope derivative.

For example, any possible site in the molecule may be substituted with deuterium ($^2H$) to obtain the derivative in a deuterated form.

With stable isotopically labeled drugs, the physicochemical properties of the drugs, such as pKa and lipid solubility, can be altered. If isotopic substitution affects the regions involved in ligand-receptor interactions, then these effects and alterations can affect the pharmacodynamic response of the drug molecules. Although some of the physical properties of the stable isotopically labeled molecules differ from those of the isotopically unlabeled molecules, the chemical and biological properties are the same, an important difference being: any bond involving the heavy isotope and another atom is stronger than the same bond between the light isotope and that atom due to the increased mass of the heavy isotope. Accordingly, the incorporation of isotopes at the site of metabolic or enzymatic conversion may potentially slow the reaction, and may alter the pharmacokinetic properties or effects relative to non-isotopic compounds.

The term "prodrug" is a derivative of an active drug that is designed to improve some defined, undesirable physical or biological properties. Physical properties are often associated solubility (too high or insufficient lipid or water solubility) or stability, while problematic biological properties include too rapid metabolism or poor bioavailability, which may itself be associated with physicochemical properties.

Prodrugs are generally prepared as follows: a) forming esters, half-esters, carbonates, nitrates, amides, hydroxamic acids, carbamates, imines, mannich bases, phosphates, phosphate esters, and enamines of the active drugs, b) functionalizing the drugs with azo, glycoside, peptide, and ether functional groups, c) using the aminal, hemiaminal, polymer, salt, complex, phosphoramide, acetal, hemiacetal, and ketal forms of the drugs. See, for example, Andrejus Korolkovas's, *Essentials of Medicinal Chemistry*, John Wiley-Interscience Publications, John Wiley and Sons, New York (1988), pp. 97-118, the contents of which are incorporated herein by reference in their entirety. Esters can be prepared from substrates containing hydroxyl or carboxyl using conventional methods known to those skilled in the art. The typical reaction of these compounds is the substitution of one heteroatom with another atom. Amides can be prepared in a similar manner from substrates containing amino or carboxyl. Esters may also react with amines or ammonia to form amides. Another way to prepare the amide is to heat the carboxylic acid and the amine together.

The term "pharmaceutically acceptable auxiliary material" or "pharmaceutically acceptable carrier" includes, but is not limited to, any adjuvant, carrier, excipient, glidant, sweetener, diluent, preservative, dye, colorant, flavor enhancer, surfactant, wetting agent, dispersant, suspending agent, stabilizer, isotonic agent, solvent, or emulsifier that is approved by the U.S. Food and Drug Administration, the National Medical Product Administration, and the like for acceptable use in humans or domestic animals.

The term "tumor" encompasses benign tumors, malignant tumors, and borderline tumors, wherein malignant tumors are also collectively referred to as cancers.

The term "preventing" as used herein refers to a compound or drug that, when used for treating a disease or condition (e.g., cancer), can reduce the frequency or delay the onset of symptoms of a medical condition in a subject as compared with a subject who has not been administered the compound or drug (e.g., a combination product as claimed herein).

The term "treating" as used herein refers to alleviating, relieving or ameliorating a symptom of a disease or condition, ameliorating an underlying metabolic-induced symptom, and inhibiting a disease or symptom, e.g., arresting the development of a disease or condition, relieving a disease or condition, causing regression of a disease or condition, relieving a disorder caused by a disease or condition, or arresting a symptom of a disease or condition.

The term "cell proliferative disease" as used herein refers to a condition in which the growth rate of a cell population is lower or higher than the expected rate for a given physiological state and condition.

In the present disclosure, the terms used are as follows: DCM: dichloromethane; DIPEA: diisopropylethylamine; DMF: N,N-dimethylformamide; EA: ethyl acetate; NBS: N-bromosuccinimide; PE: petroleum ether; DMSO: dimethyl sulfoxide; TBTU: O-(benzotriazole-1-yl)-N,N,N',N'-tetramethyluronium tetrafluoroborate; BOP: benzotriazol-1-yloxytris(dimethylamino)phosphonium hexafluorophosphate; ATP: adenosine 5'-triphosphate; DTT: 1,4-dithiothreitol; MTT: 3-(4,5-dimethylthiazol-2 yl)-2,5-diphenyl-2H-tetrazol-3-ium bromide.

Based on the knowledge of medicinal chemistry, the nitrogen oxide, the isotopic derivative, the stereoisomer, the optical isomer, the solvate, the prodrug and the like of the compound of the present disclosure can also exhibit similar in vitro and in vivo effect to that of the compound of the present disclosure.

Beneficial Effects of Present Disclosure

The present disclosure designs a compound with a novel structure, and in vitro kinase activity inhibition test shows that: the compound of the present disclosure exhibits excellent inhibitory activity against various kinases (e.g., TRK, ALK, ROS1) and mutants thereof, particularly against TRK and mutant forms thereof; the in vitro cytostatic activity test shows that: the compound of the present disclosure has stronger inhibition effect on various TRK mutant cells, and has $IC_{50}$ of less than 10 nM, preferably less than 5 nM, and more preferably less than 1 nM on the inhibition activity of 6 kinds of cells; the results of in vivo tumor inhibition test shows that: compared with a control compound, the compound of the present disclosure has better in vivo anti-tumor effect, better tolerance and higher druggability; the research test of in vivo action mechanism shows that: the compound of the present disclosure can inhibit TRK in tumor tissues, further effectively inhibit phosphorylation of PLCγ and AKT, and inhibit growth of the tumor tissues.

BRIEF DESCRIPTION OF THE DRAWINGS

The FIGURE is a western blot graph showing the time-effect relationship of the inhibitory effect of compound No. 4 of the present disclosure on the phosphorylation of downstream target proteins in tumor tissues of TRKA-G595R mutant-resistant tumor-bearing mice.

DETAILED DESCRIPTION

The starting materials, reaction reagents, catalysts or solvents used in the following specific embodiments are commercially available or may be prepared by conventional methods known in the art.

The present disclosure will be further illustrated with reference to the following specific examples. It should be understood that these examples are merely intended to illustrate the present disclosure rather than limit the scope of the present disclosure. Test procedures without specified conditions in the following examples, are generally conducted according to conventional conditions or according to conditions recommended by the manufacturer. Unless defined otherwise, all technical and scientific terms used herein have the same meaning as commonly understood by those of ordinary skill in the art. In addition, any methods and materials similar or equivalent to those described herein can be used in the methods of the present disclosure. The preferred embodiments and materials described herein are for illustrative purposes only.

Preparation Example A: Preparation of ethyl 6-chloroimidazo[1,2-b]pyridazine-3-carboxylate

A

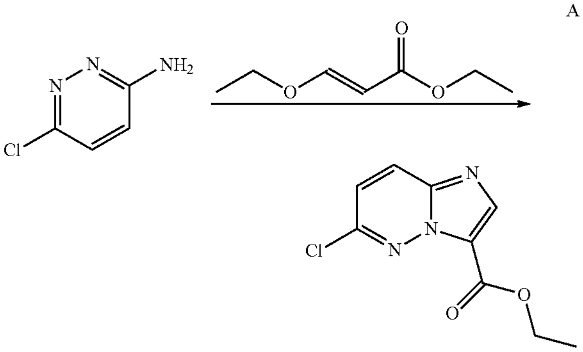

A solution of ethyl (E)-3-ethoxyacrylate (5.00 g, 34.7 mmol, 1 eq) in 1,4-dioxane (50 mL) and water (50 mL) was cooled to −10° C., added with NBS (6.80 g, 38.15 mmol, 1.1 eq) in portions, and naturally warmed to room temperature and reacted for 2 h. The reaction system was added with 6-chloro-3-aminopyridazine (4.5 g, 34.7 mmol, 1 eq), heated to 80° C. and reacted for 1.5 h, and cooled to room temperature. Then the reaction system was concentrated under reduced pressure to obtain a residue. The residue was added with water (100 mL) and EA (100 mL), stirred and separated. The aqueous phase was extracted with EA (20 mL×2). The organic phases were combined, washed with $H_2O$ (50 mL) and saturated brine (50 mL), concentrated under reduced pressure to remove the organic solvent. The residue was separated by silica gel column chromatography (eluent:n-hexane:EA=5:1 to 1:1, v/v) to give ethyl 6-chloro-imidazo[1,2-b]pyridazine-3-carboxylate (5.2 g, yield 59.75%). (ES, m/z): 225.91 $[M+H]^+$.

Intermediate Preparation Example 1: (R)—S-(2-(2,5-difluorophenyl)pyrrolidin-1-yl)pyrazolo[1,5-a]pyrimidine-3-carboxylic acid (Intermediate A1)

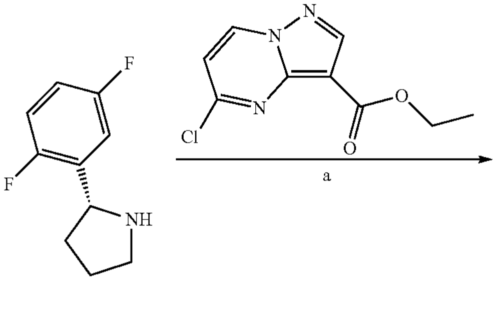

-continued

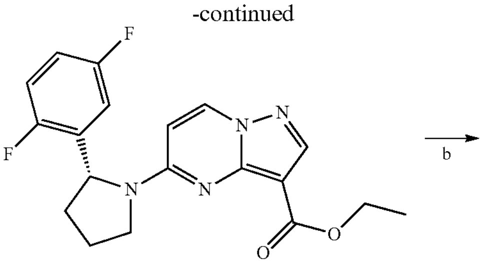

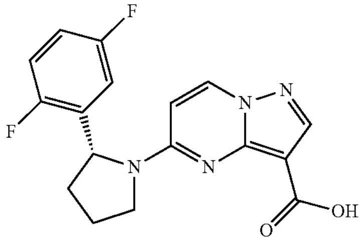

A1

Step a: a mixed solution of (R)-2-(2,5-difluorophenyl) pyrrolidine (5.0 g, 27.292 mmol), ethyl 5-chloropyrazolo[1,5-a]pyrimidine-3-carboxylate (6.14 g, 27.292 mmol), n-butanol (70 mL) and diisopropylamine (6.9 g, 68.230 mmol) was refluxed and stirred at 100° C. for 4 h, concentrated under reduced pressure to obtain an orange viscous solid. The mixture was added with anhydrous ether and stirred to precipitate a large amount of solid. Suction filtration was performed to give crude ethyl (R)-5-(2-(2,5-difluorophenyl) pyrrolidin-1-yl)pyrazolo[1,5-a] pyrimidine-3-carboxylate (6.224 g). The obtained crude product was directly used in the next step without purification. (ES, m/z): 373.02$[M+H]^+$.

Step b: crude ethyl (R)—S-(2-(2,5-difluorophenyl)pyrrolidin-1-yl)pyrazolo [1,5-a] pyrimidine-3-carboxylate (6.224 g, 16.714 mmol) was dissolved in absolute ethanol (40 mL) and stirred at 75° C. until the mixture was clear and transparent. Then the reaction system was added with an aqueous solution (40 mL) of LiOH (2.805 g, 66.856 mmol) and stirred at 75° C. for 3 h. After being cooled to room temperature, the reaction system was concentrated under reduced pressure to remove the absolute ethanol. The reaction system was slowly dropwise added with 1 N aqueous HCl solution to adjust the pH to 3-4. A large amount of white solid was precipitated. The reaction system was stirred at room temperature for 30 min, and then subjected to suction filtration. The filter cake was washed with a small amount of purified water. The filter cake was collected, air dried and weighed to give (R)—S-(2-(2,5-difluorophenyl)pyrrolidin-1-yl)pyrazolo[1,5-a]pyrimidine-3-carboxylic acid (5.64 g, 98%), (ES, m/z): 345.02 $[M+H]^+$.

Intermediate Preparation Example 2: 5-((2R,4S)-2-(2,5-difluorophenyl)-4-fluoropyrrolidin-1-yl)pyrazolo[1,5-a]pyrimidine-3-carboxylic acid (Intermediate A2)

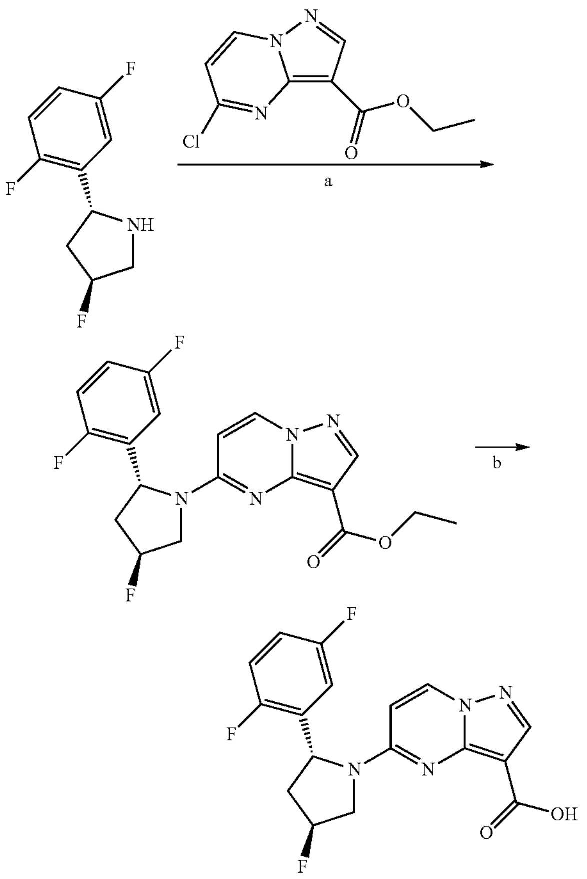 [SMILES: Fc1ccc(F)c([C@H]2CCCN2)c1 ; CCOC(=O)c1cnn2ccc(Cl)nc12 ; CCOC(=O)c1cnn2ccc(N3CCC[C@@H]3c3cc(F)ccc3F)nc12 ; O=C(O)c1cnn2ccc(N3CCC[C@@H]3c3cc(F)ccc3F)nc12 ; "A1"]

A2

Step a: a mixed solution of (2R,4S)-2-(2,5-difluorophenyl)-4-fluoropyrrolidine (5.826 g, 28.958 mmol), ethyl 5-chloropyrazolo[1,5-a]pyrimidine-3-carboxylate (6.534 g, 28.958 mmol), n-butanol (50 mL) and diisopropylamine (8.790 g, 86.874 mmol) was reacted at 100° C. for 4 h. The reaction system was concentrated under reduced pressure to give crude ethyl 5-(2R,4S)-2-(2,5-difluorophenyl)-4-fluoropyrrolidin-1-yl)pyrazolo[1,5-a]pyrimidine-3-carboxylate. The crude product was directly used in the next step without purification. (ES, m/z): 391.05[M+H]$^+$.

Step b: crude ethyl 5-((2R,4S)-2-(2,5-difluorophenyl)-4-fluoropyrrolidin-1-yl)pyrazolo[1,5-a]pyrimidine-3-carboxylate was dissolved in absolute ethanol (50 mL). The reaction system was stirred at 75° C. until the system was clear and transparent. Then the reaction system was added with an aqueous solution (50 mL) of LiOH (4.86 g, 115.832 mmol), and stirred at 75° C. for 5 h. After being cooled to room temperature, the reaction system was concentrated under reduced pressure to remove the absolute ethanol. The reaction system was slowly dropwise added with 1 N aqueous HCl solution to adjust the pH to 3-4. A large amount of white solid was precipitated. The reaction system was stirred at room temperature for 30 min, and then subjected to suction filtration. The filter cake was washed with a small amount of purified water. The filter cake was collected, dried and weighed to give a white powdery solid 5-((2R,4S)-2-(2,5-difluorophenyl)-4-fluoropyrrolidin-1-yl)pyrazolo[1,5-a]pyrimidine-3-carboxylic acid (9.9 g). The filtrate was extracted with EA (2×50 mL). The organic phases were combined, washed with water (2×50 mL) and a saturated aqueous NaCl solution (50 mL), then dried over anhydrous $Na_2SO_4$, filtered and concentrated under reduced pressure. The resulting mixture was purified by column chromatography (PE:EA=4:1 to 2:1, v/v) to give a white powdery solid 5-((2R,4S)-2-(2,5-difluorophenyl)-4-fluoropyrrolidin-1-yl) pyrazolo[1,5-a]pyrimidine-3-carboxylic acid (386 mg). The pure product 5-((2R,4S)-2-(2,5-difluorophenyl)-4-fluoropyrrolidin-1-yl)pyrazolo[1,5-a]pyrimidine-3-carboxylic acid (10.286 g, 98%) was obtained together. (ES, m/z): 363.04 [M+H]$^+$.

Intermediate Preparation Examples 1a to 2a

Referring to the process steps of the intermediate preparation examples 1 and 2, the intermediates Ala to A2a were prepared by adopting the following corresponding starting materials and preparation methods:

| Intermediate preparation example Nos. | Starting materials | Intermediate structure and Nos. | Characterization data (ES, m/z): [M + H]$^+$ |
|---|---|---|---|
| 1a | 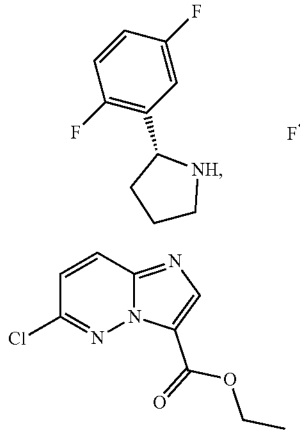 | 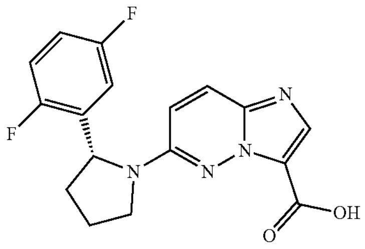 Ala | 345.04 |

-continued

| Intermediate preparation example Nos. | Starting materials | Intermediate structure and Nos. | Characterization data (ES, m/z): [M + H]+ |
|---|---|---|---|
| 2a | 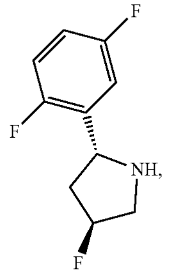 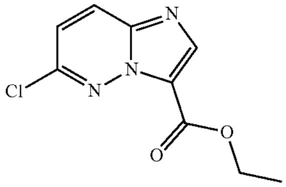 | 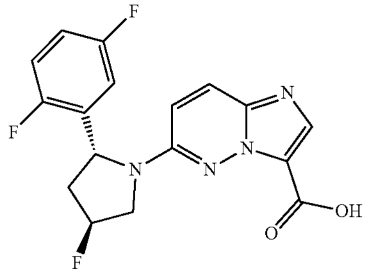 A2a | 363.02 |

Intermediate Preparation Example 3: 5-(3-(2,5-difluorophenyl)morpholinyl)pyrazolo[1,5-a]pyrimidine-3-carboxylic acid (Intermediate A3)

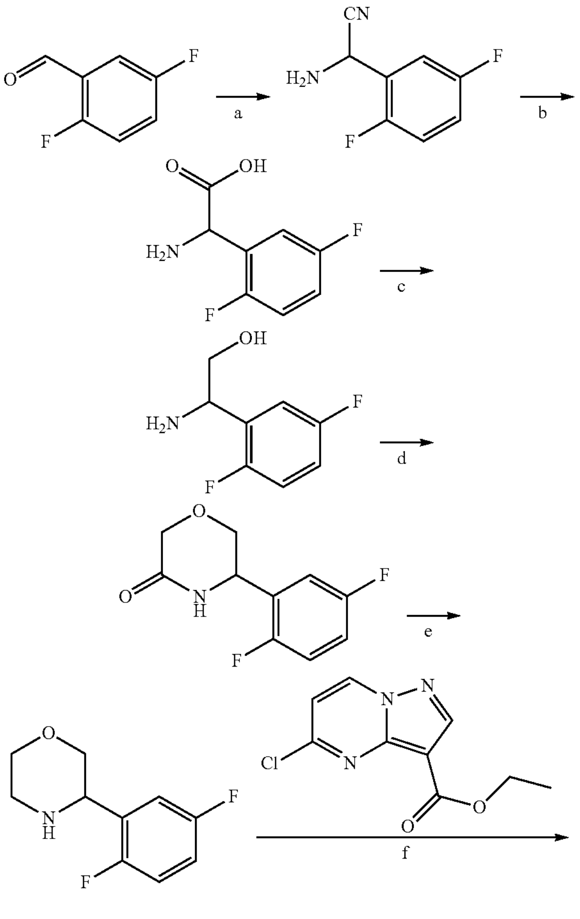

-continued

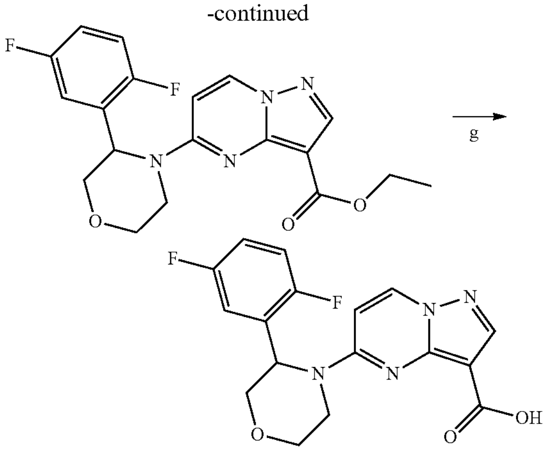

A3

Step a: under nitrogen atmosphere, trimethylsilyl cyanide (39.66 g, 0.4 mol) was added dropwise into a solution (30 mL) of 2,5-difluorobenzaldehyde (28.4 g, 0.2 mol) in 7 mol/L $NH_3/CH_3OH$ at 0° C. The reaction system was stirred at room temperature overnight after the dropwise addition was finished. The reaction liquid was concentrated under reduced pressure, and the residue was purified by column chromatography ($CH_2Cl_2$:$CH_3OH$=50:1, V/V) to give 2-amino-2-(2,5-difluorophenyl)acetonitrile (21.92 g, 65.2%). (ES, m/z): 169[M+H]+.

Step b: 2-amino-2-(2,5-difluorophenyl)acetonitrile (21.92 g, 130 mmol) was added into 2 mol/L aqueous NaOH solution (130 mL). The reaction system was reacted under reflux for 6 hours, and then cooled to 0° C. The pH of the mixture was adjusted to 3 with concentrated hydrochloric acid, and then concentrated under reduced pressure. The residue was dissolved in tetrahydrofuran (200 mL), stirred for 30 min and filtered. The filtrate was dried over anhydrous sodium sulfate overnight, filtered, and concentrated under reduced pressure to give crude 2-amino-2-(2,5-difluorophenyl)acetic acid (20.78 g), which was directly used in the next step without purification. (ES, m/z): 186.02[M−H]$^-$.

Step c: under nitrogen atmosphere, a solution of 2-amino-2-(2,5-difluorophenyl)acetic acid (20.78 g, 111 mmol) in tetrahydrofuran (600 mL) was cooled to −10° C. to −5° C., added with lithium aluminum hydride (10.53 g, 278 mmol) in portions, and reacted at room temperature overnight after the addition was finished. The reaction liquid was added with saturated ammonium chloride solution (500 mL) to quench the reaction, and filtered through celite. The filtrate was separated. The aqueous phase was extracted with EA (2×100 mL). The organic phases were combined, dried over anhydrous sodium sulfate, and filtered; and the filtrate was concentrated under reduced pressure. The residue was purified by column chromatography ($CH_2Cl_2$:$CH_3OH$=10:1, V/V) to give 2-amino-2-(2,5-difluorophenyl)ethanol (7.177 g, 32% two-step yield). (ES, m/z): 174.02[M+H]$^+$.

Step d: under nitrogen atmosphere, chloroacetyl chloride (5.62 g, 49.736 mmol) was added into a solution of 2-amino-2-(2,5-difluorophenyl)ethanol (7.177 g, 41.447 mmol) and triethylamine (8.388 g, 82.894 mmol) in tetrahydrofuran (200 mL) at 0° C. The temperature was maintained and the reaction system was stirred for 30 min. The reaction system was added with 60% NaH (4.974 g, 124.341 mmol) in portions. The reaction mixture was reacted at room temperature for 2 h after the addition was finished, quenched with saturated ammonium chloride (100 mL). The aqueous phase was extracted with EA (2×50 mL). The organic phases were combined, dried over anhydrous sodium sulfate, filtered, and concentrated under reduced pressure. The residue was purified by column chromatography ($CH_2Cl_2$:$CH_3OH$=80:1 to 20:1, V/V) to give 5-(2,5-difluorophenyl)morpholine-3-one (4.532 g, 51.3%). (ES, m/z): 214.01[M+H]$^+$.

Step e: under nitrogen atmosphere, lithium aluminum hydride (3.229 g, 85.849 mmol) was added into a solution of 5-(2,5-difluorophenyl)morpholine-3-one (4.532 g, 21.271 mmol) in tetrahydrofuran (100 mL) at 0° C. in portions. The reaction system was reacted for 2 h at 50° C. after the addition was finished, and then cooled to 0° C. The mixture was quenched with saturated ammonium chloride (90 mL), and concentrated under reduced pressure. The aqueous phase was extracted with EA (3×50 mL). The organic phases were combined, washed with water (50 mL) and brine (50 mL), then dried over anhydrous sodium sulfate, filtered, and concentrated under reduced pressure. The residue was purified by column chromatography ($CH_2Cl_2$:$CH_3OH$=50:1 to 25:1, V/V) to give 3-(2,5-difluorophenyl)morpholine (3.40 g, 80.3%). (ES, m/z): 200.03 [M+H]$^+$.

Step f: a mixed solution of 3-(2,5-difluorophenyl)morpholine (3.40 g, 17.068 mmol), ethyl 5-chloropyrazolo[1,5-a]pyrimidine-3-carboxylate (3.851 g, 17.068 mmol), n-butanol (50 mL) and diisopropylamine (5.181 g, 51.204 mmol) was reacted at 100° C. overnight. The reaction system was concentrated under reduced pressure. The residue was added with EA (100 mL) and water (100 mL), and the mixture was stirred. The aqueous phase was extracted with EA (2×50 mL). The organic phases were combined, washed with water (100 mL) and brine (50 mL), then dried over anhydrous sodium sulfate, filtered, and concentrated under reduced pressure. The residue was purified by column chromatography (n-hexane:ethyl acetate=50:1 to 10:1, V/V) to give ethyl 5-(3-(2,5-difluorophenyl)morpholinyl)pyrazolo[1,5-a]pyrimidine-3-carboxylate (6.066 g, 91.5%). (ES, m/z): 389.05 [M+H]$^+$.

Step g: to a solution of ethyl 5-(3-(2,5-difluorophenyl)morpholinyl)pyrazolo[1,5-a]pyrimidine-3-carboxylate (6.066 g, 15.623 mmol) in ethanol (60 mL) was added an aqueous solution (60 mL) of LiOH (2.622 g, 62.492 mmol), and the mixture was heated to 75° C. for reaction overnight. The reaction system was cooled to room temperature and concentrated under reduced pressure. The aqueous phase was adjusted to pH=2 to 3 with 1 N aqueous hydrochloric acid solution and extracted with EA (3×60 mL). The organic phases were combined, washed with water (100 mL) and brine (50 mL), then dried over anhydrous $Na_2SO_4$, filtered, concentrated under reduced pressure, and purified by column chromatography (PE:EA=4:1 to 1:1, v/v) to give 5-(3-(2,5-difluorophenyl)morpholinyl)pyrazolo[1,5-a]pyrimidine-3-carboxylic acid (5.324 g, 94.6%). (ES, m/z): 361.09 [M+H]$^+$.

Intermediate Preparation Example 4: 5-(3-(5-fluoro-2-methoxypyridin-3-yl)morpholino)pyrazolo[1,5-a]pyrimidine-3-carboxylic acid (Intermediate A4)

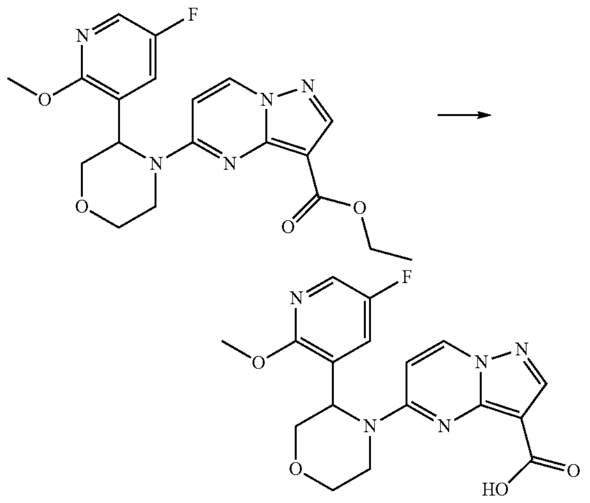

A4

According to steps a to f of intermediate preparation example 3, ethyl 5-(3-(5-fluoro methoxypyridin-3-yl)morpholinyl)pyrazolo[1,5-a]pyrimidine-3-carboxylate was prepared from 5-fluoro-2-methoxy-3-pyridinecarbaldehyde.

To a solution of ethyl 5-(3-(5-fluoro-2-methoxypyridin-3-yl)morpholinyl)pyrazolo[1,5-a]pyrimidine-3-carboxylate (5.00 g, 12.46 mmol) in absolute ethanol (50 mL) was added an aqueous solution (50 mL) of LiOH (2.091 g, 49.827 mmol), and the mixture was reacted at 75° C. overnight. The reaction system was cooled to room temperature and concentrated under reduced pressure. The aqueous phase was adjusted to pH=2 to 3 with 1 N aqueous hydrochloric acid solution and extracted with EA (3×50 mL). The organic phases were combined, washed with water (50 mL) and brine (50 mL), then dried over anhydrous $Na_2SO_4$, filtered, concentrated under reduced pressure. The residue was purified by column chromatography (PE:EA=4:1 to 1:1, v/v) to give 5-(3-(5-fluoro-2-methoxypyridin-3-yl)morpholino)pyrazolo[1,5-a]pyrimidine-3-carboxylic acid (4.277 g, 92%). (ES, m/z): 374.02[M+H]$^+$.

Intermediate Preparation Example 5: (R)—S-(2-(2,5-difluorophenyl)pyrrolidin-1-yl)-N-(4-(piperazin-1-yl)phenyl)pyrazolo[1,5-a]pyrimidine-3-carboxamide (Intermediate A5)

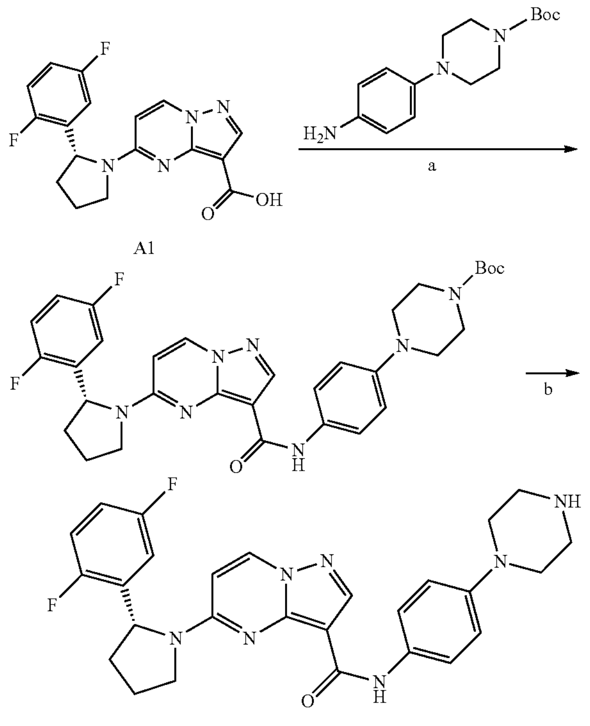

A1

A5

Step a: 1-Boc-4-(4-aminophenyl)piperazine (850 mg, 3.067 mmol) was added into a solution of (R)-5-(2-(2,5-difluorophenyl)pyrrolidin-1-yl)pyrazolo[1,5-a]pyrimidine-3-carboxylic acid (880 mg, 2.556 mmol) and TBTU (985 mg, 3.067 mmol) in anhydrous DMF (10 mL), followed by dropwise addition of DIPEA (991 mg, 7.668 mmol) at 0° C. The reaction system was reacted at room temperature overnight. The reaction liquid was added with water (50 mL), mixed and stirred. A solid was precipitated. The mixture was filtered under reduced pressure to obtain a filter cake which was dried in a vacuum oven to give (R)-tert-butyl 4-(4-(5-(2-(2,5-difluorophenyl)pyrrolidin-1-yl)pyrazolo[1,5-a]pyrimidine-3-carboxamido)phenyl)piperazine-1-carboxylate (1.450 g, 94%). (ES, m/z): 604.52[M+H]$^+$.

Step b: to (R)-tert-butyl 4-(4-(5-(2-(2,5-difluorophenyl)pyrrolidin-1-yl)pyrazolo[1,5-a]pyrimidine-3-carboxamido)phenyl)piperazine-1-carboxylate (1.45 g, 2.402 mmol) were added DCM and $CF_3COOH$ (12 mL, 3/1, v/v), and the reaction system was stirred at room temperature for 2.5 h, and concentrated under reduced pressure. The residue was added with water (12 mL) and EA (6 mL), followed by addition of aqueous ammonia to adjust the pH=9. A solid was precipitated by stirring. The mixture was filtered under reduced pressure to obtain a filter cake which was rinsed with a small amount of water, dried and weighed to give (R)—S-(2-(2,5-difluorophenyl)pyrrolidin-1-yl)-N-(4-(piperazin yl)phenyl)pyrazolo[1,5-a]pyrimidine-3-carboxamide (999 mg). (ES, m/z): 504.13 [M+H]$^+$.

Intermediate Preparation Examples 5a and 6 to 9

Referring to the process steps of the intermediate preparation example 5, the intermediates A5a and A6 to A9 were prepared by adopting the following corresponding starting materials and preparation methods:

| Intermediate preparation example Nos. | Starting materials | Intermediate structure and Nos. | Characterization data [M + H]$^+$ |
|---|---|---|---|
| 5a | 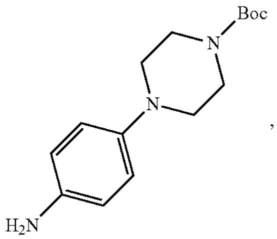 , and intermediate A1a | 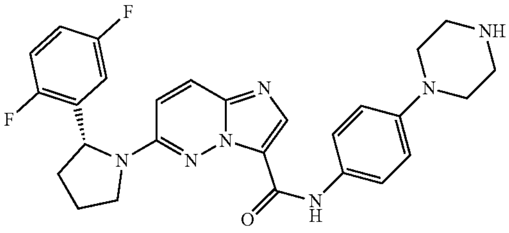 A5a | 504.12 |
| 6 | 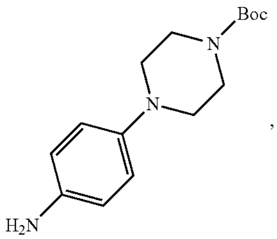 , and intermediate A1 | 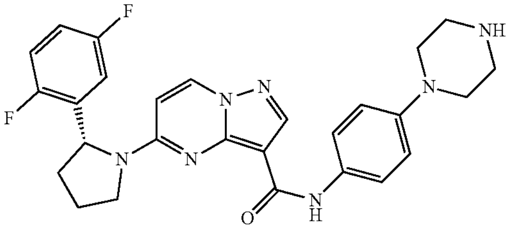 A6 | 503.13 |

-continued
| Intermediate preparation example Nos. | Starting materials | Intermediate structure and Nos. | Characterization data [M + H]$^+$ |
|---|---|---|---|
| 7 | 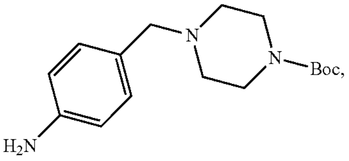 , and intermediate A1 | 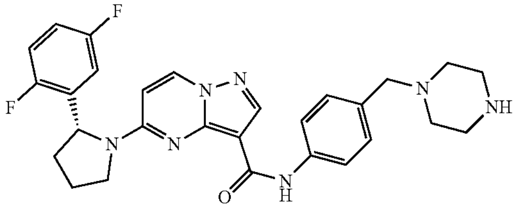 A7 | 518.21 |
| 8 | 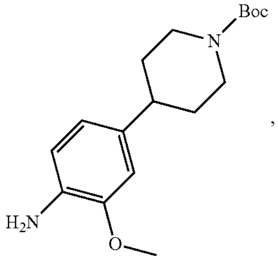 , and intermediate A1 | 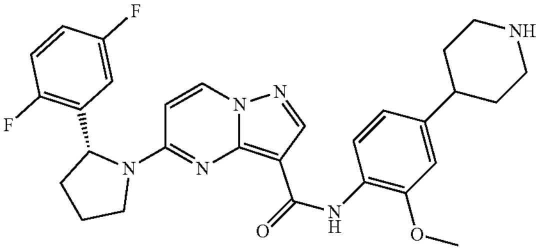 A8 | 533.21 |
| 9 | 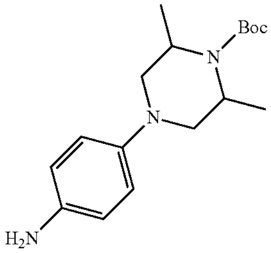 , and intermediate A1 | 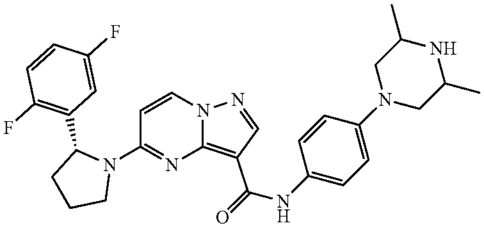 A9 | 532.21 |
Intermediate Preparation Example 10: 5-((2R,4S)-2-(2,5-difluorophenyl)-4-fluoropyrrolidin-1-yl)-N-(4-(piperazin-1-yl)phenyl)pyrazolo[1,5-a]pyrimidine-3-carboxamide (Intermediate A10)
(A10)
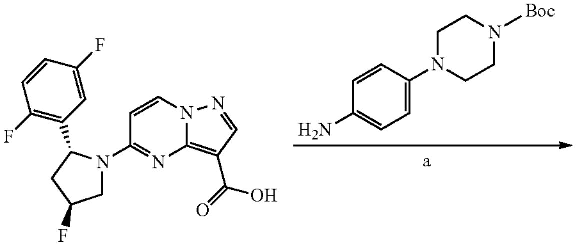
-continued
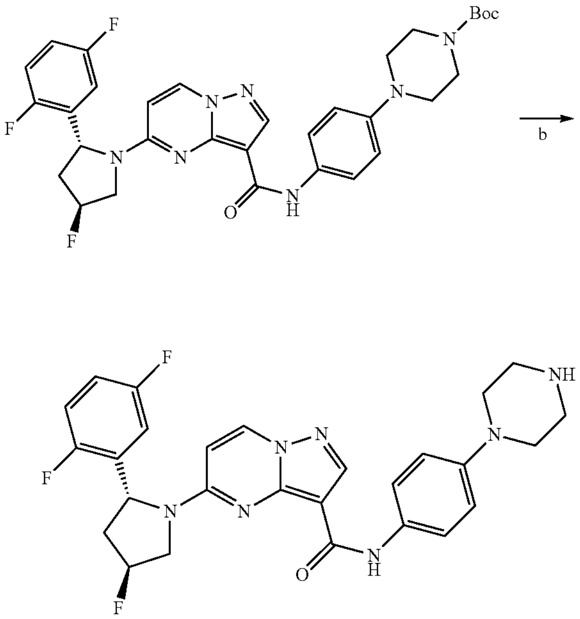

Step a: 1-Boc-4-(4-aminophenyl)piperazine (918 mg, 3.312 mmol) was added into a solution of 5-((2R,4S)-2-(2,5-difluorophenyl)-4-fluoropyrrolidin-1-yl)pyrazolo[1,5-a]pyrimidine-3-carboxylic acid (Intermediate A2, 1000 mg, 2.76 mmol) and TBTU (1063 mg, 3.312 mmol) in anhydrous DMF (10 mL), followed by dropwise addition of DIPEA (1284 mg, 9.936 mmol) at 0° C.; and the reaction system was reacted at room temperature overnight. The reaction liquid was added with water (50 mL), mixed and stirred. A solid was precipitated. The mixture was filtered under reduced pressure to obtain a filter cake which was dried in a vacuum oven to give tert-butyl 4-(4-(5-((2R,4S)-2-(2,5-difluorophenyl)-4-fluoropyrrolidin-1-yl)pyrazolo[1,5-a]pyrimidine-3-carboxamido)phenylpiperazine-1-carboxylate (1320 mg, 77%). (ES, m/z): 622.09[M+H]$^+$.

Step b: to tert-butyl 4-(4-(5-((2R,4S)-2-(2,5-difluorophenyl)-4-fluoropyrrolidin-1-yl)pyrazolo[1,5-a]pyrimidine-3-carboxamido)phenylpiperazine-1-carboxylate (1.320 g, 2.125 mmol) were added DCM and $CF_3COOH$ (12 mL, 3/1, v/v); and the reaction system was stirred at room temperature for 4 h, and concentrated under reduced pressure. The residue was added with water (80 mL) and EA (10 mL), followed by addition of aqueous ammonia to adjust the pH=9. A solid was precipitated by stirring. The mixture was filtered under reduced pressure to obtain a filter cake which was rinsed with a small amount of water, dried and weighed to give 5-((2R,4S)-2-(2,5-difluorophenyl) fluoropyrrolidin-1-yl)-N-(4-(piperazin-1-yl)phenyl)pyrazolo[1,5-a]pyrimidine-3-carboxamide (907 mg, 82%), (ES, m/z): 522.09 [M+H]$^+$.

Intermediate Preparation Example 10a

Referring to the process steps of the intermediate preparation example 10, the intermediate A10a was prepared by adopting the following corresponding starting materials and preparation methods:

Intermediate Preparation Example 11: 5-((2R,4S)-2-(2,5-difluorophenyl)-4-fluoropyrrolidin-1-yl)-N-(4-(piperidin-4-yl)phenyl)pyrazolo[1,5-a]pyrimidine-3-carboxamide (Intermediate A11)

(A11)

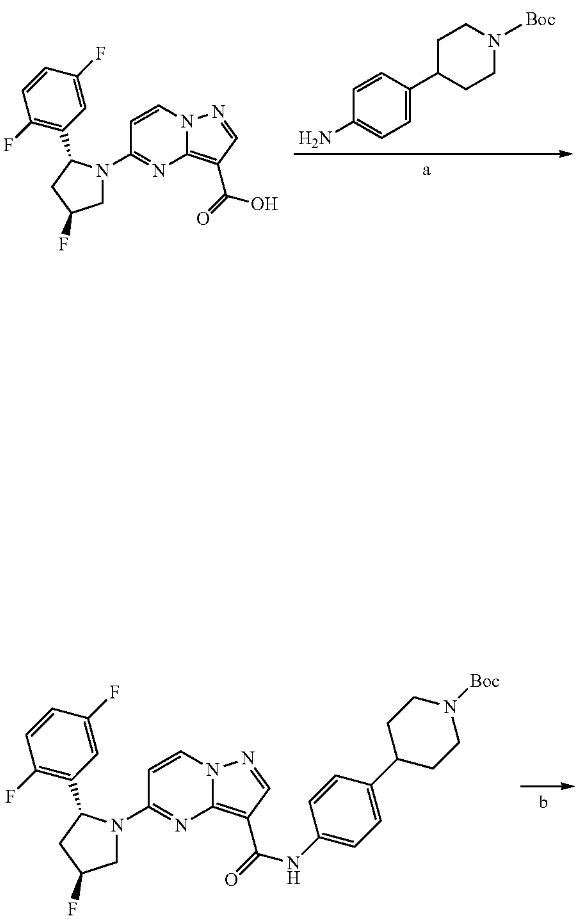

| Intermediate preparation example Nos. | Starting materials | | Intermediate structure and Nos. | Characterization data (ES, m/z): [M + H]$^+$ |
|---|---|---|---|---|
| 10a | 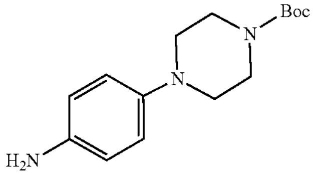 intermediate A2a | , and | 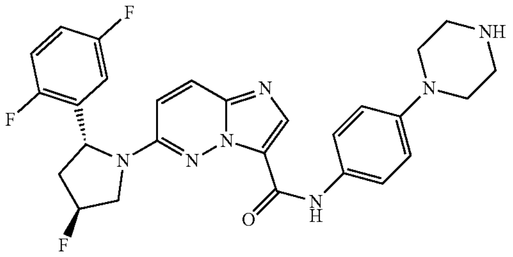 A10a | 522.12 |

-continued

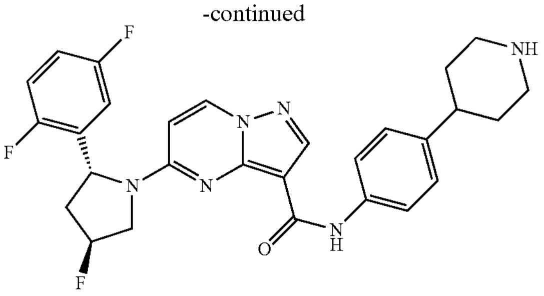

Step a: 1-Boc-4-(4-aminophenyl)piperidine (458 mg, 1.656 mmol) was added into a solution of 5-((2R,4S)-2-(2,5-difluorophenyl)-4-fluoropyrrolidin-1-yl)pyrazolo[1,5-a]pyrimidine-3-carboxylic acid (Intermediate A2, 500 mg, 1.380 mmol) and TBTU (532 mg, 1.656 mmol) in anhydrous DMF (5 mL), followed by dropwise addition of DIPEA (535 mg, 4.140 mmol) at 0° C.; and the reaction system was reacted at room temperature for 18 h overnight. The reaction liquid was added with water (50 mL), mixed and stirred. A solid was precipitated. The mixture was filtered under reduced pressure to obtain a filter cake which was dried in a vacuum oven to give tert-butyl 4-(4-(5-((2R,4S)-2-(2,5-difluorophenyl)-4-fluoropyrrolidin-1-yl)pyrazolo[1,5-a]pyrimidine carboxamido)phenylpiperidine-1-carboxylate (627 mg, 73%). (ES, m/z): 621.15[M+H]+.

Step b: to tert-butyl 4-(4-(5-((2R,4S)-2-(2,5-difluorophenyl)-4-fluoropyrrolidin-1-yl)pyrazolo[1,5-a]pyrimidine-3-carboxamido)phenylpiperidine-1-carboxylate (627 mg, 1.101 mmol) were added DCM and $CF_3COOH$ (8 mL, 3/1, v/v), and the reaction liquid was stirred at room temperature for 4 h, and concentrated under reduced pressure. The residue was added with water (80 mL) and EA (50 mL), followed by addition of aqueous ammonia to adjust the pH=9. The aqueous phase was extracted with EA (55 mL×2), and the combined extracted phase was washed with $H_2O$ (20 mL) and brine (20 mL), dried over anhydrous sodium sulfate, and filtered. The filtrate was concentrated under reduced pressure to obtain a residue, and the residue was purified with silica gel column chromatography. Specifically, the eluent was collected by 10% (v/v) MeOH-DCM after the less polar impurities were washed out with 3% (v/v) MeOH-DCM, and the eluent was concentrated to give 5-((2R,4S)-2-(2,5-difluorophenyl)-4-fluoropyrrolidin-1-yl)-N-(4-(piperidin-4-yl)phenyl)pyrazolo[1,5-a]pyrimidine-3-carboxamide (437 mg, 76%). (ES, m/z): 521.14 $[M+H]^+$.

Intermediate Preparation Examples 11a and 12

Referring to the process steps of the intermediate preparation example 11, the intermediates A11a and A12 were prepared by adopting the following corresponding starting materials and preparation methods:

| Intermediate preparation example Nos. | Starting materials | Intermediate structure and Nos. | Character-ization data $[M + H]^+$ |
|---|---|---|---|
| 11a | 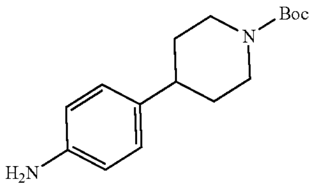 , and<br>intermediate A2a | 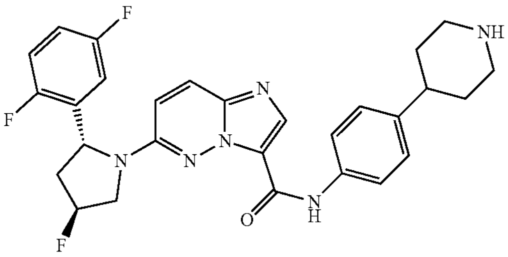<br>A11a | 521.14 |
| 12 | 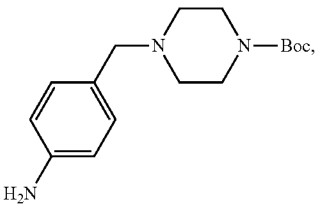 , and<br>intermediate A2 | 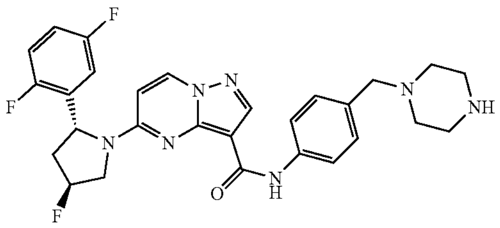<br>A12 | 536.12 |

Intermediate Preparation Example 13: 5-(3-(2,5-difluorophenyl)morpholinyl)-N-(4-(piperazin-1-yl)phenyl)pyrazolo[1,5-a]pyrimidine-3-carboxamide (Intermediate A13)

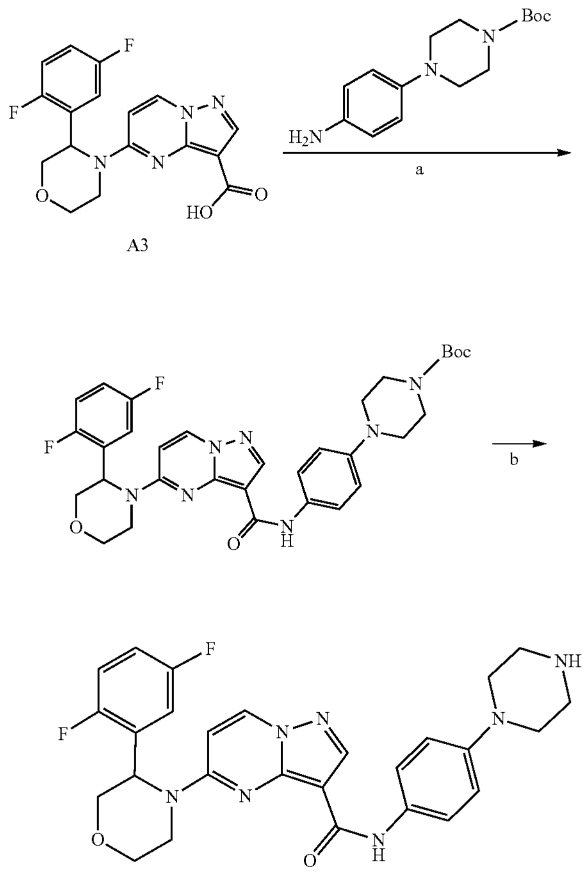

A3

A13

Step a: under nitrogen atmosphere, 1-Boc-4-(4-aminophenyl)piperazine (3.812 g, 13.756 mmol) was added into a solution of 5-(3-(2,5-difluorophenyl)morpholino)pyrazolo[1,5-a]pyrimidine-3-carboxylic acid (4.127 g, 11.46 mmol) and TBTU (4.417 g, 13.756 mmol) in anhydrous DMF (20 mL), followed by dropwise addition of DIPEA (4.441 g, 34.362 mmol) at 0° C., and the reaction system was reacted at room temperature overnight. The reaction liquid was added with EA (100 mL) and water (100 mL), mixed and stirred, and separated. The aqueous phase was extracted with EA (2×50 mL). The organic phases were combined, washed with water (2×50 mL) and brine (50 mL), then dried over anhydrous $Na_2SO_4$ and filtered. The solvent was concentrated under reduced pressure, and the resulting residue was purified by column chromatography (PE:EA=80:1 to 60:1, v/v) to give tert-butyl 4-(4-(5-(3-(2,5-difluorophenyl)morpholino)pyrazolo [1,5-a]pyrimidine-3-carboxamido)phenyl tert-butylpiperazine-1-carboxylate (3.924 g, 55.3%). (ES, m/z): 620.49$[M+H]^+$.

Step b: to a solution of tert-butyl 4-(4-(5-(3-(2,5-difluorophenyl)morpholino)pyrazolo[1,5-a]pyrimidine-3-carboxamide)phenyl tert-butylpiperazine-1-carboxylate (3.924 g, 6.332 mmol) in DCM (30 mL) was added $CF_3COOH$ (10 mL), and the reaction system was stirred at room temperature for 4 h, and concentrated under reduced pressure. The residue was added with water (100 mL) and EA (100 mL), followed by addition of aqueous ammonia to adjust the pH=9, and separated. The aqueous phase was extracted with EA (2×50 mL). The organic phases were combined, washed with water (100 mL) and brine (50 mL), then dried over anhydrous sodium sulfate, filtered, and concentrated under reduced pressure. The residue was purified by column chromatography ($CH_2Cl_2$:$CH_3OH$=50:1 to 10:1, v/v) to give 5-(3-(2,5-difluorophenyl)morpholinyl)-N-(4-(piperazin yl)phenyl)pyrazolo[1,5-a]pyrimidine-3-carboxamide (2.978 g, 90.5%). (ES, m/z): 520.11 $[M+H]^+$.

Intermediate Preparation Example 14

Referring to the process steps of the intermediate preparation example 13, the intermediate A14 was prepared by adopting the following corresponding starting materials and preparation methods:

| Intermediate preparation example Nos. | Starting materials | Intermediate structure and Nos. | Characterization data $[M + H]^+$ |
|---|---|---|---|
| 14 | 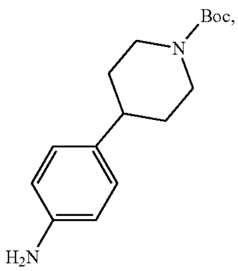 and intermediate A3 | 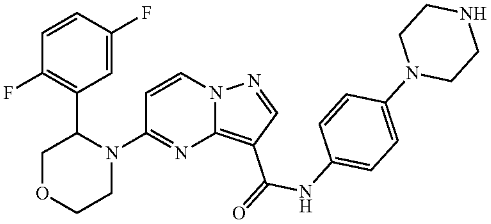 A14 | 519.12 |

Intermediate Preparation Example 15: 5-(3-(5-fluoro-2-methoxypyridin-3-yl)morpholinyl)-N-(4-(piperazin-1-yl)phenyl)pyrazolo[1,5-a]pyrimidine-3-carboxamide (Intermediate A15)

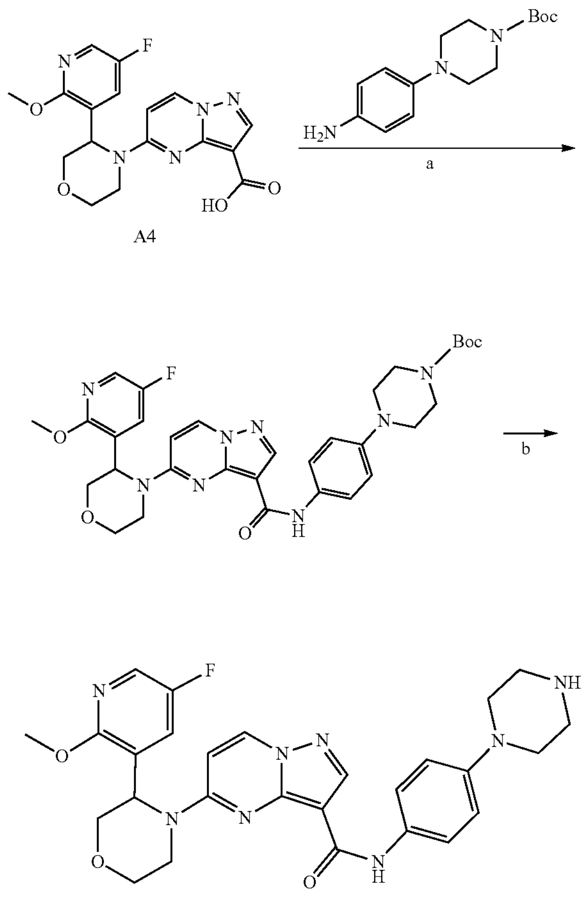

A4

A15

Step a: under nitrogen atmosphere, 1-Boc-4-(4-aminophenyl)piperazine (3.813 g, 13.747 mmol) was added into a solution of 5-(3-(5-fluoro-2-methoxypyridin-3-yl)morpholino)pyrazolo[1,5-a]pyrimidine-3-carboxylic acid (4.277 g, 11.46 mmol) and TBTU (4.414 g, 13.747 mmol) in anhydrous DMF (20 mL), followed by dropwise addition of DIPEA (4.441 g, 34.368 mmol) at 0° C., and the reaction system was reacted at room temperature overnight. The reaction liquid was added with EA (100 mL) and water (100 mL), mixed and stirred, and separated. The aqueous phase was extracted with EA (2×50 mL). The organic phases were combined, washed with water (2×50 mL) and brine (50 mL), then dried over anhydrous $Na_2SO_4$, filtered, concentrated under reduced pressure. The resulting residue was purified by column chromatography (PE:EA=100:1 to 50:1, v/v) to give tert-butyl 4-(4-(5-(3-(5-fluoro-2-methoxypyridin-3-yl)morpholino)pyrazolo [1,5-a]pyrimidine carboxamido)phenyl)piperazine-1-carboxylate (4.736 g, 65.3%). (ES, m/z): 633.09$[M+H]^+$.

Step b: to a solution of tert-butyl 4-(4-(5-(3-(5-fluoro-2-methoxypyridin yl)morpholino)pyrazolo[1,5-a]pyrimidine-3-carboxamido)phenyl)piperazine-1-carboxylate (4.736 g, 7.485 mmol) in DCM (30 mL) was added $CF_3COOH$ (10 mL), and the reaction system was stirred at room temperature for 4 h, and concentrated under reduced pressure. The residue was added with water (100 mL) and EA (100 mL), followed by addition of aqueous ammonia to adjust the pH=9, and separated. The aqueous phase was extracted with EA (2×50 mL). The organic phases were combined, washed with water (100 mL) and brine (50 mL), then dried over anhydrous sodium sulfate, filtered, and concentrated under reduced pressure. The resulting residue was purified by column chromatography ($CH_2Cl_2$:$CH_3OH$=50:1 to 10:1, v/v) to give 5-(3-(5-fluoro-2-methoxypyridin-3-yl)morpholinyl)-N-(4-(piperazin-1-yl)phenyl)pyrazolo [1,5-a]pyrimidine-3-carboxamide (3.685 g, 92.5%). (ES, m/z): 533.10 $[M+H]^+$.

Intermediate Preparation Example 16

Referring to the process steps of the intermediate preparation example 15, the intermediate A16 was prepared by adopting the following corresponding starting materials and preparation methods:

| Intermediate preparation example Nos. | Starting materials | Intermediate structure and Nos. | Characterization data $[M + H]^+$ |
|---|---|---|---|
| 16 | 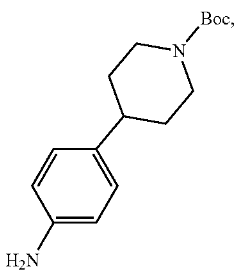 and intermediate A4 | 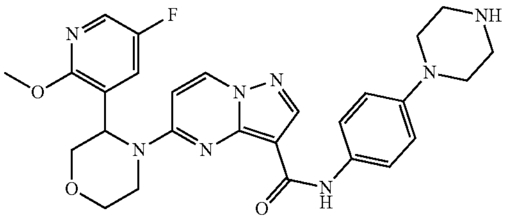 A16 | 532.19 |

Intermediate Preparation Example 17: $N^1$-(oxetan-3-yl)benzene-1,4-diamine (Intermediate B1)

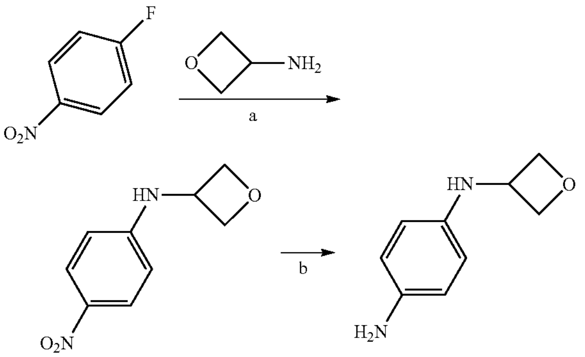

B1

Step a: 3-oxetamine (124 mg, 1.701 mmol) was added into a solution of p-fluoronitrobenzene (200 mg, 1.417 mmol) in DMSO (3 mL), followed by the addition of DIPEA (366 mg, 2.834 mmol). The reaction system was stirred at 120° C. for 5 h, added with water (20 mL), and stirred to precipitate a large amount of solid, which was then filtered under reduced pressure to obtain a filter cake N-(4-nitrophenyl)oxetan-3-amine (268 mg, 97%). (ES, m/z): 195.01 $[M+H]^+$.

Step b: the filter cake N-(4-nitrophenyl)oxetan-3-amine (268 mg, 1.380 mmol) obtained in the previous step and methanol (15 mL) were added into a reaction flask. The reaction mixture was added with 10% Pd/C, replaced with $H_2$ and stirred for 4 h. Pd/C was removed by suction filtertion, and the filtrate was concentrated under reduced pressure to give $N^1$-(oxetan-3-yl)benzene-1,4-diamine as a solid (110 mg). (ES, m/z): $164.92[M+H]^+$.

Intermediate Preparation Examples 18 to 24

Referring to the process steps of the intermediate preparation example 17, the intermediates B2 to B8 were prepared by adopting the following corresponding starting materials, p-fluoronitrobenzene and preparation methods:

| Intermediate preparation example Nos. | Starting materials | Intermediate structure and Nos. | Characterization data $[M + H]^+$ |
|---|---|---|---|
| 18 | 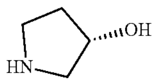 | 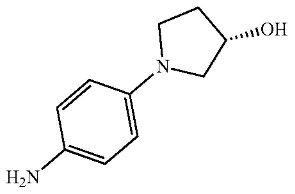 B2 | 179.12 |
| 19 | 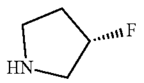 | 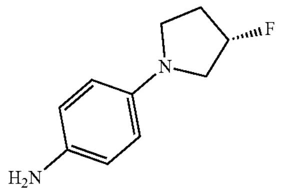 B3 | 181.11 |
| 20 | 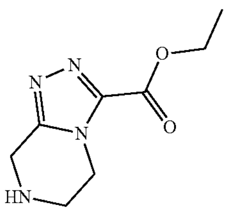 | 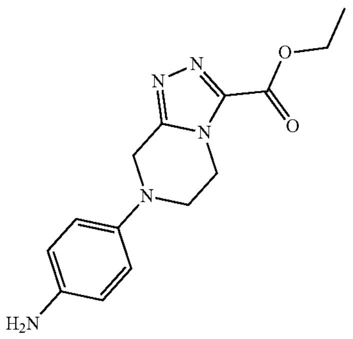 B4 | 287.93 |

-continued
| Intermediate preparation example Nos. | Starting materials | Intermediate structure and Nos. | Characterization data [M + H]$^+$ |
|---|---|---|---|
| 21 | 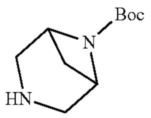 | 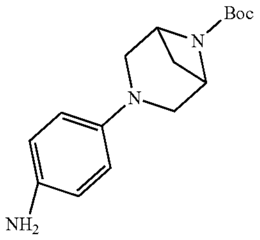 B5 | 290.27 |
| 22 | 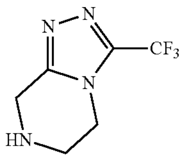 [SMILES: FC(F)(F)c1nnc2n1CCNC2] | 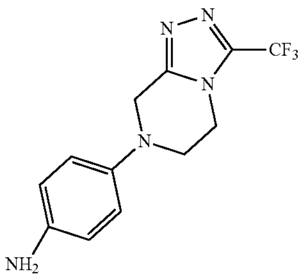 B6 | 284.15 |
| 23 | 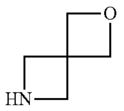 | 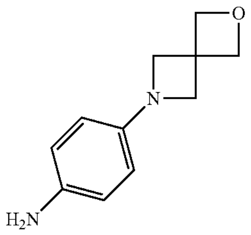 B7 | 191.14 |
| 24 | 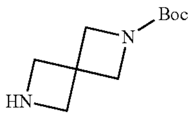 | 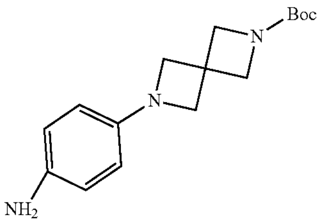 B8 | 290.25 |
Intermediate Preparation Example 25: (R)-6-(2-(2,5-difluorophenyl)pyrrolidin-1-yl)-[1,2,4]triazolo[4,3-a]pyrazine-3-carboxylic acid (Intermediate C1)
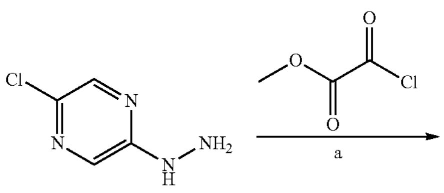
-continued
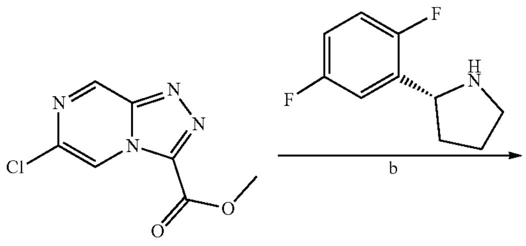

-continued

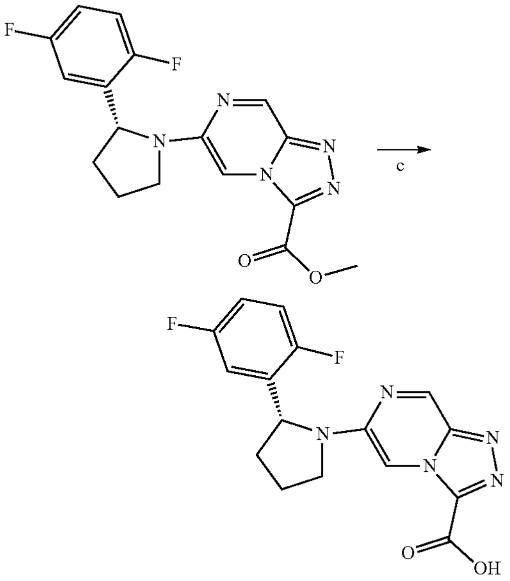

C1

Steps a to c: (R)-6-(2-(2,5-difluorophenyl)pyrrolidin-1-yl)-[1,2,4]triazolo[4,3-a]pyrazine-3-carboxylic acid was prepared by referring to the steps 1 to 3 of Example 1 in patent CN108794484B. (ES, m/z):346.02 [M+H]+.

Intermediate Preparation Example 26: 6-((2R,4S)-2-(2,5-difluorophenyl)-4-fluoropyrrolidin-1-yl)-[1,2,4]triazolo[4,3-a]pyrazine-3-carboxylic acid (Intermediate C2)

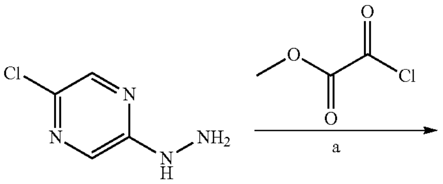

-continued

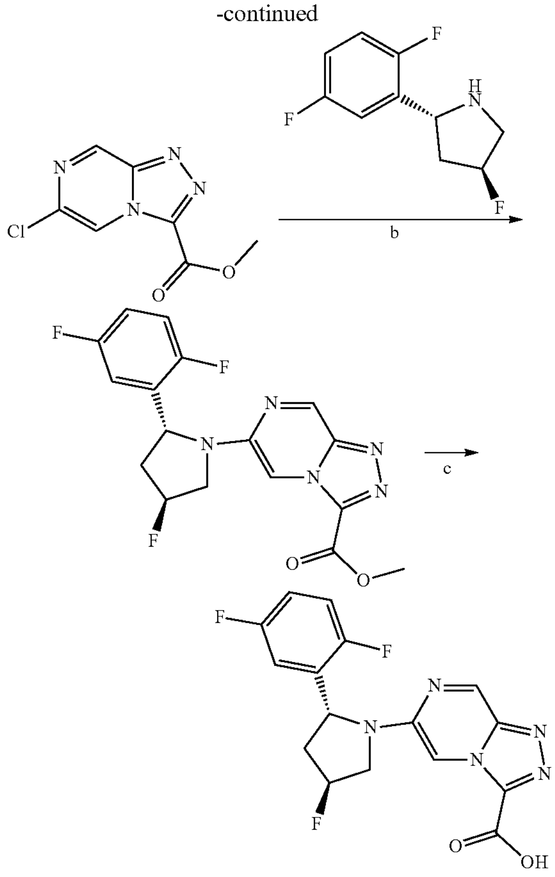

C2

Steps a to c: 6-((2R,4S)-2-(2,5-difluorophenyl)-4-fluoro-pyrrolidin-1-yl)-[1,2,4]triazolo[4,3-a]pyrazine-3-carboxylic acid was prepared by referring to the process steps of intermediate preparation example 25. (ES, m/z): 364.03 [M+H]+.

Intermediate Preparation Examples 27 to 30

Referring to the process steps of the intermediate preparation example 5, the intermediates C3 to C6 were prepared by adopting the following corresponding starting materials and preparation methods:

| Intermediate preparation example Nos. | Starting materials | Intermediate structure and Nos. | Character-ization data (ES, m/z): [M + H]+ |
|---|---|---|---|
| 27 | 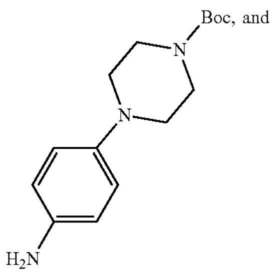 and intermediate C1 | 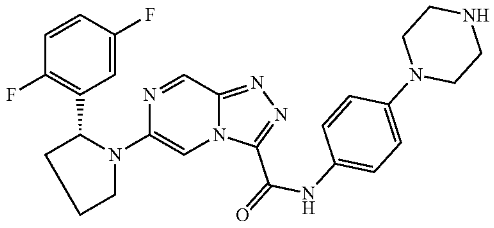 C3 | 505.12 |

-continued

| Intermediate preparation example Nos. | Starting materials | Intermediate structure and Nos. | Character-ization data (ES, m/z): [M + H]$^+$ |
|---|---|---|---|
| 28 | 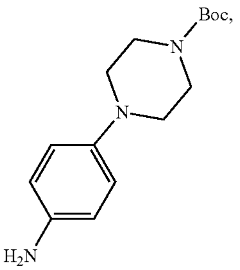 , and intermediate C2 | 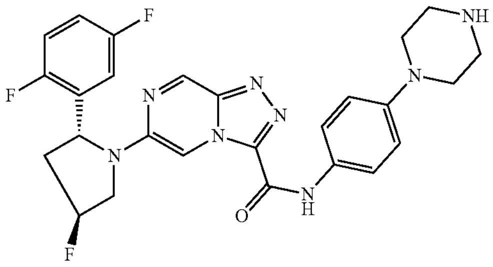 C4 | 523.11 |
| 29 | 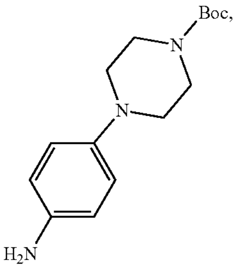 , and intermediate C1 | 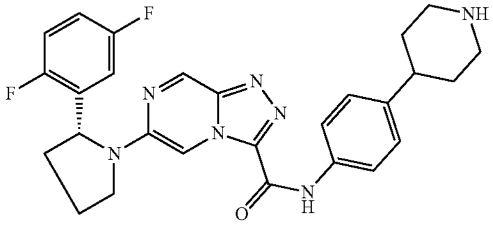 C5 | 504.13 |
| 30 | 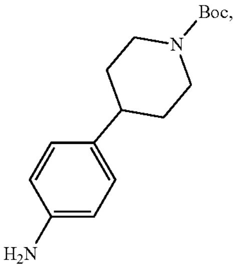 , and intermediate C2 | 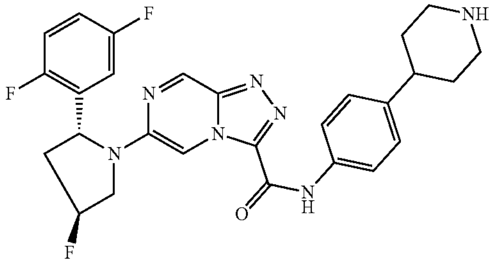 C6 | 522.10 |

The following are examples of the compounds of the present disclosure.

Example 1: (R)—S-(2-(2,5-difluorophenyl)pyrrolidin-1-yl)-N-(4-(4-(2-hydroxyacetyl)piperazin-1-yl)phenyl)pyrazolo[1,5-a]pyrimidine-3-carboxamide (Compound 1)

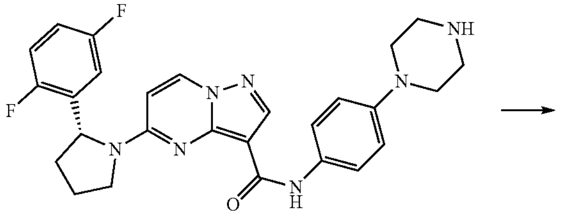

-continued

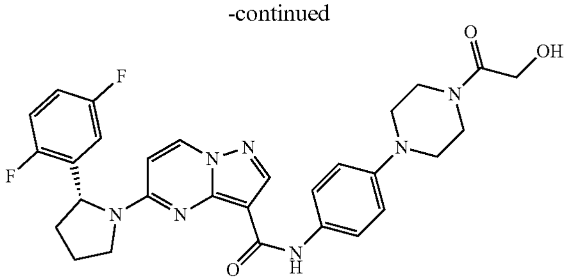

1

Hydroxyacetic acid (32 mg, 0.417 mmol) was added into a solution of (R)—S-(2-(2,5-difluorophenyl)pyrrolidin-1-yl)-N-(4-(piperazin-1-yl)phenyl)pyrazolo[1,5-a]pyrimidine-3-carboxamide (Intermediate A5, 70 mg, 0.139 mmol) and BOP (74 mg, 0.167 mmol) in anhydrous DMF (3 mL), followed by dropwise addition of DIPEA (54 mg, 0.417 mmol) at 0° C., and the reaction system was stirred at room temperature for 4 h. The reaction liquid was added with water (20 mL) for mixing, and the mixture was extracted with EA (15 mL×2). The combined organic phases were washed with $H_2O$ (20 mL) and brine (20 mL), dried over anhydrous sodium sulfate and filtered. The filtrate was concentrated under reduced pressure and the residue was purified by silica gel column chromatography. Specifically, the residue was eluted with 1% (v/v) MeOH-DCM followed by 2% (v/v) MeOH-DCM, and the eluent containing the target product was collected and concentrated to give (R)—S-(2-(2,5-difluorophenyl)pyrrolidin-1-yl)-N-(4-(4-(2-hydroxyacetyl)piperazin-1-yl)phenyl)pyrazolo[1,5-a]pyrimidine-3-carboxamide (44 mg, 56%). (ES, m/z):562.13 $[M+H]^+$.

Examples 1a, 1b and 2 to 3

Referring to the preparation process routes and operations of Example 1, compounds 1a, 1b and 2 to 3 were prepared by adopting the following materials and intermediate A5, A5a or C3 as starting materials.

| Example Nos. | Starting materials | Compound structures and Nos. | Characterization data |
|---|---|---|---|
| 1a | Hydroxyacetic acid, and intermediate A5a | 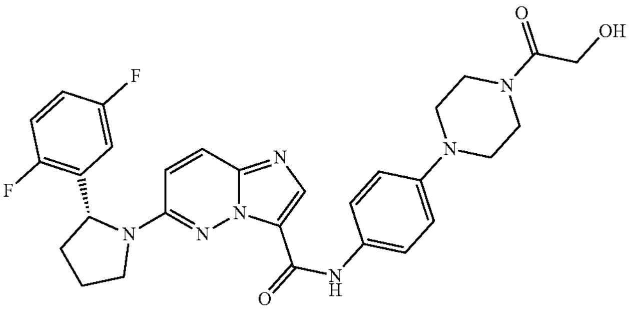 1a | 562.26 |
| 1b | Hydroxyacetic acid, and intermediate C3 | 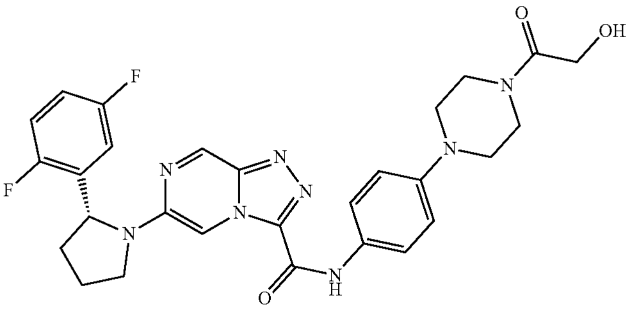 1b | 563.20 |
| 2 | 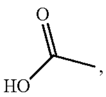 , and intermediate A5 | 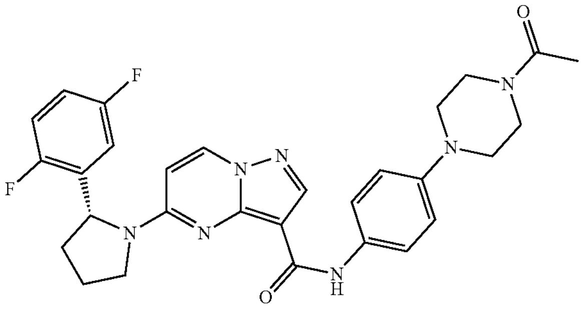 2 | (ES, m/z): 546.28 $[M + H]^+$ |

-continued

| Example Nos. | Starting materials | Compound structures and Nos. | Character-ization data |
|---|---|---|---|
| 3 | 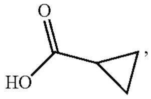, and intermediate A5 | 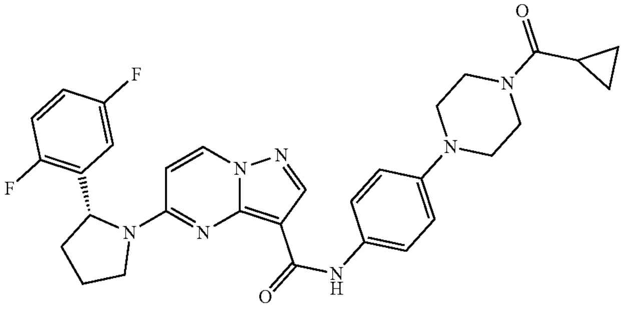 3 | (ES, m/z): 572.18 [M + H]$^+$ |

Example 4: 5-((2R,4S)-2-(2,5-difluorophenyl)-4-fluoropyrrolidin-1-yl)-N-(4-(4-(2-hydroxyacetyl)piperazin-1-yl)phenyl)pyrazolo[1,5-a]pyrimidine-3-carboxamide (Compound 4)

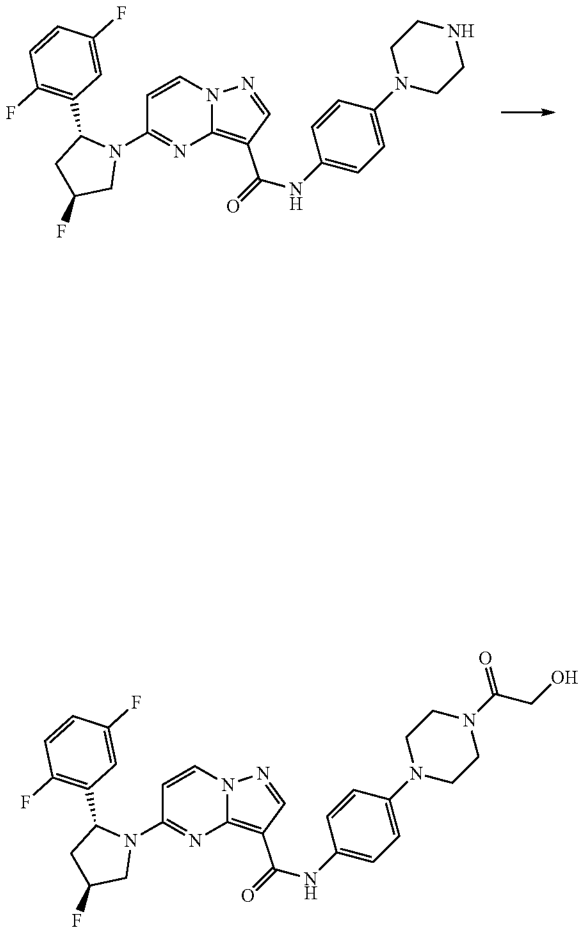

4

Hydroxyacetic acid (306 mg, 4.026 mmol) was added into a solution of 5-((2R,4S)-2-(2,5-difluorophenyl)-4-fluoropyrrolidin-1-yl)-N-(4-(piperazin-4-yl)phenyl)pyrazolo[1,5-a]pyrimidine-3-carboxamide (Intermediate A10, 700 mg, 1.342 mmol) and BOP (712 mg, 1.610 mmol) in anhydrous DMF (10 mL), followed by dropwise addition of DIPEA (520 mg, 4.026 mmol) at 0° C., and the reaction system was stirred at room temperature for 4 h. The reaction liquid was added with water (80 mL) for mixing, and the mixture was extracted with EA (55 mL×2). The combined organic phases were washed with $H_2O$ (80 mL) and brine (80 mL), respectively. Then the organic phases were dried over anhydrous sodium sulfate and filtered. The filtrate was concentrated under reduced pressure and the residue was purified by silica gel column chromatography. Specifically, the residue was eluted with 1% (v/v) MeOH-DCM followed by 2% (v/v) MeOH-DCM, and the eluent containing the target product was collected and concentrated to give 5-((2R,4S)-2-(2,5-difluorophenyl)-4-fluoropyrrolidin-1-yl)-N-(4-(4-(2-hydroxyacetyl)piperazin-1-yl)phenyl)pyrazolo[1,5-a]pyrimidine-3-carboxamide (666 mg, 86%). (ES, m/z):580.14 [M+H]$^+$. $^1$H NMR (600 MHz, DMSO-$d_6$) δ 9.810 (s, 1H), 8.906-8.723 (m, 1H), 8.283-8.229 (m, 1H), 7.623 (s, 1H), 7.343 (s, 1H), 7.210 (s, 2H), 7.061-6.842 (m, 4H), 5.711-5.495 (m, 2H), 4.631 (t, J=5.4 Hz, 1H), 4.556-4.548 (m, 1H), 4.318-4.225 (m, 1H), 4.150 (d, J=5.4 Hz, 2H), 3.637 (s, 2H), 3.513 (s, 2H), 3.124-3.106 (m, 4H), 2.957-2.912 (m, 1H).

Examples 4a to 4b, 5a, 7a to 7b and 5 to 9

According to the preparation process routes and operations of Example 4, compounds 4a to 4b, 5a, 7a to 7b and 5 to 9 were prepared by adopting the intermediate A10, A10a or C4 and the following materials as starting materials.

| Example Nos. | Starting materials | Compound structures and Nos. | Characterization data |
|---|---|---|---|
| 4a | Hydroxyacetic acid, and intermediate A10a | 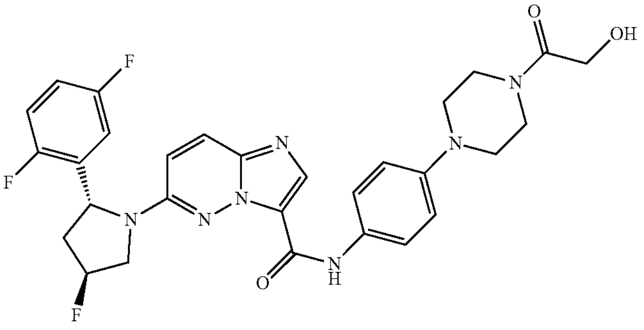 4a | 580.20 |
| 4b | Hydroxyacetic acid, and intermediate C4 | 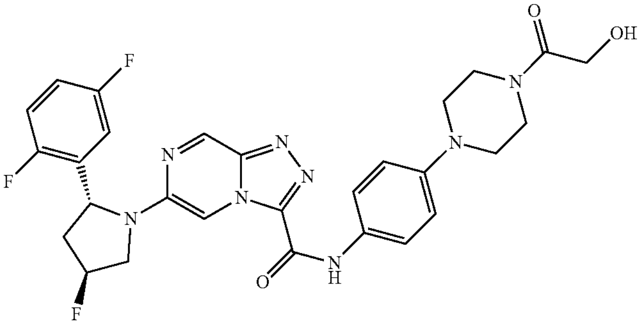 [SMILES: O=C(Nc1ccc(N2CCN(C(=O)CO)CC2)cc1)c1nnc2cnc(N3C[C@@H](F)C[C@@H]3c3cc(F)ccc3F)cn12] 4b | 581.10 |
| 5 | 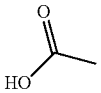 , and intermediate A10 | 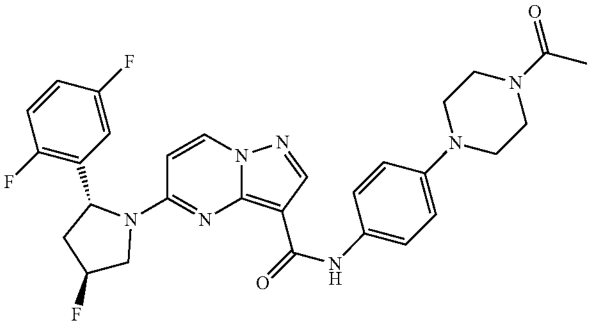 5 | (ES, m/z): 564.09 [M + H]+ |
| 5a | Acetic acid, and intermediate C4 | 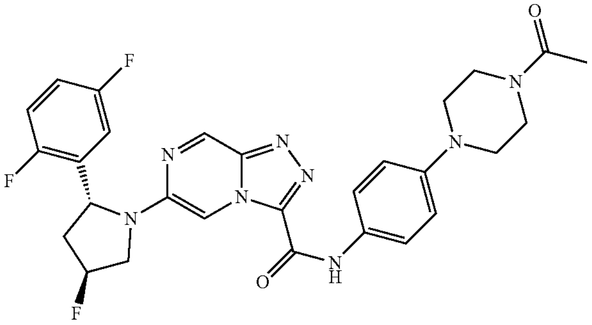 [SMILES: CC(=O)N1CCN(c2ccc(NC(=O)c3nnc4cnc(N5C[C@@H](F)C[C@@H]5c5cc(F)ccc5F)cn34)cc2)CC1] 5a | 565.20 |

-continued
| Example Nos. | Starting materials | Compound structures and Nos. | Characterization data |
| --- | --- | --- | --- |
| 6 | 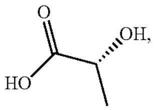, and intermediate A10 | 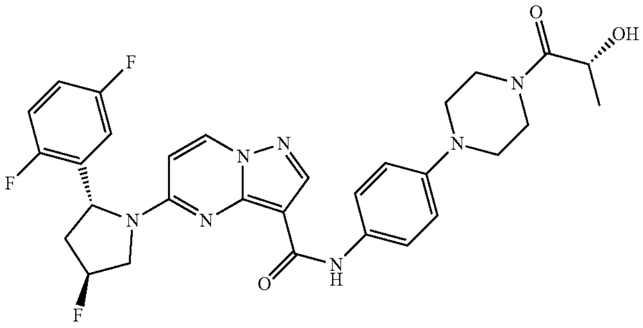 [SMILES: C[C@@H](O)C(=O)N1CCN(c2ccc(NC(=O)c3cnn4ccc(N5C[C@@H](F)C[C@@H]5c5cc(F)ccc5F)nc34)cc2)CC1] 6 | (ES, m/z). 594.47 [M + H]+ |
| 7 | 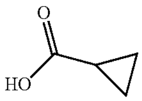, and intermediate A10 | 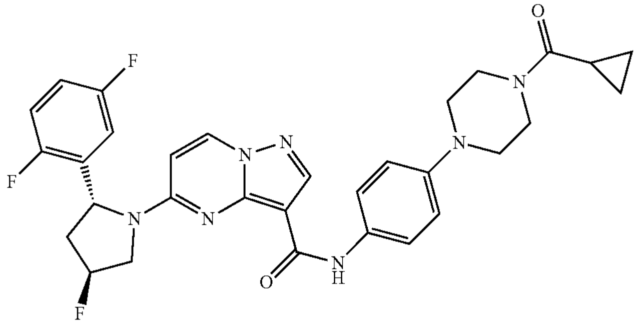 7 | (ES, m/z). 590.18 [M + H]+ |
| 7a | 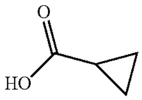, and intermediate A10a | 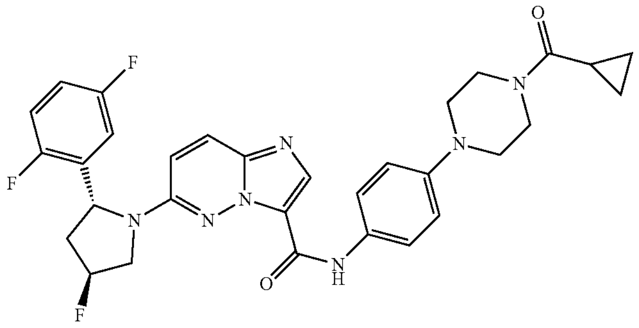 [SMILES: O=C(Nc1ccc(N2CCN(C(=O)C3CC3)CC2)cc1)c1cnc2ccc(N3C[C@@H](F)C[C@@H]3c3cc(F)ccc3F)nn12] 7a | 590.18 |
| 7b | 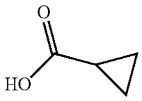, and intermediate C4 | 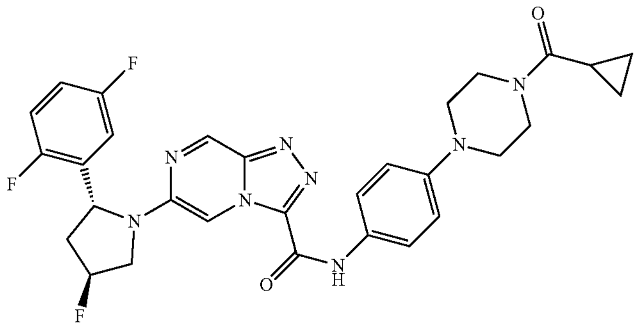 [SMILES: O=C(Nc1ccc(N2CCN(C(=O)C3CC3)CC2)cc1)c1nnc2cnc(N3C[C@@H](F)C[C@@H]3c3cc(F)ccc3F)cn12] 7b | 591.16 |

-continued

| Example Nos. | Starting materials | Compound structures and Nos. | Characterization data |
|---|---|---|---|
| 8 | 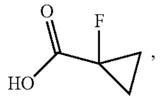 and intermediate A10 | 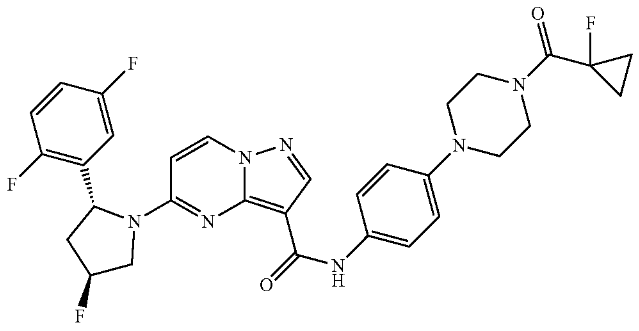 [SMILES: O=C(Nc1ccc(N2CCN(C(=O)C3(F)CC3)CC2)cc1)c1cnn2ccc(N3C[C@@H](F)C[C@@H]3c3cc(F)ccc3F)nc12] 8 | (ES, m/z): 608.18 $[M + H]^+$ |
| 9 | 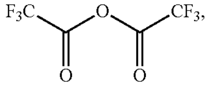 [SMILES: O=C(OC(=O)C(F)(F)F)C(F)(F)F] and intermediate A10 | 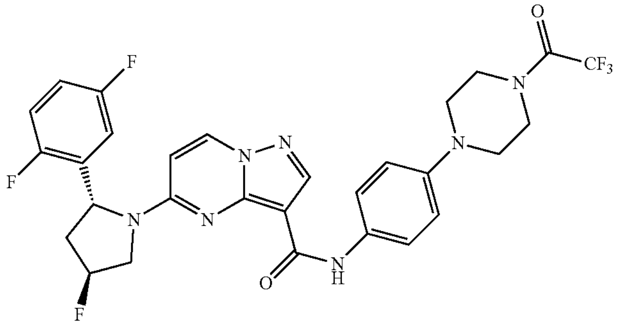 9 | (ES, m/z): 618.28 $[M + H]^+$ |

Example 10: 5-((2R,4S)-2-(2,5-difluorophenyl)-4-fluoropyrrolidin-1-yl)-N-(4-(1-(2-hydroxyacetyl)piperidin-4-yl)phenyl)pyrazolo[1,5-a]pyrimidine-3-carboxamide (Compound 10)

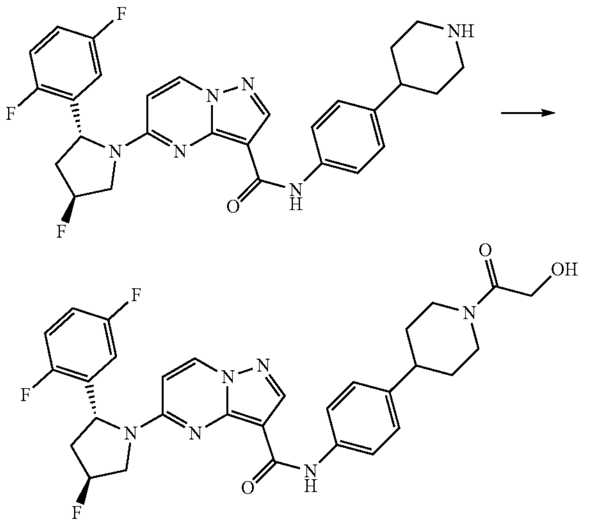

10

Hydroxyacetic acid (438 mg, 5.763 mmol) was added into a solution of 5-((2R,4S)-2-(2,5-difluorophenyl)-4-fluoropyrrolidin-1-yl)-N-(4-(piperidin-4-yl)phenyl)pyrazolo[1,5-a]pyrimidine-3-carboxamide (Intermediate A11, 1000 mg, 1.921 mmol) and BOP (1274 mg, 2.882 mmol) in anhydrous DMF (10 mL), followed by dropwise addition of DIPEA (745 mg, 5.763 mmol) at 0° C., and the reaction system was stirred at room temperature overnight. The reaction liquid was added with water (100 mL) for mixing. The mixture was extracted with EA (80 mL×2). The combined organic phases were washed with $H_2O$ (100 mL) and brine (110 mL), dried over anhydrous sodium sulfate and filtered. The filtrate was concentrated under reduced pressure, and the residue was purified by silica gel column chromatography. Specifically, the residue was eluted with 1% (v/v) MeOH-DCM followed by 2% (v/v) MeOH-DCM. The eluent containing the target product was collected and concentrated to give 5-((2R,4S)-2-(2,5-difluorophenyl)-4-fluoropyrrolidin-1-yl)-N-(4-(1-(2-hydroxyacetyl)piperidin-4-yl)phenyl)pyrazolo[1,5-a]pyrimidine-3-carboxamide (820 mg, 74%). (ES, m/z): 579.14 $[M+H]^+$. $^1H$ NMR (600 MHz, DMSO-$d_6$) δ 9.952 (s, 1H), 9.022-8.753 (m, 1H), 8.355-8.152 (m, 2H), 7.663 (s, 1H), 7.343-7.042 (m, 6H), 5.773-5.552 (m, 2H), 4.529-4.481 (m, 2H), 4.358-4.115 (m, 3H), 3.803-3.779 (m, 1H), 3.640-3.603 (m, 1H), 3.090-3.049 (m, 1H), 2.968-2.957 (m, 1H), 2.792-2.752 (m, 1H), 2.722-2.682 (m, 1H), 2.241-2.212 (m, 1H), 1.808 (s, 2H), 1.608-1.589 (m, 1H), 1.492-1.476 (m, 1H).

Examples 10a to 10b, 11a to 11b, and 11 to 17

According to the preparation process routes and operations of Example 10, compounds 10a to 10b, 11a to 11b and 11 to 17 were prepared by adopting the intermediate A11, A11a or C6 and the following materials as starting materials.

| Example Nos. | Starting materials | Compound structures and Nos. | Characterization data |
|---|---|---|---|
| 10a | Hydroxyacetic acid, and intermediate A11a | 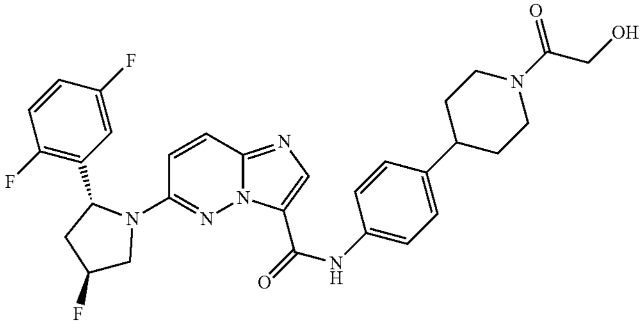 [SMILES: O=C(Nc1ccc(C2CCN(C(=O)CO)CC2)cc1)c1cnc2ccc(N3C[C@@H](F)C[C@@H]3c3cc(F)ccc3F)nn12] 10a | (ES, m/z): 579.16 [M + H]+ |
| 10b | Hydroxyacetic acid, and intermediate C6 | 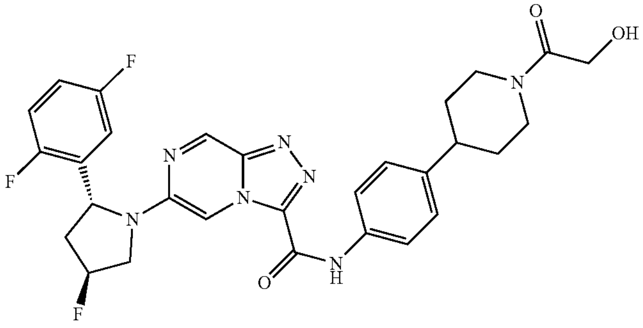 [SMILES: O=C(Nc1ccc(C2CCN(C(=O)CO)CC2)cc1)c1nnc2cnc(N3C[C@@H](F)C[C@@H]3c3cc(F)ccc3F)cn12] 10b | (ES, m/z): 580.15 [M + H]+ |
| 11 | 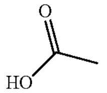 , and intermediate A11 | 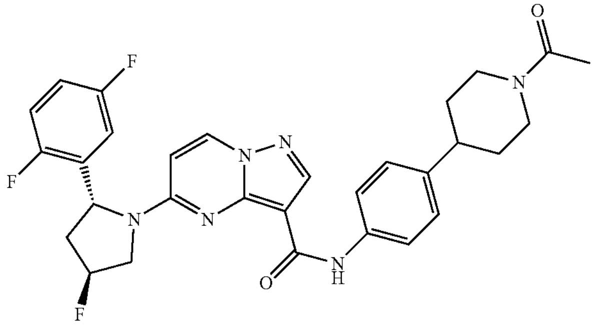 11 | (ES, m/z): 563.19 [M + H]+ |
| 11a | Acetic acid, and intermediate A11a | 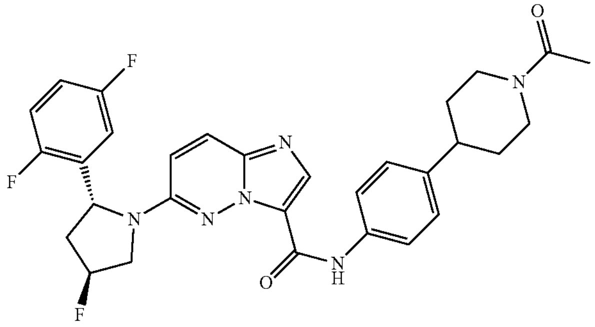 [SMILES: CC(=O)N1CCC(c2ccc(NC(=O)c3cnc4ccc(N5C[C@@H](F)C[C@@H]5c5cc(F)ccc5F)nn34)cc2)CC1] 11a | (ES, m/z): 563.16 [M + H]+ |

-continued
| Example Nos. | Starting materials | Compound structures and Nos. | Characterization data |
|---|---|---|---|
| 11b | Acetic acid, and intermediate C6 | 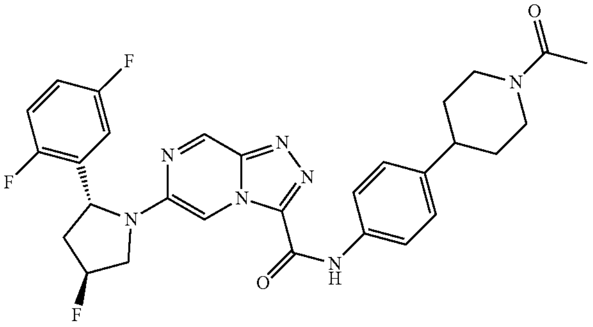 [SMILES: CC(=O)N1CCC(c2ccc(NC(=O)c3nnc4cnc(N5C[C@@H](F)C[C@@H]5c5cc(F)ccc5F)cn34)cc2)CC1]<br>11b | (ES, m/z): 564.19 [M + H]$^+$ |
| 12 | 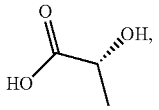<br>and intermediate A11 | 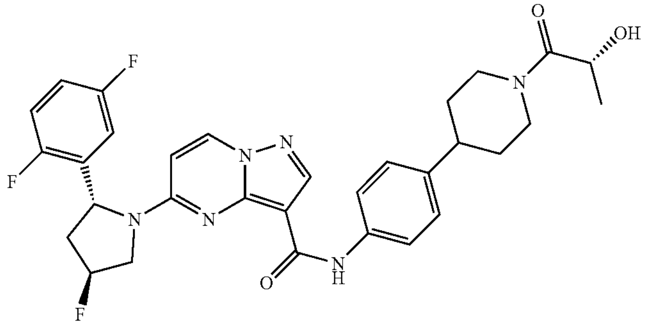<br>12 | (ES, m/z): 593.09 [M + H]$^+$ |
| 13 | 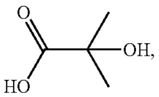<br>and intermediate A11 | 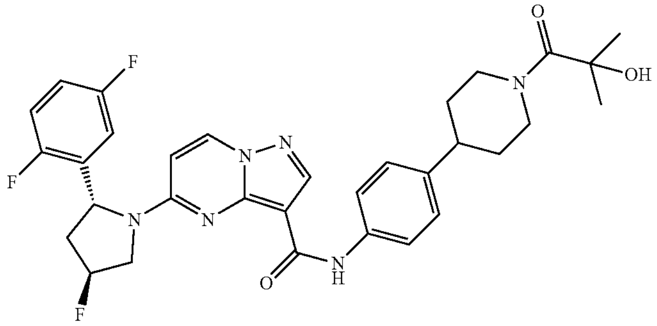 [SMILES: CC(C)(O)C(=O)N1CCC(c2ccc(NC(=O)c3cnn4ccc(N5C[C@@H](F)C[C@@H]5c5cc(F)ccc5F)nc34)cc2)CC1]<br>13 | (ES, m/z): 607.89 [M + H]$^+$ |
| 14 | 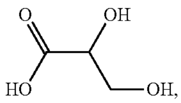<br>and intermediate A11 | 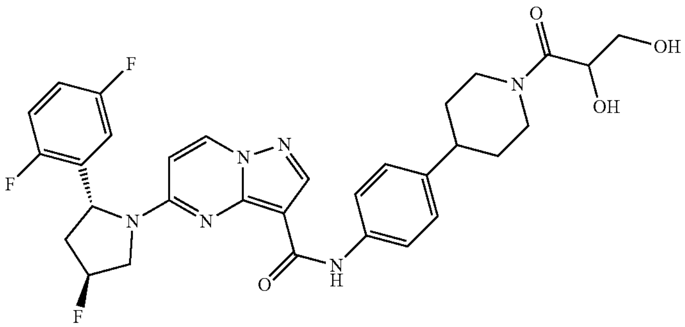 [SMILES: O=C(Nc1ccc(C2CCN(C(=O)C(O)CO)CC2)cc1)c1cnn2ccc(N3C[C@@H](F)C[C@@H]3c3cc(F)ccc3F)nc12]<br>14 | (ES, m/z): 609.14 [M + H]$^+$ |

-continued

| Example Nos. | Starting materials | Compound structures and Nos. | Characterization data |
|---|---|---|---|
| 15 | 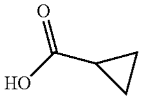 , and intermediate A11 | 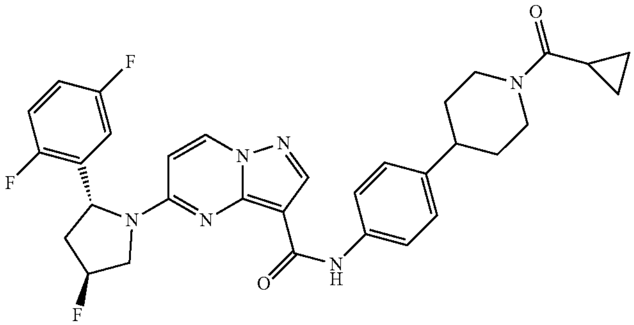 [SMILES: O=C(Nc1ccc(C2CCN(C(=O)C3CC3)CC2)cc1)c1cnn2ccc(N3C[C@@H](F)C[C@@H]3c3cc(F)ccc3F)nc12] 15 | (ES, m/z): 589.08 $[M + H]^+$ |
| 16 | 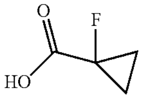 , and intermediate A11 | 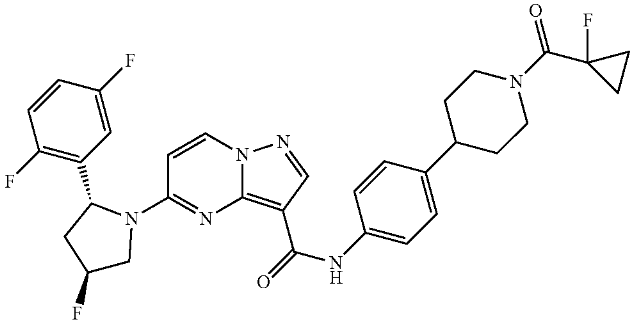 16 | (ES, m/z): 607.12 $[M + H]^+$ |
| 17 | 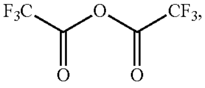 [SMILES: O=C(OC(=O)C(F)(F)F)C(F)(F)F] , and intermediate A11 | 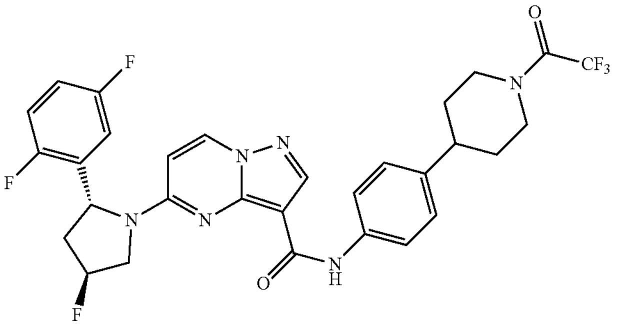 17 | (ES, m/z): 617.07 $[M + H]^+$ |

Example 18: 5-((2R,4S)-2-(2,5-difluorophenyl)-4-fluoropyrrolidin-1-yl)-N-(4-(4-(2-(2-hydroxyacetyl)piperazin-1-yl)methyl) phenyl)pyrazolo[1,5-a]pyrimidine-3-carboxamide (Compound 18)

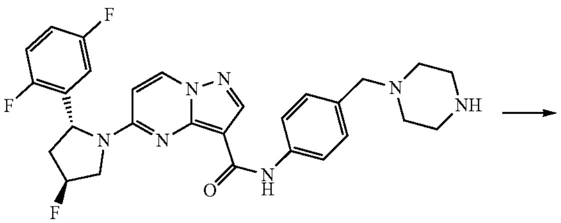

-continued

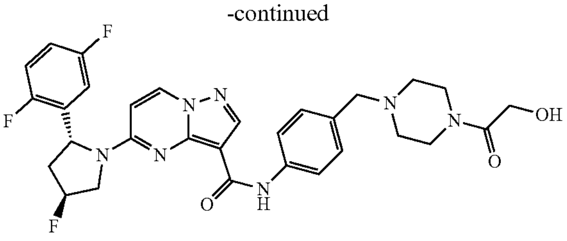

18

Hydroxyacetic acid (51 mg, 0.672 mmol) was added into a solution of 5-((2R,4S)-2-(2,5-difluorophenyl)-4-fluoropyrrolidin-1-yl)-N-(4-(piperazin-1-ylmethyl)phenyl)pyrazolo[1,5-a]pyrimidine-3-carboxamide (Intermediate A12, 120 mg, 0.224 mmol) and BOP (149 mg, 0.336 mmol) in anhydrous DMF (12 mL), followed by dropwise addition of DIPEA (87 mg, 0.672 mmol) at 0° C., and the reaction system was stirred at room temperature for 4 h. The reaction liquid was added with water (20 mL) for mixing, and the mixture was extracted with EA (10 mL×2). The combined organic phases were washed with $H_2O$ (10 mL) and brine (10 mL), dried over anhydrous sodium sulfate and filtered. The filtrate was concentrated under reduced pressure. The residue was purified by silica gel column chromatography, and specifically, the residue was eluted with 1% (v/v) MeOH-DCM followed by 2% (v/v) MeOH-DCM to give 5-((2R,4S)-2-(2,5-difluorophenyl)-4-fluoropyrrolidin yl)-N-(4-(4-(2-(2-hydroxyacetyl)piperazin-1-yl)methyl)phenyl) pyrazolo [1,5-a]pyrimidine carboxamide (30 mg, 22%). (ES, m/z): 594.12[M+H]$^+$.

Example 19: 5-((2R,4S)-2-(2,5-difluorophenyl)-4-fluoropyrrolidin-1-yl)-N-(4-(oxetan-3-ylamino)phenyl)pyrazolo[1,5-a]pyrimidine-3-carboxamide (Compound 19)

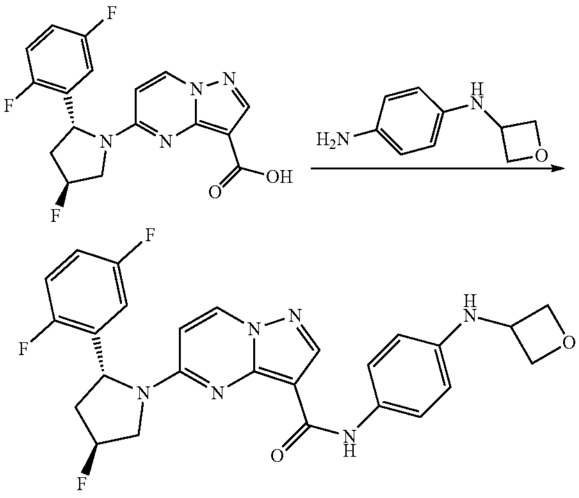

19

N$^1$-(Oxetan-3-yl)benzene-1,4-diamine (105 mg, 0.640 mmol) was added into a solution of 5-((2R,4S)-2-(2,5-difluorophenyl)-4-fluoropyrrolidin-1-yl)-N-(1,2,3,4-tetrahydroisoquinolin-7-yl)pyrazolo [1,5-a]pyrimidine-3-carboxamide (Intermediate A2, 193 mg, 0.534 mmol) and TBTU (205 mg, 0.640 mmol) in anhydrous DMF (5 mL), followed by dropwise addition of DIPEA (205 mg, 1.602 mmol) at 0° C., and the reaction system was stirred overnight at room temperature for 14 h. The reaction liquid was added with water (25 mL) for mixing, and the mixture was extracted with EA (15 mL×2). The combined organic phases were washed with $H_2O$ (20 mL) and brine (20 mL), dried over anhydrous sodium sulfate and filtered. The filtrate was concentrated under reduced pressure to obtain a residue which was separated by preparative liquid chromatography (X-Bridge C18 19*150 mm 5 μm, elution system: 5-25% aqueous acetonitrile solution for gradient elution, 0.05% $NH_4HCO_3$ for modification) to give 5-((2R,4S)-2-(2,5-difluorophenyl)-4-fluoropyrrolidin-1-yl)-N-(4-(oxetan-3-ylamino)phenyl)pyrazolo[1,5-a]pyrimidine-3-carboxamide (60 mg, 22.1%). (ES, m/z): 509.12[M+H]$^+$.

Examples 19a to 19b and 20 to 24

According to the preparation process routes and operations of Example 19, compounds 19a to 19b and 20 to 24 were prepared by adopting the following intermediates as starting materials:

| Example Nos. | Starting materials | Compound structures and Nos. | Characterization data |
|---|---|---|---|
| 19a | Intermediate A2a, and intermediate B1 | 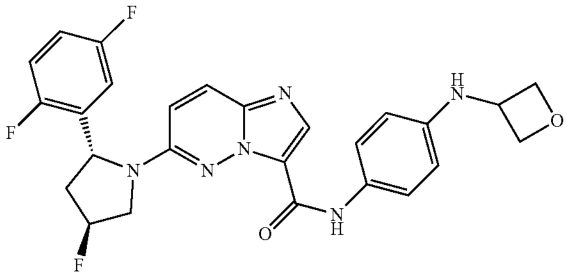 [SMILES: O=C(Nc1ccc(NC2COC2)cc1)c1cnc2ccc(N3C[C@@H](F)C[C@@H]3c3cc(F)ccc3F)nn12] 19a | 509.11 |

-continued
| Example Nos. | Starting materials | Compound structures and Nos. | Characterization data |
|---|---|---|---|
| 19b | Intermediate C2, and intermediate B1 | 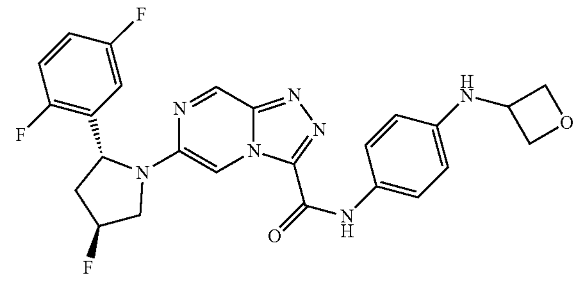 [SMILES: O=C(Nc1ccc(NC2COC2)cc1)c1nnc2cnc(N3C[C@@H](F)C[C@@H]3c3cc(F)ccc3F)cn12] 19b | 510.09 |
| 20 | Intermediate A1, and intermediate B2 | 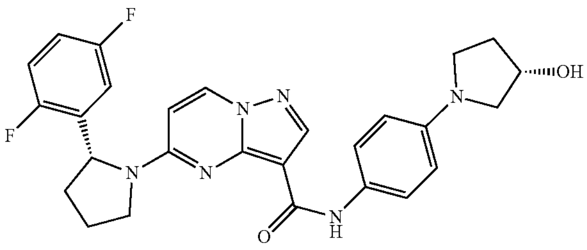 [SMILES: O=C(Nc1ccc(N2CC[C@H](O)C2)cc1)c1cnn2ccc(N3CCC[C@@H]3c3cc(F)ccc3F)nc12] 20 | (ES, m/z): 505.07 [M + H]+ |
| 21 | Intermediate A2, and intermediate B2 | 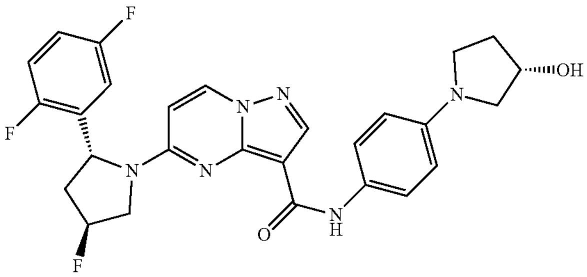 [SMILES: O=C(Nc1ccc(N2CC[C@H](O)C2)cc1)c1cnn2ccc(N3C[C@@H](F)C[C@@H]3c3cc(F)ccc3F)nc12] 21 | (ES, m/z): 523.06 [M + H]+ |
| 22 | Intermediate A2, and intermediate B3 | 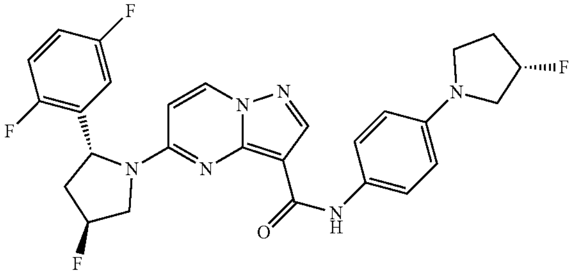 [SMILES: O=C(Nc1ccc(N2CC[C@H](F)C2)cc1)c1cnn2ccc(N3C[C@@H](F)C[C@@H]3c3cc(F)ccc3F)nc12] 22 | (ES, m/z): 525.06 [M + H]+ |

-continued

| Example Nos. | Starting materials | Compound structures and Nos. | Characterization data |
|---|---|---|---|
| 23 | Intermediate A2, and intermediate B6 | 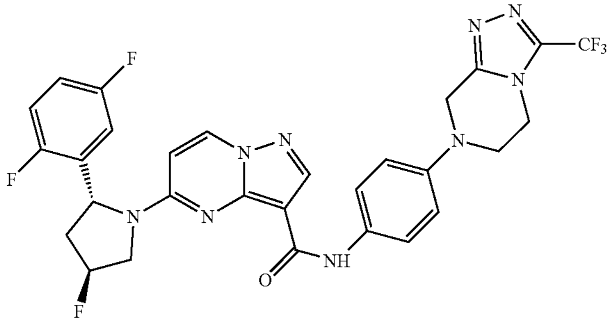 [SMILES: O=C(Nc1ccc(N2CCn3c(nnc3C(F)(F)F)C2)cc1)c1cnn2ccc(N3C[C@@H](F)C[C@@H]3c3cc(F)ccc3F)nc12] 23 | (ES, m/z): 628.11 $[M + H]^+$ |
| 24 | Intermediate A2, and intermediate B7 | 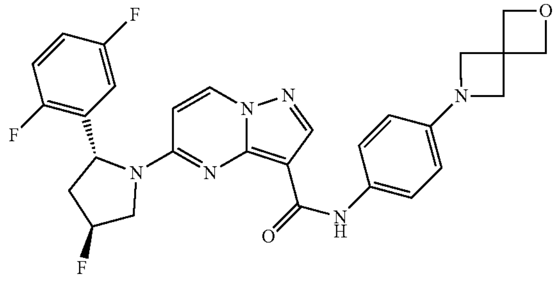 [SMILES: O=C(Nc1ccc(N2CC3(COC3)C2)cc1)c1cnn2ccc(N3C[C@@H](F)C[C@@H]3c3cc(F)ccc3F)nc12] 24 | (ES, m/z): 535.08 $[M + H]^+$ |

Example 25: 5-((2R,4S)-2-(2,5-difluorophenyl)-4-fluoropyrrolidin-1-yl)-N-(4-(6-(2-hydroxyacetyl)-3,6-diazabicyclo[3.1.1]hept-3-yl)phenyl)pyrazolo[1,5-a]pyrimidine-3-carboxamide (compound 25)

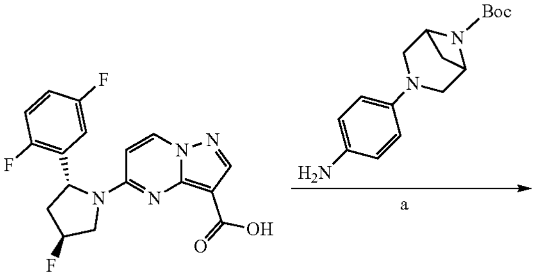

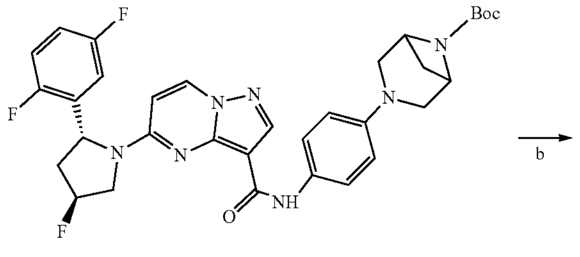

-continued

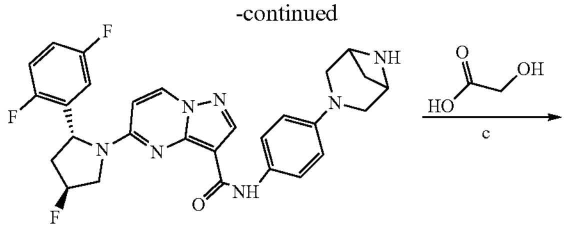

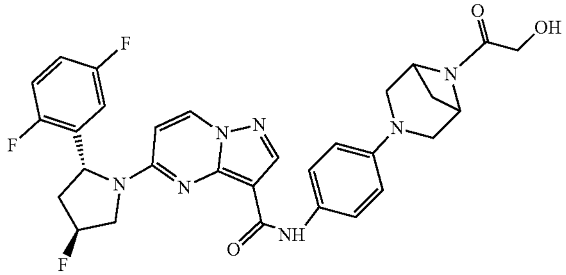

25

Step a: tert-butyl 3-(4-aminophenyl)-3,6-diazabicyclo[3.1.1]heptane-6-carboxylate (442 mg, 1.528 mmol) (Intermediate B5) was added into a solution of 5-((2R,4S)-2-(2,5-difluorophenyl)-4-fluoropyrrolidin-1-yl)pyrazolo[1,5-a]pyrimidine-3-carboxylic acid (Intermediate A2, 460 mg, 1.270 mmol) and TBTU (491 mg, 1.528 mmol) in anhydrous DMF (5 mL), followed by dropwise addition of DIPEA (494 mg, 3.819 mmol) at 0° C., and the reaction system was stirred overnight at room temperature for 14 h. The reaction liquid was added with water (100 mL), mixed and stirred. A large amount of solid was precipitated, filtered under reduced pressure and dried to give crude tert-butyl 3-(4-(5-

((2R,4S)-2-(2,5-difluorophenyl)-4-fluoropyrrolidin-1-yl) pyrazolo[1,5-a]pyrimidine formamido)phenyl)-3,6-diazabicyclo[3.1.1]heptane-6-carboxylate.

Step b: the crude tert-butyl 3-(4-(5-((2R,4S)-2-(2,5-difluorophenyl)-4-fluoropyrrolidin yl)pyrazolo[1,5-a]pyrimidine-3-formamido)phenyl)-3,6-diazabicyclo[3.1.1]heptane-6-carboxylate obtained above was dissolved in DCM (25 mL). The solution was added with $CF_3COOH$ (5 mL) and stirred at room temperature for 3 h. The reaction liquid was concentrated by rotary evaporation, and added with water for dilution, followed by addition of aqueous ammonia to adjust the pH. A solid was precipitated, subjected to suction filtration, and dried to give N-(4-(3,6-diazabicyclo[3.1.1]heptyl-3-yl)phenyl)-5-((2R,4S)-2-(2,5-difluorophenyl)-4-fluoropyrrolidin-1-yl)pyrazolo[1,5-a]pyrimidine-3-carboxamide as a solid (450 mg).

Step c: hydroxyacetic acid (35 mg, 0.450 mmol) was added into a solution of N-(4-(3,6-diazabicyclo[3.1.1]heptyl-3-yl)phenyl)-S-((2R,4S)-2-(2,5-difluorophenyl)-4-fluoropyrrolidin-1-yl)pyrazolo[1,5-a]pyrimidine-3-carboxamide (200 mg, 0.375 mmol) and TBTU (145 mg, 0.450 mmol) in anhydrous DMF (5 mL), followed by dropwise addition of DIPEA (146 mg, 1.125 mmol) at 0° C., and the reaction system was stirred at room temperature for 4 h. The reaction liquid was added with water (30 mL) for mixing. The mixture was extracted with EA (20 mL×2). The combined organic phases were washed with $H_2O$ (30 mL) and brine (40 mL), dried over anhydrous sodium sulfate and filtered, and the filtrate was concentrated under reduced pressure. The residue was purified by silica gel column chromatography, and specifically, the residue was eluted with 1% MeOH-DCM followed by 2% MeOH-DCM. The eluent containing the target product was collected and concentrated to give 5-((2R,4S)-2-(2,5-difluorophenyl)-4-fluoropyrrolidin-1-yl)-N-(4-(6-(2-hydroxyacetyl)-3,6-diazabicyclo[3.1.1]hept-3-yl)phenyl)pyrazolo[1,5-a]pyrimidine-3-carboxamide (180 mg, 81%). (ES, m/z): 592.02$[M+H]^+$.

Example 26: 5-((2R,4S)-2-(2,5-difluorophenyl)-4-fluoropyrrolidin-1-yl)-N-(4-(6-(2-hydroxyacetyl)-2,6-diazaspiro[3.3]heptane-2-yl)phenyl)pyrazolo[1,5-a]pyrimidine-3-carboxamide (Compound 26)

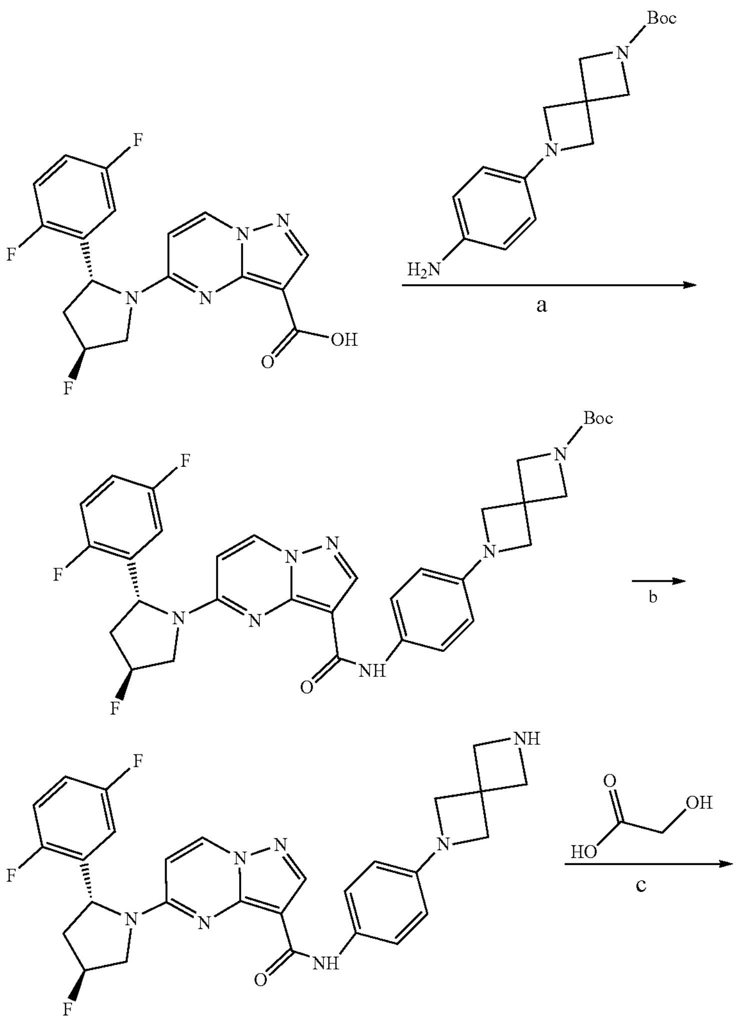

-continued

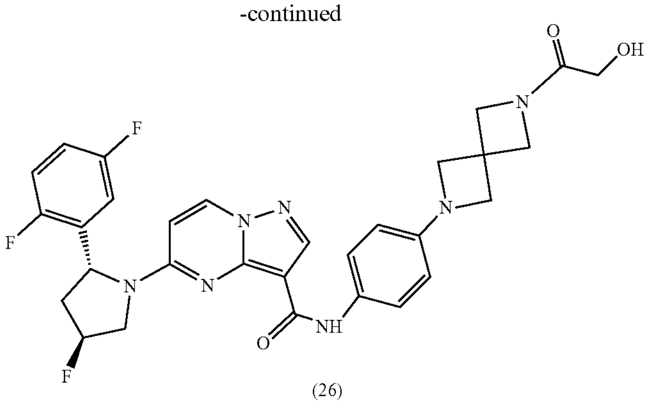

(26)

Step a: tert-butyl 6-(4-aminophenyl)-2,6-diazaspiro[3.3]heptane-2-carboxylate (178 mg, 0.607 mmol) (Intermediate B8) was added into a solution of 5-((2R,4S)-2-(2,5-difluorophenyl)-4-fluoropyrrolidin-1-yl)pyrazolo[1,5-a]pyrimidine-3-carboxylic acid (Intermediate A2, 200 mg, 0.552 mmol) and TBTU (217 mg, 0.607 mmol) in anhydrous DMF (5 mL), followed by dropwise addition of DIPEA (217 mg, 1.656 mmol) at 0° C., and the reaction system was stirred overnight at room temperature for 14 h. The reaction liquid was added with water (30 mL), mixed and stirred. A large amount of solid was precipitated, and then filtered under reduced pressure and dried to give crude tert-butyl 6-(4-(5-((2R,4S)-2-(2,5-difluorophenyl)-4-fluoropyrrolidin-1-yl)pyrazolo[1,5-a]pyrimidine-3-formamido)phenyl)-2,6-diazaspiro[3.3]heptane-2-carboxylate as a solid. (ES, m/z): 534.12[M+H]+.

Step b: the crude tert-butyl 6-(4-(5-((2R,4S)-2-(2,5-difluorophenyl)-4-fluoropyrrolidin-1-yl)pyrazolo[1,5-a]pyrimidine-3-formamido)phenyl)-2,6-diazaspiro[3.3]heptane-2-carboxylate obtained above was dissolved in DCM (6 mL). The solution was added with $CF_3COOH$ (2 mL), and stirred at room temperature for 3 h. The reaction liquid was concentrated by rotary evaporation, and added with water for dilution, followed by addition of aqueous ammonia to adjust the pH. A solid was precipitated, subjected to suction filtration, and dried to give N-(4-(2,6-diazaspiro[3.3]heptyl-2-yl)phenyl)-5-((2R,4S)-2-(2,5-difluorophenyl)-4-fluoropyrrolidin-1-yl)pyrazolo[1,5-a]pyrimidine-3-carboxamide as a solid (218 mg).

Step c: hydroxyacetic acid (37 mg, 0.490 mmol) was added into a solution of N-(4-(2,6-diazaspiro[3.3]heptyl-2-yl)phenyl)-5-((2R,4S)-2-(2,5-difluorophenyl)-4-fluoropyrrolidin-1-yl)pyrazolo[1,5-a]pyrimidine-3-carboxamide (218 mg, 0.409 mmol) and TBTU (157 mg, 0.490 mmol) in anhydrous DMF (10 mL), followed by dropwise addition of DIPEA (158 mg, 1.226 mmol) at 0° C., and the reaction mixture was stirred at room temperature for 4 h. The reaction liquid was added with water (30 mL) for mixing, and the mixture was extracted with EA (20 mL×2). The combined organic phases were washed with $H_2O$ (30 mL) and brine (40 mL), dried over anhydrous sodium sulfate and filtered. The filtrate was concentrated under reduced pressure to obtain a residue, which was purified by preparative plate (DCM:MeOH=15:1) to give 5-((2R,4S)-2-(2,5-difluorophenyl)-4-fluoropyrrolidin-1-yl)-N-(4-(6-(2-hydroxyacetyl)-2,6-diazaspiro[3.3]heptane-2-yl)phenyl)pyrazolo[1,5-a]pyrimidine-3-carboxamide (51 mg, 94%). (ES, m/z): 592.12 [M+H]+.

Example 27: 5-(3-(2,5-difluorophenyl)morpholinyl)-N-(4-(4-(2-hydroxyacetyl)piperazin-1-yl)phenyl)pyrazolo[1,5-a]pyrimidine-3-carboxamide (Compound 27)

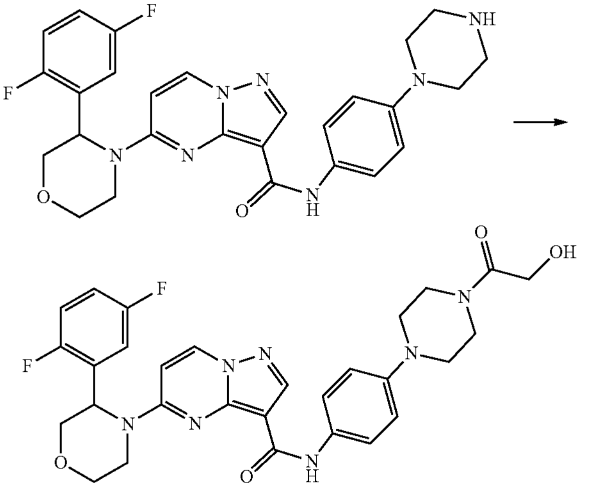

27

Hydroxyacetic acid (584 mg, 7.676 mmol) was added into a solution of 5-((2R,4S)-2-(2,5-difluorophenyl)-4-fluoropyrrolidin-1-yl)-N-(4-(piperidin-4-yl)phenyl)pyrazolo[1,5-a]pyrimidine-3-carboxamide (Intermediate A13, 997 mg, 1.919 mmol) and BOP (1274 mg, 2.878 mmol) in anhydrous DMF (10 mL), followed by dropwise addition of DIPEA (744 mg, 5.756 mmol) at 0° C., and the reaction mixture was stirred at room temperature. The reaction liquid was added with water (100 mL) for mixing, and the mixture was extracted with EA (80 mL×2). The organic phases were combined.

The organic phase was washed with $H_2O$ (100 mL) and brine (110 mL), dried over anhydrous sodium sulfate and filtered. The filtrate was concentrated under reduced pressure. The residue was purified by silica gel column chromatography (eluent: DCM:$CH_3OH$=100:1 to 50:1, v/v). The eluent containing the target product was collected and concentrated to give 5-(3-(2,5-difluorophenyl)morpholinyl)-N-(4-(4-(2-hydroxyacetyl)piperazin-1-yl)phenyl)pyrazolo[1,5-a]pyrimidine-3-carboxamide (609.8 mg, 55%). (ES, m/z): 578.12[M+H]+.

Example 28

According to the preparation process routes and operations of Example 27, compound 28 was prepared by adopting intermediate A14 and hydroxyacetic acid as starting materials.

| Example Nos. | Starting materials | Compound structures and Nos. | Characterization data |
| --- | --- | --- | --- |
| 28 | Intermediate A14, and 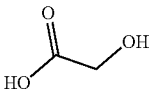 | 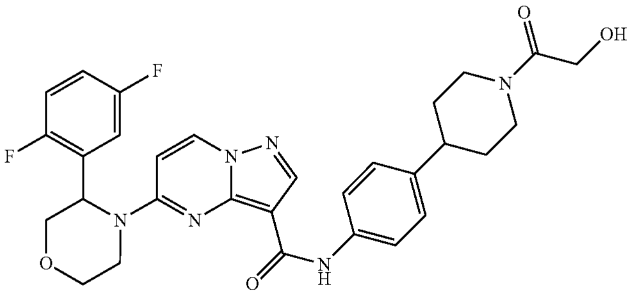 28 | (ES, m/z): 577.10 [M + H]+ |

Example 29: 5-(3-(5-fluoro-2-methoxypyridin-3-yl)morpholinyl)-N-(4-(4-(2-hydroxyacetyl)piperazin-1-yl)phenyl)pyrazolo[1,5-a]pyrimidine-3-carboxamide (Compound 29)

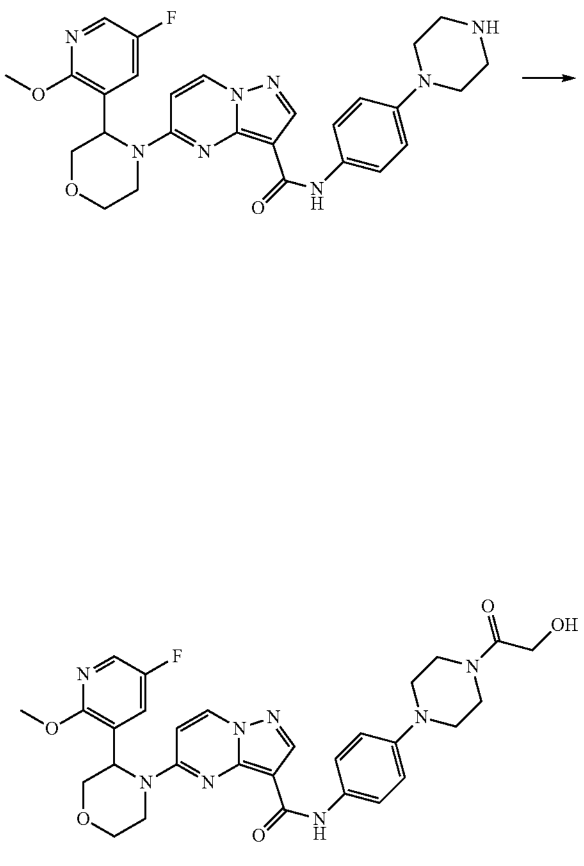

29

Hydroxyacetic acid (511 mg, 6.723 mmol) was added into a solution of 5-(3-(5-fluoro-2-methoxypyridin-3-yl)morpholino)-N-(4-(piperazin-1-yl)phenyl)pyrazolo[1,5-a]pyrimidine-3-carboxamide (Intermediate A15, 1.022 g, 1.92 mmol) and BOP (1274 mg, 2.878 mmol) in anhydrous DMF (10 mL), followed by dropwise addition of DIPEA (744 mg, 5.763 mmol) at 0° C., and the reaction system was stirred at room temperature overnight. The reaction liquid was added with water (100 mL) for mixing, and the mixture was extracted with EA (80 mL×2). The organic phases were combined. The organic phase was washed with $H_2O$ (100 mL) and brine (110 mL), dried over anhydrous sodium sulfate and filtered, and the filtrate was concentrated under reduced pressure. The residue was purified with silica gel column chromatography (eluent: DCM:$CH_3OH$=100:1 to 50:1). The eluent containing the target product was collected and concentrated to give 5-(3-(5-fluoro-2-methoxypyridin-3-yl)morpholinyl)-N-(4-(4-(2-hydroxyacetyl)piperazin-1-yl)phenyl)pyrazolo[1,5-a]pyrimidine-3-carboxamide (737 mg, 65.02%). (ES, m/z): 591.20[M+H]$^+$.

Example 30

According to the preparation process routes and operations of Example 29, compound 30 was prepared by adopting intermediate A16 and hydroxyacetic acid as starting materials.

| Example Nos. | Starting materials | Compound structures and Nos. | Characterization data |
|---|---|---|---|
| 30 | Intermediate A16, and 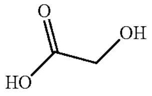 | 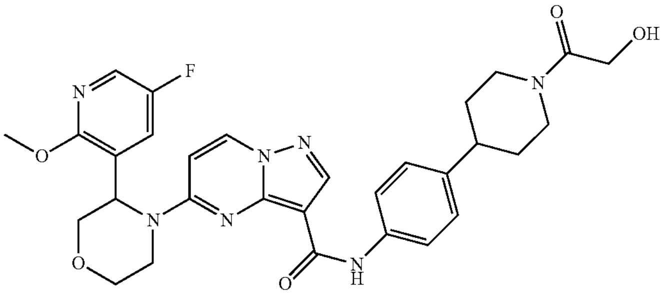 [SMILES: COc1ncc(F)cc1C1COCCN1c1ccn2ncc(C(=O)Nc3ccc(C4CCN(C(=O)CO)CC4)cc3)c2n1] 30 | (ES, m/z): 590.11 [M + H]$^+$ |

Examples 31 to 47

Referring to the preparation process routes and operations of intermediate preparation examples 1 to 30 and Examples 1 to 30, and the method disclosed in CN111936500A, compounds 31 to 47 were prepared by using (2R)-2-(2,5-difluorophenyl)-3-azabicyclo[3.1.0]hexane and each intermediate as starting materials.

| Example Nos. | Compound structures and Nos. | Characterization data (ES, m/z): [M + H]$^+$ |
|---|---|---|
| 31 | 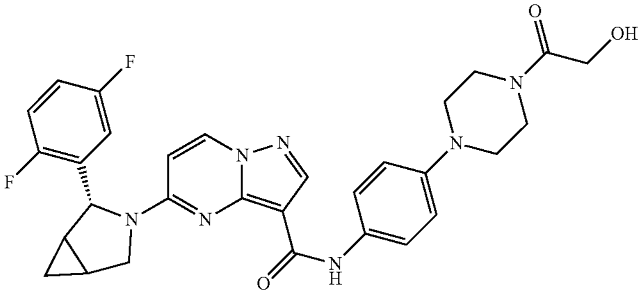 31 | 574.20 |
| 32 | 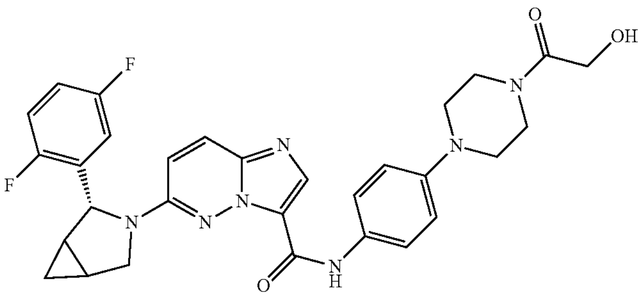 [SMILES: O=C(Nc1ccc(N2CCN(C(=O)CO)CC2)cc1)c1cnc2ccc(N3CC4CC4[C@@H]3c3cc(F)ccc3F)nn12] 32 | 574.12 |

-continued
| Example Nos. | Compound structures and Nos. | Characterization data (ES, m/z): $[M + H]^+$ |
|---|---|---|
| 33 | 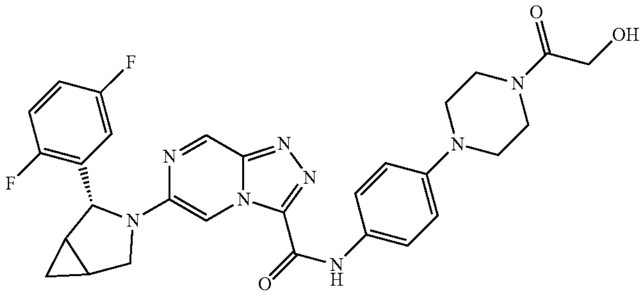 33 | 575.20 |
| 34 | 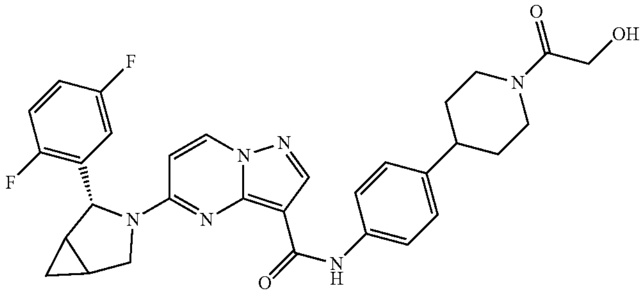 [SMILES: O=C(Nc1ccc(C2CCN(C(=O)CO)CC2)cc1)c1cnn2ccc(N3CC4CC4[C@@H]3c3cc(F)ccc3F)nc12] 34 | 573.20 |
| 35 | 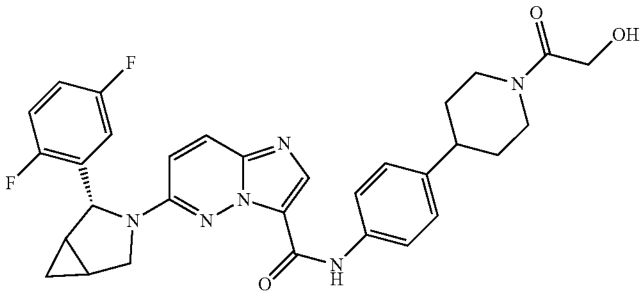 [SMILES: O=C(Nc1ccc(C2CCN(C(=O)CO)CC2)cc1)c1cnc2ccc(N3CC4CC4[C@@H]3c3cc(F)ccc3F)nn12] 35 | 573.20 |
| 36 | 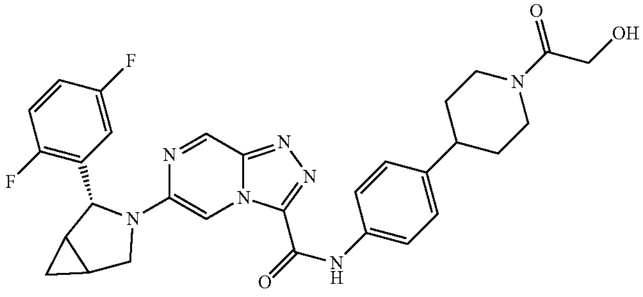 [SMILES: O=C(Nc1ccc(C2CCN(C(=O)CO)CC2)cc1)c1nnc2cnc(N3CC4CC4[C@@H]3c3cc(F)ccc3F)cn12] 36 | 574.19 |

-continued
| Example Nos. | Compound structures and Nos. | Characterization data (ES, m/z): [M + H]$^+$ |
|---|---|---|
| 37 | 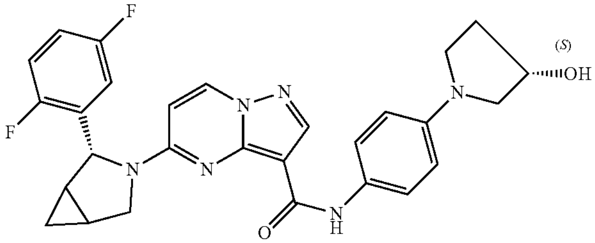 37 | 517.11 |
| 38 | 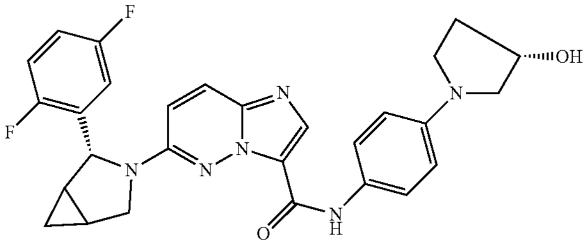 [SMILES: O=C(Nc1ccc(N2CC[C@H](O)C2)cc1)c1cnc2ccc(N3CC4CC4[C@@H]3c3cc(F)ccc3F)nn12] 38 | 517.12 |
| 39 | 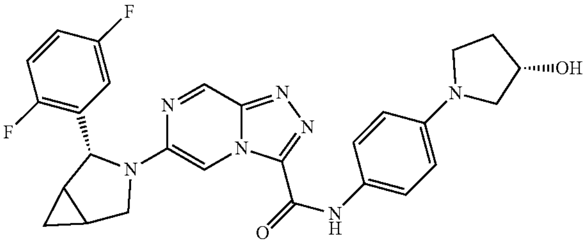 [SMILES: O=C(Nc1ccc(N2CC[C@H](O)C2)cc1)c1nnc2cnc(N3CC4CC4[C@@H]3c3cc(F)ccc3F)cn12] 39 | 518.17 |
| 40 | 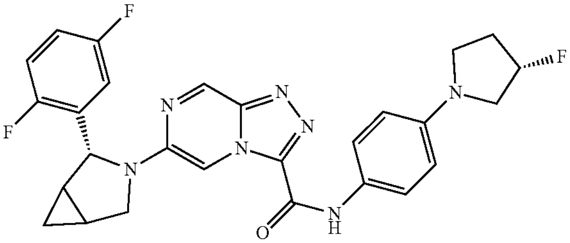 [SMILES: O=C(Nc1ccc(N2CC[C@H](F)C2)cc1)c1nnc2cnc(N3CC4CC4[C@@H]3c3cc(F)ccc3F)cn12] 40 | 520.13 |
| 41 | 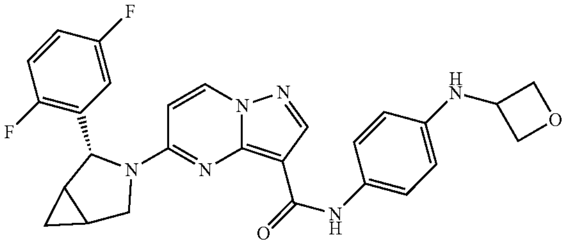 [SMILES: O=C(Nc1ccc(NC2COC2)cc1)c1cnn2ccc(N3CC4CC4[C@@H]3c3cc(F)ccc3F)nc12] 41 | 503.11 |

-continued
| Example Nos. | Compound structures and Nos. | Characterization data (ES, m/z): [M + H]$^+$ |
|---|---|---|
| 42 | 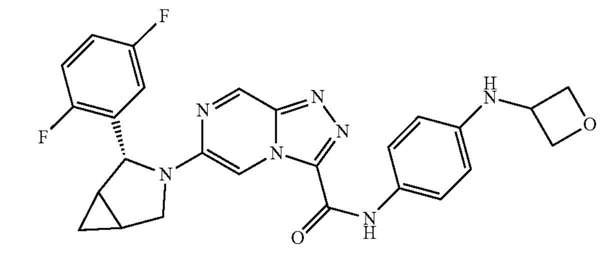 [SMILES: O=C(Nc1ccc(NC2COC2)cc1)c1nnc2cnc(N3CC4CC4[C@@H]3c3cc(F)ccc3F)cn12] 42 | 504.16 |
| 43 | 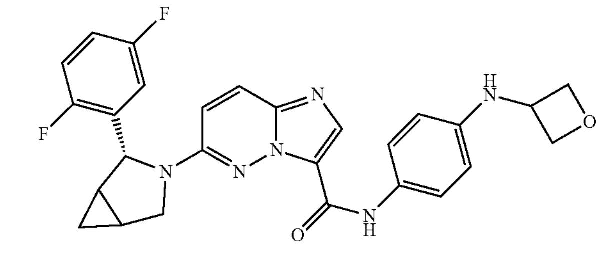 [SMILES: O=C(Nc1ccc(NC2COC2)cc1)c1cnc2ccc(N3CC4CC4[C@@H]3c3cc(F)ccc3F)nn12] 43 | 503.11 |
| 44 | 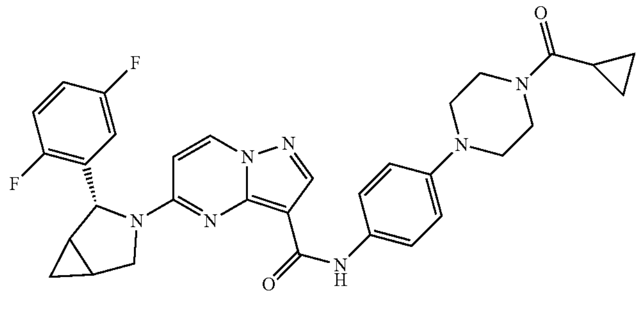 [SMILES: O=C(Nc1ccc(N2CCN(C(=O)C3CC3)CC2)cc1)c1cnn2ccc(N3CC4CC4[C@@H]3c3cc(F)ccc3F)nc12] 44 | 584.20 |
| 45 | 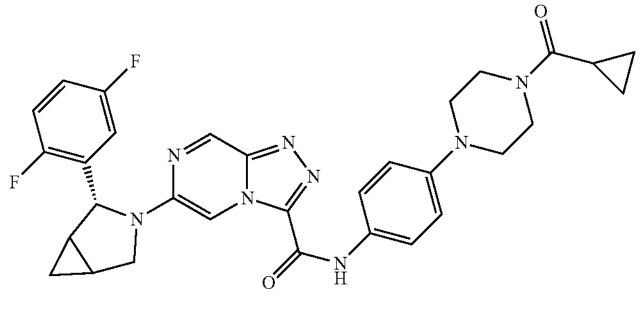 [SMILES: O=C(Nc1ccc(N2CCN(C(=O)C3CC3)CC2)cc1)c1nnc2cnc(N3CC4CC4[C@@H]3c3cc(F)ccc3F)cn12] 45 | 585.21 |

-continued

| Example Nos. | Compound structures and Nos. | Characterization data (ES, m/z): [M + H]$^+$ |
|---|---|---|
| 46 | 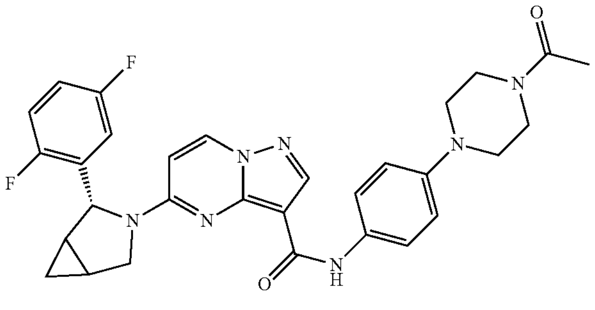 [SMILES: CC(=O)N1CCN(c2ccc(NC(=O)c3cnn4ccc(N5CC6CC6[C@@H]5c5cc(F)ccc5F)nc34)cc2)CC1] 46 | 558.19 |
| 47 | 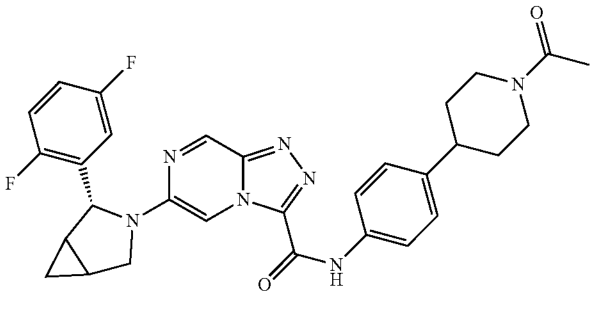 [SMILES: CC(=O)N1CCC(c2ccc(NC(=O)c3nnc4cnc(N5CC6CC6[C@@H]5c5cc(F)ccc5F)cn34)cc2)CC1] 47 | 558.20 |

Preparation Examples of Reference Compounds 1 to 5

Compounds D1 to D5 were prepared with reference to the preparation process routes and operations in the patent documents of WO2019029629A1 and WO2012034095A1.

| Compound Nos. | Compound structures | Reference patent documents |
|---|---|---|
| D1 | 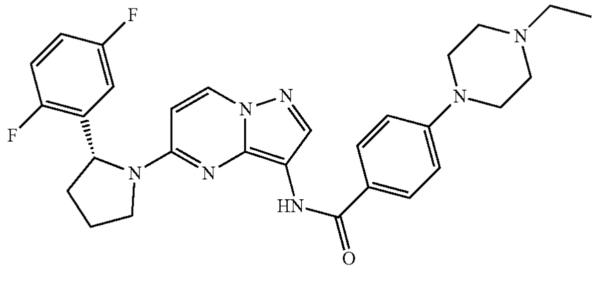 [SMILES: CCN1CCN(c2ccc(C(=O)Nc3cnn4ccc(N5CCC[C@@H]5c5cc(F)ccc5F)nc34)cc2)CC1] | The second compound in claim 6 in WO2019029629A1 |
| D2 | 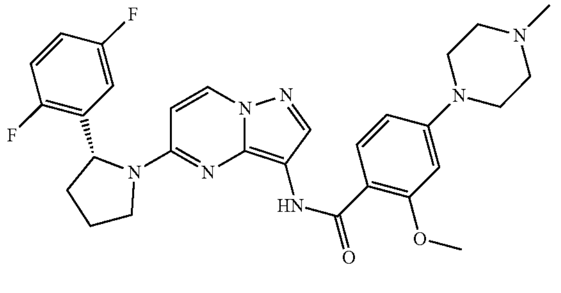 [SMILES: COc1cc(N2CCN(C)CC2)ccc1C(=O)Nc1cnn2ccc(N3CCC[C@@H]3c3cc(F)ccc3F)nc12] | Compound 2 on page 39 of the specification in WO2019029629A1 |

-continued

| Compound Nos. | Compound structures | Reference patent documents |
|---|---|---|
| D3 | 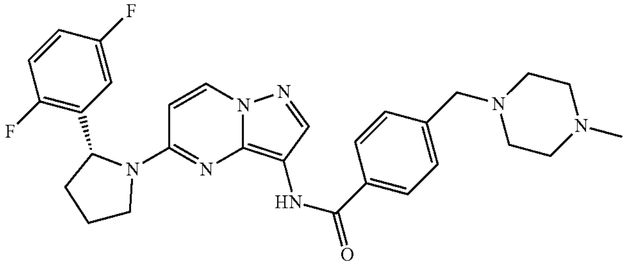 [SMILES: CN1CCN(Cc2ccc(C(=O)Nc3cnn4ccc(N5CCC[C@@H]5c5cc(F)ccc5F)nc34)cc2)CC1] | Compound 3 on page 39 of the specification in WO2019029629A1 |
| D4 | 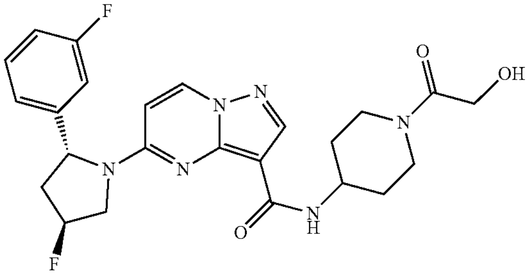 [SMILES: O=C(NC1CCN(C(=O)CO)CC1)c1cnn2ccc(N3C[C@@H](F)C[C@@H]3c3cccc(F)c3)nc12] | Compound X-39 in WO2012034095A1 |
| D5 | 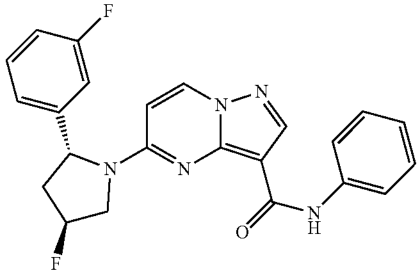 [SMILES: O=C(Nc1ccccc1)c1cnn2ccc(N3C[C@@H](F)C[C@@H]3c3cccc(F)c3)nc12] | X-62 in WO2012034095A1 |

Test Example 1. Inhibition of the Compounds Against TRK

1. Procedures:

1.1 Kinase Reaction:

The compound to be tested with a certain concentration gradient and an enzyme solution were successively added into a plate (kinase buffer (1× kinase buffer (Cisbio, Cat #62EZBFDD), pH 7.5; 5 mM $MgCl_2$, 1 mM DTT) was added into negative control wells), and the compound plate was centrifuged at 1000 rpm for 30 seconds. The plate was sealed and incubated in a Constant Temperature Incubator at 25° C. for 30 min. A substrate solution containing TK-Sub-biotin (Cisbio, Cat #61TKOBL) and ATP (Sigma, Cat #R0441) was prepared, the substrate solution was added into a 384-well plate, and the plate was centrifuged at 1000 rpm for 30 seconds. The plate was sealed and incubated in a Constant Temperature Incubator at 25° C. for 60 min.

| Kinases | Sources | Kinases Concentration (nM) | Substrates | Substrates Concentration (μM) | Antibody 1 | Antibody 1 Concentration (nM) | Antibody 2 | Antibody 2 Concentration (nM) |
|---|---|---|---|---|---|---|---|---|
| TRKA | Bioduro | 3 | TK-Sub- | 0.5 | TK- | 0.25 | XL665 | 31.25 |
| TRKB | | 15 | biotin | 2 | antibody | | | 125 |
| TRKC | | 15 | | 2 | | | | 125 |
| TRKA(G595R) | signalchem | 12 | | 0.4 | | | | 25 |
| TRKA(G667C) | | 0.8 | | 1 | | | | 62.5 |
| TRKC(G623R) | Bioduro | 3 | | 1 | | | | 62.5 |
| TRKC(G696A) | | 3 | | 1 | | | | 62.5 |

1.2 Kinase Assay:

TK antibody and XL665 were diluted, mixed and added into the assay plate, and the plate was centrifuged at 1000 rpm for 30 seconds. The plate was sealed and incubated in a Constant Temperature incubator Incubator at 25° C. for 60 min. The assay plate was placed on an Envision reader for reading. (HTRF 665/615 ratio: signal value at 665 nm/signal value at 615 nm)

$$\text{Inhibition}=(\text{ratio}_{negative\ control\ well}-\text{ratio}_{compound\ well})/(\text{ratio}_{negative\ control\ well}-\text{ratio}_{enzyme\text{-}free\ control\ well})\times 100\%$$

1.3 Data Analysis and Curve Fitting

Data were fitted in XLFit excel add-in version 5.4.0.8 to obtain $IC_{50}$ values.

1.4 QC Parameters

The reference compound was contained in each plate with an $IC_{50}$ within 3-fold value each time.

2. Test Results: As Shown in Table 1

TABLE 1

Inhibitory activity of the compounds of the present disclosure against NTRK kinase

| Test compounds | $IC_{50}$ (nM) TRKA | TRKB | TRKC | TRKA (G595R) | TRKA (G667C) | TRKC (G623R) | TRKC (G696A) |
|---|---|---|---|---|---|---|---|
| RXDX-101 | 0.555 | 1.483 | 1.322 | 117.108 | 3.393 | 21.567 | 0.732 |
| LOXO-195 | 0.179 | 0.687 | 0.293 | 1.306 | 5.604 | 3.476 | 0.421 |
| LOXO-101 | 0.536 | 2.603 | 2.557 | 102.085 | 22.071 | 53.297 | 2.548 |
| Compound 4 | 0.236 | 0.986 | 0.443 | <0.169351 | 0.183 | 0.205 | 0.383 |
| Compound 10 | 0.322 | 1.153 | 1.041 | <0.169351 | 0.57 | 0.804 | 0.558 |
| Compound 19 | 0.265 | 0.984 | 0.724 | <0.169351 | 0.308 | 0.241 | 0.936 |
| Compound 21 | 0.405 | 1.552 | 0.901 | <0.169351 | 0.632 | 0.749 | 1.204 |

Note:
the above RXDX-101, LOXO-195 and LOXO-101 are all disclosed compounds, and are commercially available (medicines or chemical products).

The results show that: the compounds of the present disclosure show higher inhibition activities in various kinases. The inhibition activities of the compounds of the present disclosure against TRKA, TRKB, TRKC and TRKC-G696A are superior to or equivalent to those of RXDX-101, LOXO-195 and LOXO-101, while the inhibition activities of the compounds of the present disclosure against various mutant drug-resistant kinases (G595R, G667C and G623R) is significantly superior to those of RXDX-101, LOXO-195 and LOXO-101.

Test Example 2. Inhibition of the Compounds Against ALK and ROS1

1. Procedures:

1.1 Kinase Reaction:

Compounds were diluted to a certain concentration in DMSO with 4-fold gradients. The compound with a certain concentration, an enzyme solution and DMSO were added into a 384-well plate, and the plate was incubated at room temperature for 10 min. The plate was added with fluorescein labeled peptide and ATP (sigma, Cat. No.: A7699-1G, Lot No.: 987-65-5), incubated at 28° C. for a certain time, and then added with a terminating solution. The plate was subjected to reading.

$$\text{Inhibition rate for single concentration: inhibition rate}=(OD_{negative\ control\ well}-OD_{compound\ well})/(OD_{negative\ control\ well}-OD_{enzyme\text{-}free\ control\ well})\times 100\%$$

| Kinases | Sources | Cat. Nos. | Lot Nos. | Concentration of kinases (nM) | Km ATP concentration (μM) | Substrates | Concentration of substrates (μM) |
|---|---|---|---|---|---|---|---|
| ALK | Carna | 08-105 | 08CBS-0112 | 0.6 | 82 | Peptide22 | 3 |
| ROS1 | Carna | 08-163 | 08CBS-0253 | 1 | 37 | Peptide22 | 3 |

1.2 Data Analysis and Curve Fitting

Data were fitted in XLFit excel add-in version 4.3.1 to obtain $IC_{50}$ values, and the results are shown in Table 2.

TABLE 2

Inhibitory activities of the compounds of the present disclosure against ALK and ROS1 kinases

| Compound ID | $IC_{50}$ (nM) ALK | $IC_{50}$ (nM) ROS1 |
|---|---|---|
| RXDX-101 | 3.4 | 1.2 |
| LOXO-195 | 391 | 0.66 |
| LOXO-101 | >1000 | 72 |
| Compound 4 | 22 | 0.19 |
| Compound 10 | 31 | 0.40 |
| Compound 19 | 39 | 0.23 |
| Compound 21 | 30 | 0.33 |

The results show that: a plurality of compounds of the present disclosure show stronger inhibitory activities against ROS1 kinase, which are significantly superior to those of RXDX-101 and LOXO-101, and are superior to that of LOXO-195. The compounds have good inhibitory activities against ALK kinase, which are superior to those of LOXO-101 and LOXO-195.

Test Example 3. In Vitro Cell Proliferation Inhibition Activities of the Compounds 1. Cell Lines Source of 6 kinds of cell lines for the test: KYinno Biotechnology (Beijing) Co., Ltd.

Cell type: murine B cells

Culture medium: RPMI-1640+10% FB S

2. Test Method

Cells in the logarithmic growth phase were harvested and counted using a platelet counter. The cell suspension with a certain density was pipetted uniformly and seeded into a 96-well plate with each well of 100 μL, and shaken to make the cells uniformly disperse into the wells. 100 μL of compound solution with certain concentration gradient was added into each well, and 3 duplicate wells were set for each concentration. The plate was cultured in a $CO_2$ incubator at 37° C. for 72 h. 20 μL of MTT working solution (5 mg/mL) was added into each well, and the plate was placed at 37° C. for 4 h, and centrifuged at 1000 rpm for 5 min by a plate centrifuge. After 180 μL of culture medium was discarded, the plate was added with 150 μL of DMSO, and mixed well with a microplate shaker, the plate bottom was wiped, and optical density (OD) at 550 nm was detected with a microplate reader.

3. Data Analysis

Inhibition rate=$(OD_{control\ well}-OD_{test\ well})/(OD_{control\ well}-OD_{blank\ well})\times 100\%$, and half maximal inhibitory concentration $IC_{50}$ values were calculated from each concentration inhibition rate using SPSS software.

4. Test Results: As Shown in Table 3:

TABLE 3

Inhibitory activities of the compounds of the present disclosure against TRK mutant cell strains

| Compounds | $IC_{50}$(nM) Ba/F3 LMNA-NTRK1-G595R | Ba/F3 LMNA-NTRK1-G667C | Ba/F3 ETV6-NTRK3-G623R | Ba/F3 ETV6-NTRK3-G696A | Ba/F3 LMNA-NTRK1 | Ba/F3 ETV6-NTRK2 |
|---|---|---|---|---|---|---|
| RXDX-101 | 627.847 | 23.995 | 23.995 | 1.578 | 2.821 | 2.133 |
| LOXO-101 | 520.074 | 267.49 | 375.825 | 35.809 | 41.417 | 15.091 |
| LOXO-195 | 6.868 | 112.074 | 4.539 | 4.505 | 9.08 | 2.89 |
| Compound 4 | 0.166 | 2.209 | 0.674 | 0.466 | 0.729 | 1.768 |
| Compound 7 | 0.156 | 1.783 | 0.499 | 0.736 | — | — |
| Compound 10 | 0.095 | 0.536 | 0.277 | 0.693 | 0.526 | 0.977 |
| Compound 12 | 0.215 | 1.531 | 0.237 | 0.112 | 0.635 | 1.134 |
| Compound 13 | — | 1.471 | — | — | — | — |
| Compound 18 | — | 3.431 | — | — | — | — |
| Compound 19 | 0.208 | 1.185 | 0.426 | 0.321 | 0.416 | 0.866 |
| Compound 21 | — | 0.584 | — | — | — | — |
| Compound 23 | 0.525 | 4.927 | 0.852 | 0.435 | — | — |

Note:
— indicates not detected.

TABLE 4

Inhibitory activities of the control compounds against TRK mutant cell strains

| Compounds | IC50 (nM) Ba/F3 LMNA-NTRK1-G595R | Ba/F3 LMNA-NTRK1-G667C | Ba/F3 ETV6-NTRK3-G623R | Ba/F3 ETV6-NTRK3-G696A | Ba/F3 LMNA-NTRK1 | Ba/F3 ETV6-NTRK2 |
|---|---|---|---|---|---|---|
| D1 | 289.166 | 307.093 | 24.835 | 258.186 | 1.604 | 6.09 |
| D2 | 229.83 | 42.73 | 46.469 | 201.714 | 1.026 | 13.36 |
| D3 | 522.303 | 316.355 | 207.449 | 541.876 | 8.68 | 17.426 |
| D4 | 65.891 | ≥1000 | 16.96 | 140.783 | 9.522 | 14.924 |
| D5 | 4.595 | 412.709 | 13.282 | 90.807 | 2.142 | 12.198 |

The results show that: a plurality of compounds of the present disclosure show better in vitro cell inhibitory activities in various wild type and mutant drug-resistant cell strains, and are significantly superior to RXDX-101, LOXO-195, LOXO-101 and the compounds D1 to D5 in the prior art.

Test Example 4: Study of In Vivo Mechanism of the Compounds

1. Test Method 1.1 Model Preparation:

The mutant drug-resistant cells Ba/F3 LMNA-NTRK1-G595R in the logarithmic growth phase were harvested and re-suspending in serum-free culture medium to make the cell concentration at $6\times10^7$-$10\times10^7$ cells/mL. The cell suspension was added with equal volume of Matrigel to make the final cell concentration at $3\times10^7$-$5\times10^7$ cells/mL. The animal model was prepared by subcutaneously inoculating 0.1 mL of tumor cell suspension in the axilla of the forelimb of NuNu mice (female, 4-6 weeks, Beijing Vital River Laboratory Animal Technology Co., Ltd.) in an amount of $3\times10^6$-$5\times10^6$ cells/mouse.

1.2 Grouping:

The maximum and the minimum tumor diameters of the xenografts in nude mice were measured using a vernier caliper, and the tumor volume (TV) was calculated according to the formula: $V=\frac{1}{2}\times a\times b^2$, where a and b represent the maximum and minimum diameters of the tumor mass, respectively. Nude mice with appropriate tumor volume were selected and the mice were evenly divided into 7 groups of 3 mice (200-300 $mm^3$) by tumor volume using a random number method.

1.3 Administration

Gavage administration was performed according to animal weight at an administration volume of 10 mL/kg, and compound No. 4 was formulated to the required administration concentration using "3% DMSO+96% HP-β-CD (0.5 g/mL)+1% HCL".

A total of 3 mice in the control group were selected, and tumor tissues were taken and cryopreserved 4 h after the administration of the vehicle. The compound No. 4 of the present disclosure was administered to other groups at 100 mg/kg, and tumor tissues was taken at 0.25 h, 1 h, 4 h, 8 h, 12 h and 24 h for cryopreservation.

1.4 Protein Extraction and Quantification

A certain mass of tumor tissue was taken and added into a corresponding volume of protein lysate (RIPA lysate (Thermo Fisher, Cat. No. 89900): protease inhibitor (cOmplete, Mini, EDTA-free, EASYpack; Roche, Cat. No. 04693159001): phosphatase inhibitor (PhosStop, EASY pack; Roche, Cat. No. 04906837001)=8:1:1), homogenized and lysed in ice bath for 30 min. The mixture was subjected to high-speed centrifugation at low temperature, and then the supernatant was taken for BCA protein quantification (procedure according to the BCA protein quantification kit (Qiagen, Cat. No. PA115-01)). Finally, after the protein concentration was adjusted to be uniform by lysate, loading buffer was added, and the mixture was boiled at 100° C. for 10 min.

1.5 Western-Blot 4-20% of 10-well prefabricated gel was adopted; the sample loading amount was 100 μg; 140 V electrophoresis was performed for 1-1.5 h; the 300 mA wet-transfer was performed for 1.5-2 h; the membrane was blocked with 5% BSA for 2-3 h; incubating with primary antibody overnight at 4° C. (Trk 1:5000, p-Trk, PLCγ1, p-PLCγ1, AKT, p-AKT, actin 1:1000) and the membrane was washed with 0.1% TBST for 5 min for 4 times; incubating with the secondary antibody at room temperature for 2 h (1:5000), ECL-illuminated and exposed.

| Antibodies | Manufacturers | Cat. Nos. |
|---|---|---|
| Anti-TrkA + TrkB + TrkC antibody [EPR17341] | Abcam | ab181560 |
| Anti-TrkA (phospho Y490) + TrkB (phospho Y516) + TrkC (phospho Y516) antibody [EPR19140] | | ab197071 |
| Akt (pan) (C67E7) Rabbit mAb | CST | 4691s |
| Phospho-Akt (Ser473) Antibody | | 9271s |
| PLCγ1 (D9H10) XP ® Rabbit mAb | | 5690s |
| Phospho-PLCγ1 (Tyr783) Antibody | | 2821s |
| β-actin antibody | Beijing Zhong | TA-09 |
| Horseradish enzyme-labeled goat anti-mouse IgG | Shan -Golden Bridge | ZB-5305 |
| Horseradish enzyme-labeled goat anti-rabbit IgG (H + L) | Biological Technology Co., Ltd. | ZB-5301 |

2. Test Results: As Shown in the FIGURE

It can be seen from the test results: as time goes on, the expression of TRK, p-TRK, p-PLCγ1 and p-AKT in the FIGURE is all significantly reduced, which proves that the compound No. 4 of the present disclosure can significantly reduce the protein level of TRK and p-TRK, and further effectively inhibit the phosphorylation of p-PLCγ1/PLCγ1 and p-AKT/AKT so as to regulate the growth and proliferation of cells.

Test Example 5: In Vivo Pharmacodynamic Test of the Compounds on NTRK Mutation Drug-Resistant Xenograft Model Test Method 1.1 Model Preparation The cells in the logarithmic growth phase were collected and re-suspending in serum-free culture medium to make the cell concentration at $6\times10^7$-lox $10^7$ cells/mL. The cell suspension was added with equal volume of Matrigel to make the final cell concentration at $3\times10^7$-$5\times10^7$ cells/mL. The animal model was established by subcutaneously inoculating 0.1 mL of tumor cell suspension in the axilla of the forelimb of NuNu mice (female, 4-6 weeks, Beijing Vital River Laboratory Animal Technology Co., Ltd.) in an amount of $3\times10^6$-$5\times10^6$ cells/mouse.

1.2 Grouping

The maximum and the minimum tumor diameters of the xenografts in nude mice were measured using a vernier caliper, and the tumor volume (TV) was calculated according to the formula: $V=\frac{1}{2}\times a\times b^2$, where a and b represent the maximum and minimum diameters of the tumor mass, respectively. Nude mice with appropriate tumor volume were selected and the mice were evenly divided into 7 groups of 6 mice (100-200 $mm^3$) by tumor volume using a random number method.

1.3 Observation of Indexes

Gavage administration was performed on the day of grouping according to animal weight at an administration volume of 10 mL/kg, LOXO-195 was formulated with 0.5% CMC-Na to the required administration solution, and compounds No. 4 and No. 10 were formulated with "3% DMSO+96% HP-β-CD (0.5 g/mL)+1% HCL" to the required administration solution. Tumor diameters were measured twice weekly and tumor volume was calculated. The specific indexes are as follows:

Animal weight: animals were weighed before dosing every morning and a weight loss of greater than 20% was defined as a drug toxic response (observed the day following the last administration);

Tumor volume (TV)=V=½×a×b$^2$, where a and b represent the maximum and minimum diameters of the tumor mass, respectively (observed the day following the last administration);

Relative tumor proliferation rate T/C (%): T/C (%)=TRTV/CRTV×100% (TRTV: administration group RTV, CRTV: control group RTV);

Tumor growth inhibition rate (TGI)=[1−(Ti−T0)/(Vi−V0)]×100%. (where Ti represents the mean tumor volume of a certain administration group on a certain day; TO represents the mean tumor volume of the administration group at the start of administration, Vi represents the mean tumor volume of the vehicle control group on a certain day (same day as Ti) and V0 represents the mean tumor volume of the vehicle control group at the start of administration);

Tumor inhibition rate: at the end of the test, the animals were executed by removing the cervical vertebrae. The tumor masses were peeled off and weighed, and photographed, the tumor inhibition rate was calculated according to the formula: tumor inhibition rate=(mean tumor weight of control group−mean tumor weight of administration group)/mean tumor weight of control group×100%.

Test Results 2.1 Ba/F3 LMNA-NTRK1-G667C Model 2.1.1 Effect of Drugs on Weight of Tumor-Bearing Mice The weight of mice in each dose group of each compound has an increasing trend, and the increasing trend is more significant than that of a control group. The weight of mice in each dose group of each compound is significantly increased, which is possibly related to the compound, or due to that the compound can inhibit the tumor growth, so that the mice have a better state and significant weight increase. The results are shown in Table 5.

2.1.2 Effect of Drugs on Tumor Weight and Tumor Inhibition Rate of Tumor-Bearing Mice The data results show that: compared with LOXO-195, the compound No. 4 and the compound No. 10 of the present disclosure have more significant inhibition on tumor growth under the same administration dose (100 mg/kg); further, the compound No. 4 and the compound No. 10 (100 mg/kg) of the present disclosure also exhibit better tumor inhibition effect than the LOXO-195 group (200 mg/kg) at higher dose. The results are shown in Table 5.

TABLE 5

In vivo results of Ba/F3 LMNA-NTRK1-G667C model

| Group | Dose (mg/kg) | Number of animals (Survival/total) | Rate of weight gain (%) | Tumor volume (mm$^3$) | TGI (%) | Tumor weight (g) | Tumor weight inhibition rate (%) |
|---|---|---|---|---|---|---|---|
| Vehicle | — | (5/6)▲ | 1.59 | 521.3 ± 183.8 | — | 0.55 ± 0.16 | |
| LOXO-195 | 100 | (6/6) | 2.38 | 381.2 ± 134.4 | 36.4 | 0.43 ± 0.18 | 21.57 |
| | 200 | (5/6) | 7.88 | 154.5 ± 92.2 | 95.4 | 0.22 ± 0.16** | 59.96 |
| Compound 4 | 100 | (6/6) | 8.16 | 197.5 ± 85.4 | 84.0 | 0.21 ± 0.08** | 61.17 |
| Compound 10 | 100 | (6/6) | 5.75 | 91.6 ± 19.5 | 111.6 | 0.12 ± 0.02*** | 77.80 |

Note:
▲indicates one mouse died on the day of dissection in the vehicle group;
***indicates $p < 0.001$ compared with the vehicle control group;

2.2 Ba/F3 LMNA-NTRK1-G595R Model 2.2.1 Effect of Drugs on Weight of Tumor-Bearing Mice The weight of mice in each dose group of each compound has an increasing trend, and the increasing trend is more significant than that of a control group. The weight of mice in each dose group of each compound is significantly increased, which is possibly related to the compound, or due to that the compound can inhibit the tumor growth, so that the mice have a better state and significant weight increase. The results are shown in Table 6.

2.2.2 Effect of Drugs on Tumor Weight and Tumor Inhibition Rate of Tumor-Bearing Mice The data results show that: compared with LOXO-195 (100 mg/kg), the compound No. 4 and the compound No. 10 of the present disclosure can achieve significant inhibition on the weight of tumor tissues under lower dosage (50 mg/kg) with a tumor weight inhibition rate of more than 90%. The results are shown in Table 6.

TABLE 6

| In vivo results of Ba/F3 LMNA-NTRK1-G595R model | | | | | | | |
|---|---|---|---|---|---|---|---|
| Group | Dose (mg/kg) | Number of animals (Survival/total) | Rate of weight gain (%) | Tumor volume ($mm^3$) | TGI (%) | Tumor weight (g) | Tumor weight inhibition rate (%) |
| Vehicle | — | (6/6) | 3.83 | 568.4 ± 154.8 | — | 0.51 ± 0.14 | |
| LOXO-195 | 100 | (6/6) | 8.59 | 66.3 ± 37.1 | 124.6 | 0.12 ± 0.06*** | 76.58 |
| Compound 4 | 50 | (6/6) | 10.66 | 15.7 ± 12.6 | 136.9 | 0.02 ± 0.01***## | 96.16 |
| Compound 4 | 100 | (6/6) | 8.32 | 11.3 ± 9.7 | 138.0 | 0.02 ± 0.01***## | 96.83 |
| Compound 10 | 50 | (6/6) | 13.47 | 20.0 ± 12.6 | 134.7 | 0.01 ± 0.01***## | 98.09 |
| Compound 10 | 100 | (6/6) | 4.36 | 25.8 ± 8.3 | 132.5 | 0.02 ± 0.01***## | 96.75 |

Note:
***indicates $p < 0.001$ compared with the control group;
indicates $p < 0.01$ compared with LOXO-195

The invention claimed is:

1. A compound of formula (I), or a tautomer, a stereoisomer, an optical isomer, a solvate, a nitrogen oxide, a prodrug, an isotopic derivative or a pharmaceutically acceptable salt thereof, (I)

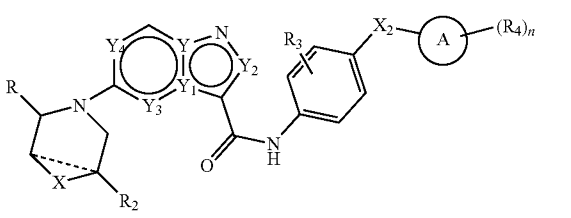

wherein, X is selected from: a bond, —O—, —S—, —NH—, and —$CH_2$—;

Y is N, $Y_1$ is C, $Y_2$ is —CH—, $Y_3$ is N, and $Y_4$ is —CH—;

$X_2$ is selected from: a bond, —$(CH_2)_p$—, and —NH—, wherein p is 1, 2, 3 or 4;

------ represents that the bond is absent or is present;

R is selected from: phenyl and 5-6 membered heteroaryl, wherein each phenyl or heteroaryl is unsubstituted or substituted with at least one substituent selected from $R_1$; the heteroatoms are independently selected from O, N, and S, and the number of the heteroatoms is 1, 2, or 3;

$R_1$, when present, is each independently selected from: hydrogen, halogen, —OH, amino, —$NHC_{1-6}$ alkyl, —$N(C_{1-6}$ alkyl$)_2$, cyano, $C_{1-6}$ alkyl unsubstituted or substituted with at least one $R_{1a}$, $C_{1-6}$ alkoxy unsubstituted or substituted with at least one $R_{1a}$, $C_{3-6}$ cycloalkyl unsubstituted or substituted with at least one $R_{1a}$, $C_{3-6}$ cycloalkoxy unsubstituted or substituted with at least one $R_{1a}$, and —$SC_{1-6}$ alkyl;

$R_{1a}$, when present, is each independently selected from: $C_{1-6}$ alkyl, $C_{1-6}$ alkoxy, nitro, halogen, —OH, amino, —$NHC_{1-6}$ alkyl, —$N(C_{1-6}$ alkyl$)_2$, and cyano;

$R_2$ is selected from: H, halogen, hydroxyl, amino, and substituted or unsubstituted $C_{1-6}$ alkyl, wherein "substituted" means substituted with 1, 2 or 3 substituent(s) selected from halogen and hydroxyl;

$R_3$ is selected from: H, halogen, —OH, amino, $C_{1-6}$ alkyl, and $C_{1-6}$ alkoxy;

ring A is selected from: $C_{3-6}$ cycloalkyl, 4-6 membered heterocycloalkyl, $C_{6-8}$ bridged cyclyl, 6-8 membered heterobridged cyclyl, $C_{8-10}$ fused cyclyl, 8-10 membered heterofused cyclyl, $C_{7-12}$ monospiro cyclyl, and 7-12 membered heteromonospiro cyclyl, wherein heteroatoms in the heterocycloalkyl, the heterobridged cyclyl, the heterofused cyclyl, and the heteromonospiro cyclyl are independently selected from O, S, and N, and the number of the heteroatoms is selected from 1, 2, 3, and 4;

$R_4$ is at any substitutable position on ring A and is independently selected from: —H, —OH, halogen, —CN, oxo, substituted or unsubstituted $C_{1-6}$ alkyl, —$(CH_2)_m$—OH, —$(CH_2)_m$—COOH, —$(CH_2)_m$—CO—$NH_2$, —CO—$(CH_2)_m$—$NH_2$, —CO—$CR_{4a}R_{4b}$—OH, and —CO—$R_{4b}$; wherein, the oxo means that two H of the same substitution site are substituted with the same O to form a double bond; m is selected from 1, 2, 3, and 4; $R_{4a}$ is selected from hydrogen and unsubstituted or substituted $C_{1-4}$ alkyl; $R_{4b}$ is selected from H, unsubstituted or substituted $C_{1-6}$ alkyl, and unsubstituted or substituted $C_{3-6}$ cycloalkyl, a substituent for the substitution is independently selected from —OH, —$NH_2$, and halogen, and the number of the substituents is selected from 1, 2, and 3; and n is selected from 1, 2, 3, and 4.

2. The compound, or the tautomer, the stereoisomer, the optical isomer, the solvate, the nitrogen oxide, the prodrug, the isotopic derivative or the pharmaceutically acceptable salt thereof according to claim 1, wherein the compound has a structure of formula (I-A-1a):

I-A-1a

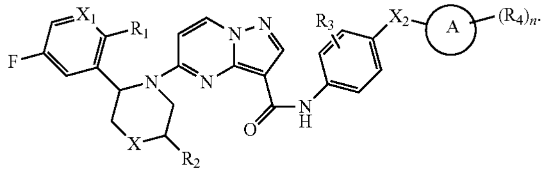

wherein, $R_1$, $R_2$, $R_3$, $R_4$, $X_2$, X, ring A and n are as defined in claim 1; and $X_1$ is —CH— or N.

3. The compound, or the tautomer, the stereoisomer, the optical isomer, the solvate, the nitrogen oxide, the prodrug, the isotopic derivative or the pharmaceutically acceptable salt thereof according to claim 1, wherein the compound has a structure of formula (I-B-1a):

I-B-1a

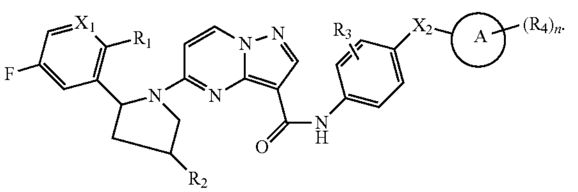

wherein, $R_1$, $R_2$, $R_3$, $R_4$, $X_2$, ring A and n are as defined in claim 1; and $X_1$ is —CH— or N.

4. The compound, or the tautomer, the stereoisomer, the optical isomer, the solvate, the nitrogen oxide, the prodrug, the isotopic derivative or the pharmaceutically acceptable salt thereof according to claim 1, wherein $R_1$, when present, is each independently selected from: hydrogen, halogen, —OH, amino, cyano, $C_{1-6}$ alkyl unsubstituted or substituted with at least one $R_{1a}$, and $C_{1-6}$ alkoxy unsubstituted or substituted with at least one $R_{1a}$.

5. The compound, or the tautomer, the stereoisomer, the optical isomer, the solvate, the nitrogen oxide, the prodrug, the isotopic derivative or the pharmaceutically acceptable salt thereof according to claim 1, wherein $R_{1a}$, when present, is each independently selected from: $C_{1-3}$ alkyl, $C_{1-3}$ alkoxy, nitro, halogen, —OH, amino, —$NHC_{1-6}$ alkyl, —$N(C_{1-6}$ alkyl$)_2$, and cyano.

6. The compound, or the tautomer, the stereoisomer, the optical isomer, the solvate, the nitrogen oxide, the prodrug, the isotopic derivative or the pharmaceutically acceptable salt thereof according to claim 1, wherein $R_2$ is selected from: H, F, OH, and substituted or unsubstituted $C_{1-6}$ alkyl, wherein "substituted" means substituted with 1, 2 or 3 substituents selected from halogen and hydroxyl.

7. The compound, or the tautomer, the stereoisomer, the optical isomer, the solvate, the nitrogen oxide, the prodrug, the isotopic derivative or the pharmaceutically acceptable salt thereof according to claim 1, wherein the compound has a structure of formula (I-D-a):

(I-D-a)

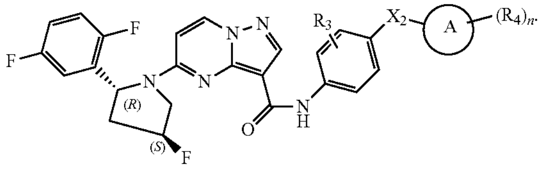

8. The compound, or the tautomer, the stereoisomer, the optical isomer, the solvate, the nitrogen oxide, the prodrug, the isotopic derivative or the pharmaceutically acceptable salt thereof according to claim 1, wherein $R_3$ is selected from: H, halogen, —OH, amino, $C_{1-3}$ alkyl, and $C_{1-3}$ alkoxy.

9. The compound, or the tautomer, the stereoisomer, the optical isomer, the solvate, the nitrogen oxide, the prodrug, the isotopic derivative or the pharmaceutically acceptable salt thereof according to claim 1, wherein ring A is selected from: 4-6 membered heterocycloalkyl, 6-8 membered heterobridged cyclyl, 8-10 membered heterofused cyclyl, and 7-12 membered heteromonospiro cyclyl; wherein heteroatoms in the heterocycloalkyl, the heterobridged cyclyl, the heterofused cyclyl and the heteromonospiro cyclyl are independently selected from O, S, and N, and the number of the heteroatoms is selected from 1, 2, 3, and 4.

10. The compound, or the tautomer, the stereoisomer, the optical isomer, the solvate, the nitrogen oxide, the prodrug, the isotopic derivative or the pharmaceutically acceptable salt thereof according to claim 1, wherein $R_4$ is independently selected from: —H, —OH, halogen, —CN, oxo, substituted or unsubstituted $C_{1-6}$ alkyl, —CO—$CR_{4a}R_{4b}$—OH, and —CO—$R_{4b}$; wherein, the oxo means that two H of the same substitution site are substituted with the same O to form a double bond; $R_{4a}$ is selected from hydrogen and unsubstituted or substituted $C_{1-4}$ alkyl; $R_{4b}$ is selected from unsubstituted or substituted $C_{1-6}$ alkyl and unsubstituted or substituted $C_{3-6}$ cycloalkyl, a substituent for the substitution is independently selected from —OH, —$NH_2$, and halogen, and the number of the substituents is selected from 1, 2, and 3.

11. The compound, or the tautomer, the stereoisomer, the optical isomer, the solvate, the nitrogen oxide, the prodrug, the isotopic derivative or the pharmaceutically acceptable salt thereof according to claim 1, wherein the compound one of the compounds in the following table:

| Serial number | Structural formulas |
|---|---|
| 1 | 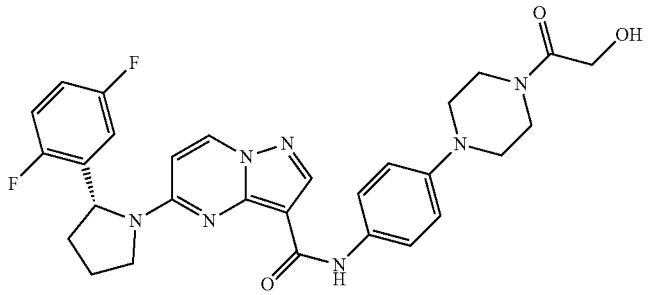 [SMILES: O=C(Nc1ccc(N2CCN(C(=O)CO)CC2)cc1)c1cnn2ccc(N3CCC[C@@H]3c3cc(F)ccc3F)nc12] |

-continued
| Serial number | Structural formulas |
|---|---|
| 2 | 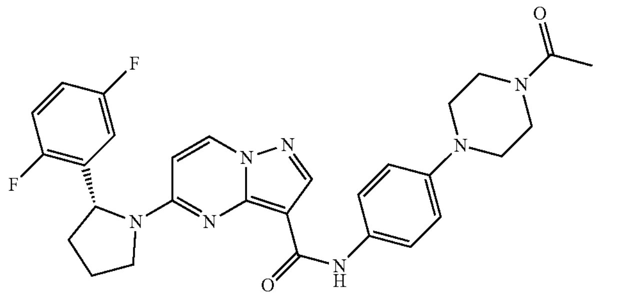 [SMILES: CC(=O)N1CCN(c2ccc(NC(=O)c3cnn4ccc(N5CCC[C@@H]5c5cc(F)ccc5F)nc34)cc2)CC1] |
| 3 | 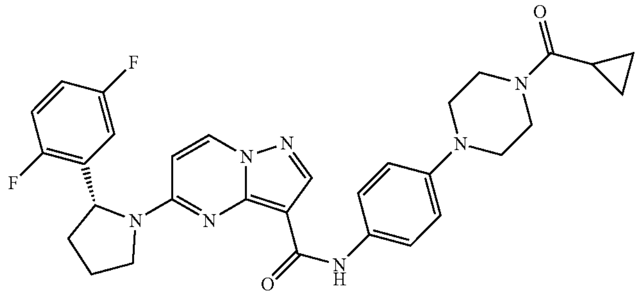 [SMILES: O=C(Nc1ccc(N2CCN(C(=O)C3CC3)CC2)cc1)c1cnn2ccc(N3CCC[C@@H]3c3cc(F)ccc3F)nc12] |
| 4 | 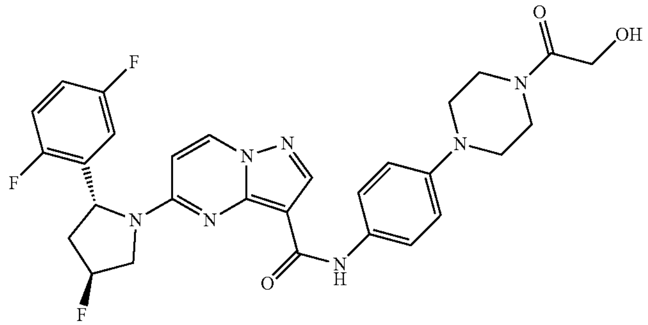 [SMILES: O=C(Nc1ccc(N2CCN(C(=O)CO)CC2)cc1)c1cnn2ccc(N3C[C@@H](F)C[C@@H]3c3cc(F)ccc3F)nc12] |
| 5 | 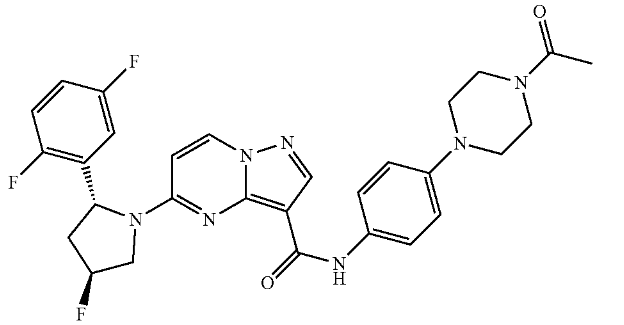 [SMILES: CC(=O)N1CCN(c2ccc(NC(=O)c3cnn4ccc(N5C[C@@H](F)C[C@@H]5c5cc(F)ccc5F)nc34)cc2)CC1] |

-continued
| Serial number | Structural formulas |
|---|---|
| 6 | 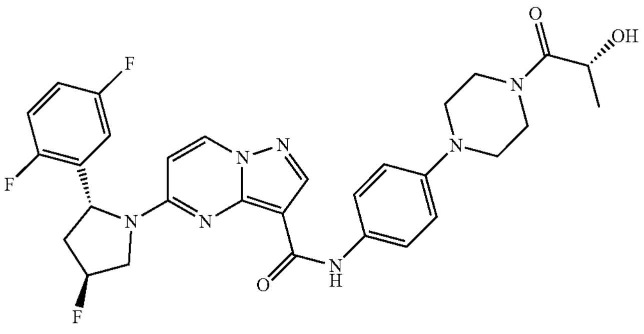 [SMILES: C[C@@H](O)C(=O)N1CCN(c2ccc(NC(=O)c3cnn4ccc(N5C[C@@H](F)C[C@@H]5c5cc(F)ccc5F)nc34)cc2)CC1] |
| 7 | 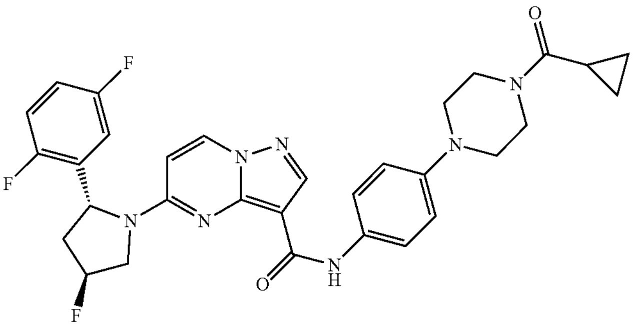 |
| 8 | 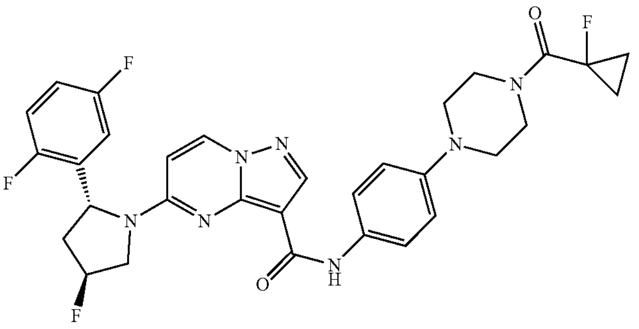 [SMILES: O=C(Nc1ccc(N2CCN(C(=O)C3(F)CC3)CC2)cc1)c1cnn2ccc(N3C[C@@H](F)C[C@@H]3c3cc(F)ccc3F)nc12] |
| 9 | 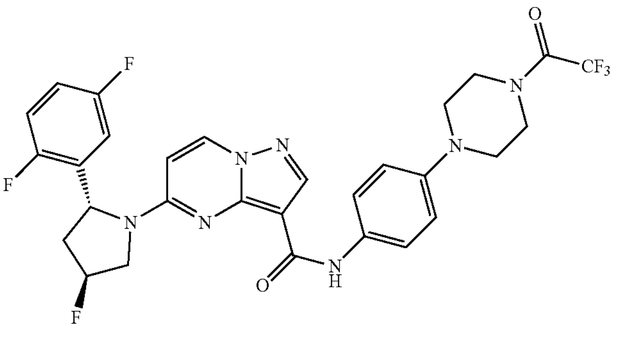 [SMILES: O=C(Nc1ccc(N2CCN(C(=O)C(F)(F)F)CC2)cc1)c1cnn2ccc(N3C[C@@H](F)C[C@@H]3c3cc(F)ccc3F)nc12] |

-continued
| Serial number | Structural formulas |
|---|---|
| 10 | 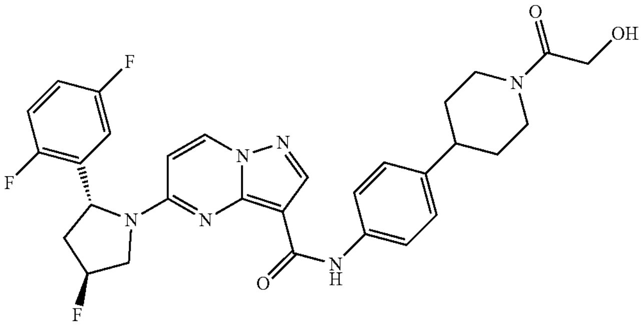 [SMILES: O=C(Nc1ccc(C2CCN(C(=O)CO)CC2)cc1)c1cnn2ccc(N3C[C@@H](F)C[C@@H]3c3cc(F)ccc3F)nc12] |
| 11 | 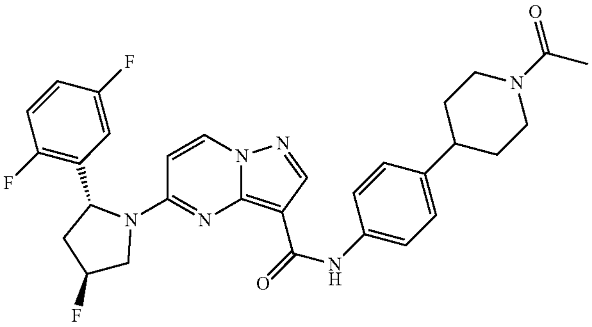 [SMILES: CC(=O)N1CCC(c2ccc(NC(=O)c3cnn4ccc(N5C[C@@H](F)C[C@@H]5c5cc(F)ccc5F)nc34)cc2)CC1] |
| 12 | 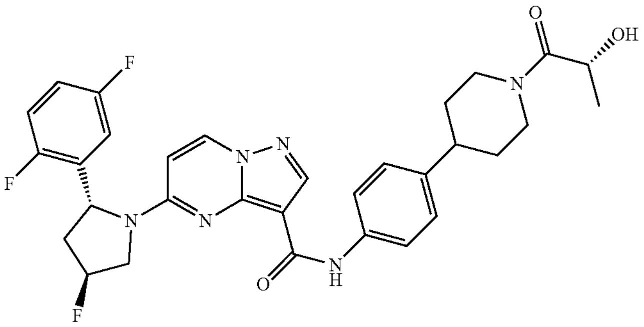 |
| 13 | 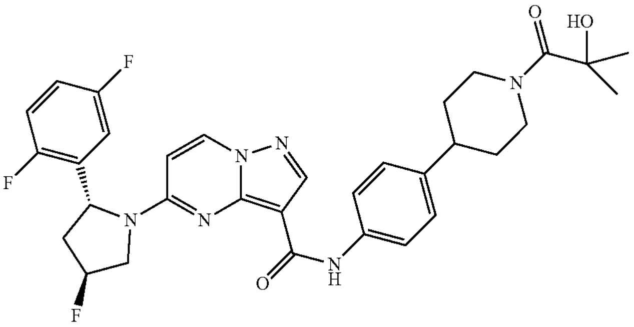 [SMILES: CC(C)(O)C(=O)N1CCC(c2ccc(NC(=O)c3cnn4ccc(N5C[C@@H](F)C[C@@H]5c5cc(F)ccc5F)nc34)cc2)CC1] |

-continued
| Serial number | Structural formulas |
| --- | --- |
| 14 | 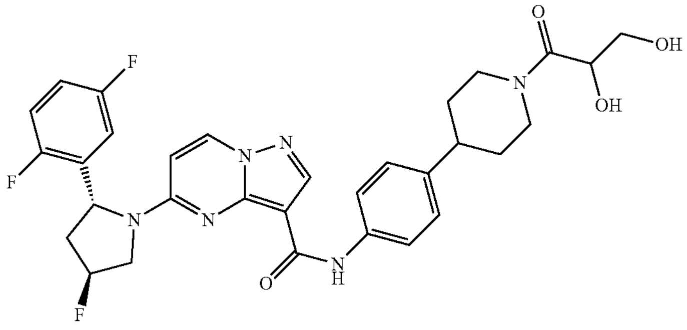 [SMILES: O=C(Nc1ccc(C2CCN(C(=O)C(O)CO)CC2)cc1)c1cnn2ccc(N3C[C@@H](F)C[C@@H]3c3cc(F)ccc3F)nc12] |
| 15 | 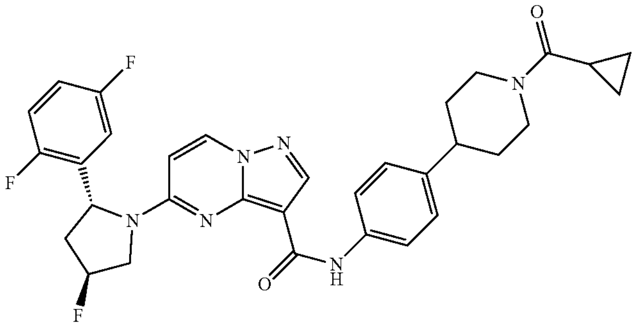 [SMILES: O=C(Nc1ccc(C2CCN(C(=O)C3CC3)CC2)cc1)c1cnn2ccc(N3C[C@@H](F)C[C@@H]3c3cc(F)ccc3F)nc12] |
| 16 | 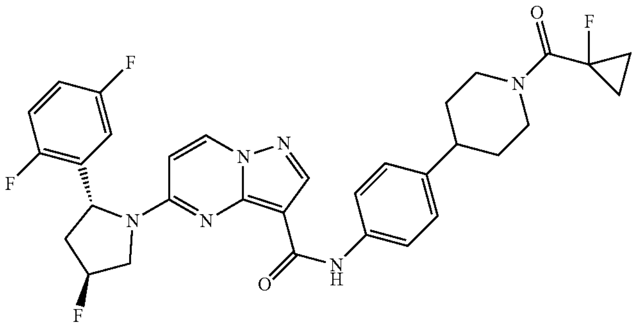 |
| 17 | 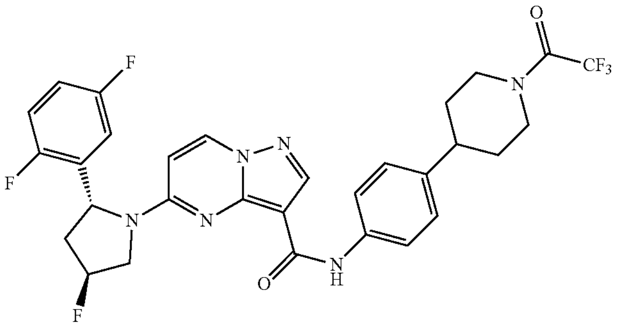 [SMILES: O=C(Nc1ccc(C2CCN(C(=O)C(F)(F)F)CC2)cc1)c1cnn2ccc(N3C[C@@H](F)C[C@@H]3c3cc(F)ccc3F)nc12] |

-continued
| Serial number | Structural formulas |
|---|---|
| 18 | 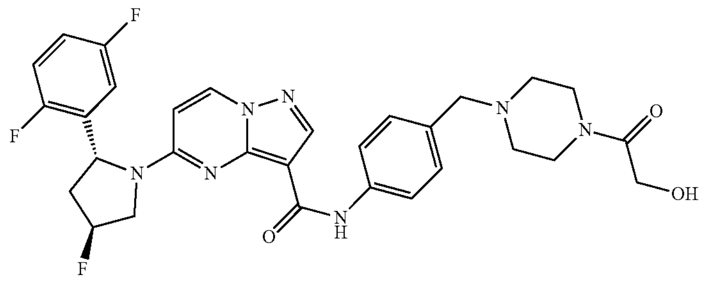 [SMILES: O=C(Nc1ccc(CN2CCN(C(=O)CO)CC2)cc1)c1cnn2ccc(N3C[C@@H](F)C[C@@H]3c3cc(F)ccc3F)nc12] |
| 19 | 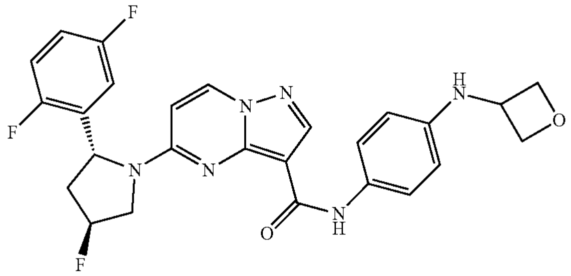 [SMILES: O=C(Nc1ccc(NC2COC2)cc1)c1cnn2ccc(N3C[C@@H](F)C[C@@H]3c3cc(F)ccc3F)nc12] |
| 20 | 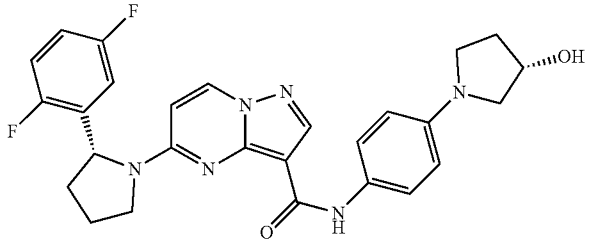 [SMILES: O=C(Nc1ccc(N2CC[C@H](O)C2)cc1)c1cnn2ccc(N3CCC[C@@H]3c3cc(F)ccc3F)nc12] |
| 21 | 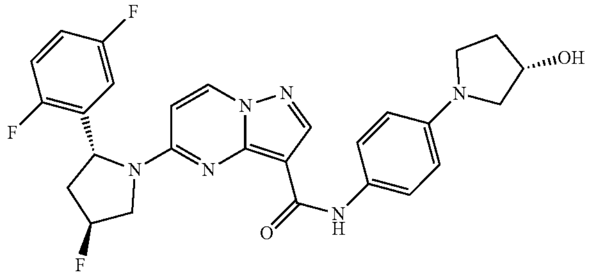 [SMILES: O=C(Nc1ccc(N2CC[C@H](O)C2)cc1)c1cnn2ccc(N3C[C@@H](F)C[C@@H]3c3cc(F)ccc3F)nc12] |
| 22 | 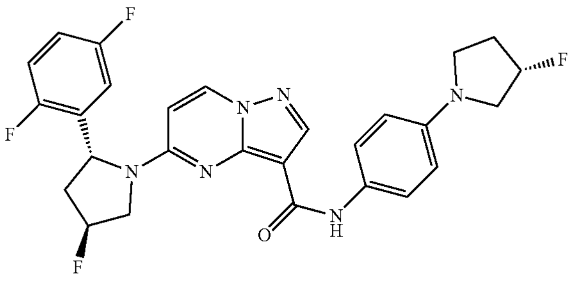 [SMILES: O=C(Nc1ccc(N2CC[C@H](F)C2)cc1)c1cnn2ccc(N3C[C@@H](F)C[C@@H]3c3cc(F)ccc3F)nc12] |

-continued
| Serial number | Structural formulas |
|---|---|
| 23 | 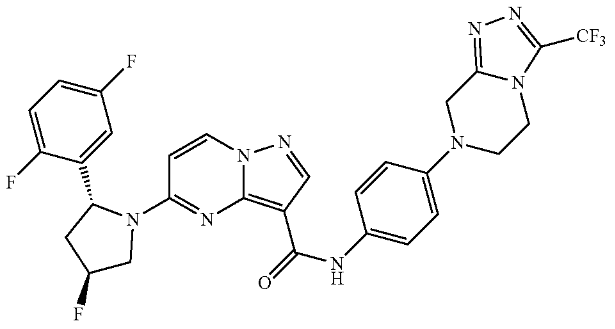 [SMILES: O=C(Nc1ccc(N2CCn3c(nnc3C(F)(F)F)C2)cc1)c1cnn2ccc(N3C[C@@H](F)C[C@@H]3c3cc(F)ccc3F)nc12] |
| 24 | 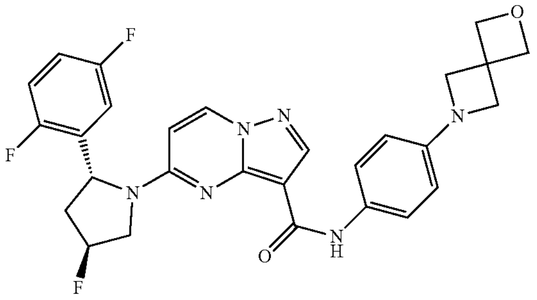 [SMILES: O=C(Nc1ccc(N2CC3(COC3)C2)cc1)c1cnn2ccc(N3C[C@@H](F)C[C@@H]3c3cc(F)ccc3F)nc12] |
| 25 | 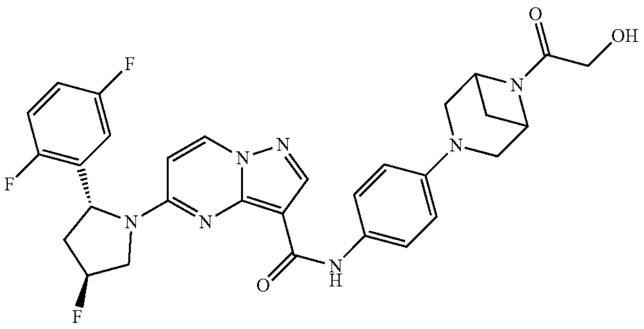 [SMILES: O=C(Nc1ccc(N2CC3CC(C2)N3C(=O)CO)cc1)c1cnn2ccc(N3C[C@@H](F)C[C@@H]3c3cc(F)ccc3F)nc12] |
| 26 | 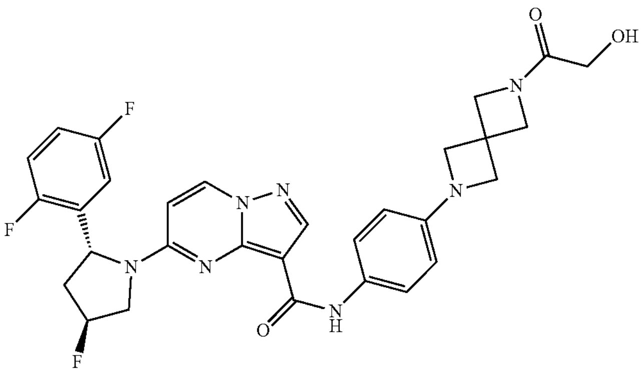 [SMILES: O=C(Nc1ccc(N2CC3(CN(C(=O)CO)C3)C2)cc1)c1cnn2ccc(N3C[C@@H](F)C[C@@H]3c3cc(F)ccc3F)nc12] |

-continued
| Serial number | Structural formulas |
|---|---|
| 27 | 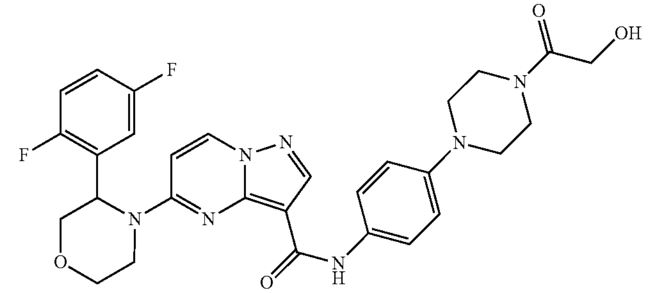 |
| 28 | 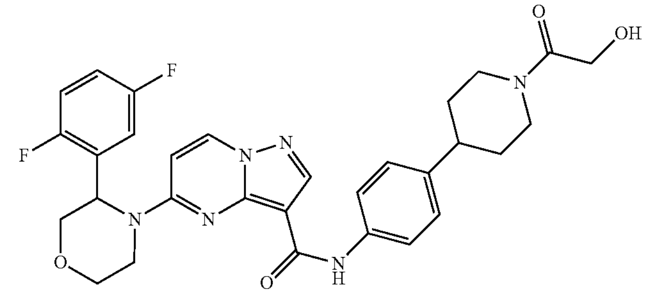 [SMILES: O=C(Nc1ccc(C2CCN(C(=O)CO)CC2)cc1)c1cnn2ccc(N3CCOCC3c3cc(F)ccc3F)nc12] |
| 29 | 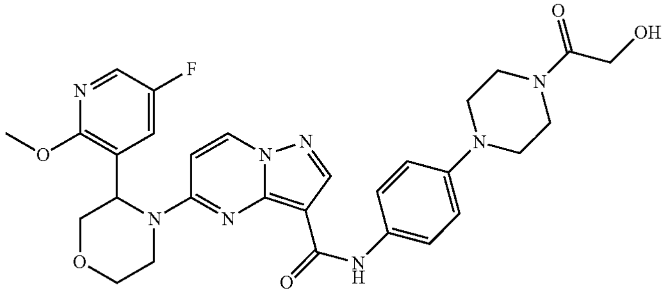 [SMILES: COc1ncc(F)cc1C1COCCN1c1ccn2ncc(C(=O)Nc3ccc(N4CCN(C(=O)CO)CC4)cc3)c2n1] |
| 30 | 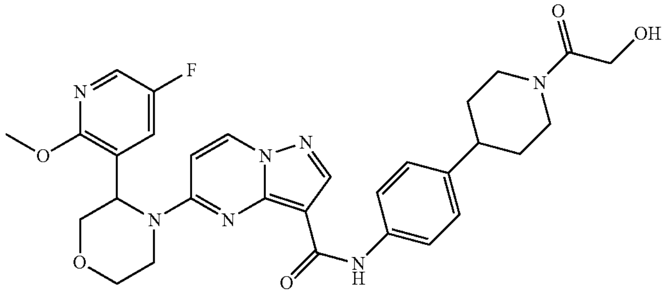 |
| 31 | 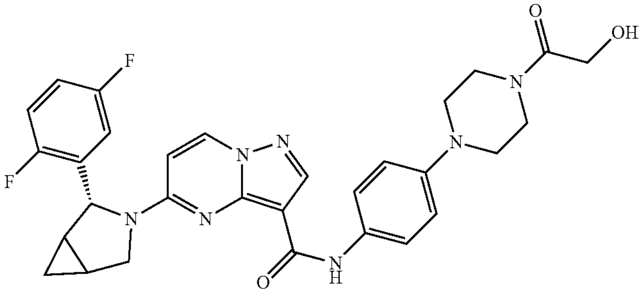 [SMILES: O=C(Nc1ccc(N2CCN(C(=O)CO)CC2)cc1)c1cnn2ccc(N3CC4CC4[C@@H]3c3cc(F)ccc3F)nc12] |

-continued
| Serial number | Structural formulas |
| --- | --- |
| 34 | 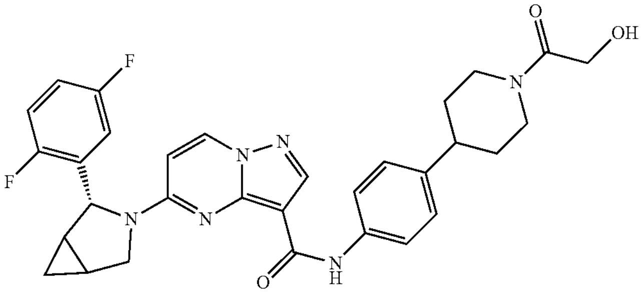 [SMILES: O=C(Nc1ccc(C2CCN(C(=O)CO)CC2)cc1)c1cnn2ccc(N3CC4CC4[C@@H]3c3cc(F)ccc3F)nc12] |
| 37 | 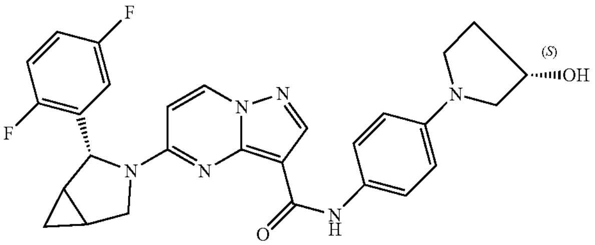 |
| 41 | 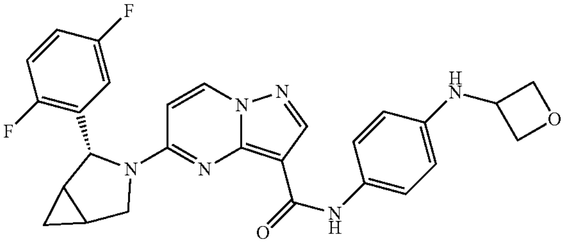 [SMILES: O=C(Nc1ccc(NC2COC2)cc1)c1cnn2ccc(N3CC4CC4[C@@H]3c3cc(F)ccc3F)nc12] |
| 44 | 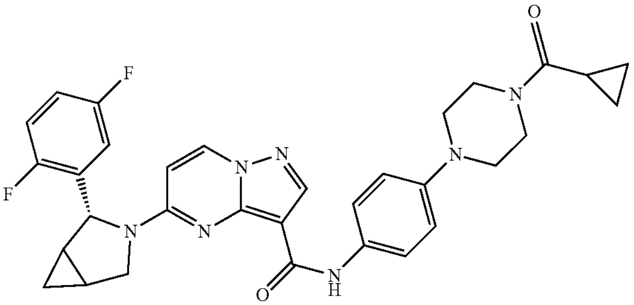 |
| 46 | 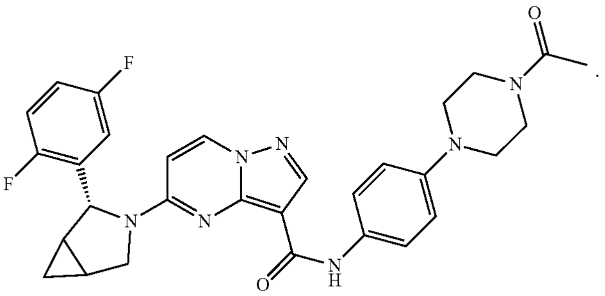 [SMILES: CC(=O)N1CCN(c2ccc(NC(=O)c3cnn4ccc(N5CC6CC6[C@@H]5c5cc(F)ccc5F)nc34)cc2)CC1] |

12. A pharmaceutical composition, comprising the compound, or the tautomer, the stereoisomer, the optical isomer, the solvate, the nitrogen oxide, the prodrug, the isotopic derivative or the pharmaceutically acceptable salt thereof according to claim 1.

13. A method for treating a disease mediated by TRK, ALK, ROS1, or a combination thereof, comprising administering to a patient the compound, or the tautomer, the stereoisomer, the optical isomer, the solvate, the nitrogen oxide, the prodrug, the isotopic derivative or the pharmaceutically acceptable salt according to claim 1.

14. The method according to claim 13, wherein the disease is a cell proliferative disease and the cell proliferative disease is a tumor.

15. The method according to claim 14, wherein, the tumor is a hematological malignancy, lung cancer, breast cancer, ovarian cancer, prostate cancer, pancreatic cancer, brain glioma, colorectal cancer, melanoma, head and neck cancer, gallbladder cancer, thyroid cancer, glioblastoma, gastric cancer, neuroblastoma, or salivary gland cancer.

16. The compound, or the tautomer, the stereoisomer, the optical isomer, the solvate, the nitrogen oxide, the prodrug, the isotopic derivative or the pharmaceutically acceptable salt thereof according to claim 1, wherein ring A is selected from:

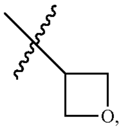 , 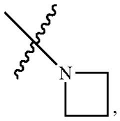 , 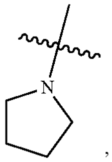 , 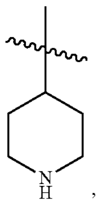 , 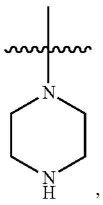 ,

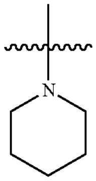 , 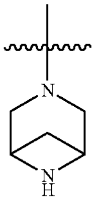 , 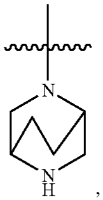 , 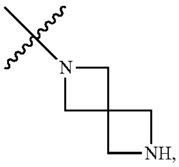

-continued

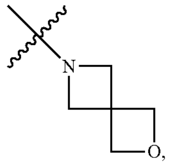 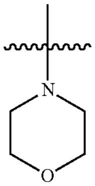 , 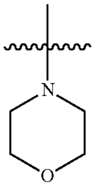 , 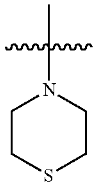 ,

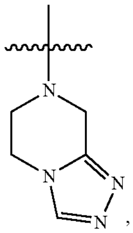 , and 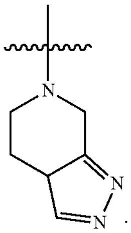 .

17. The compound, or the tautomer, the stereoisomer, the optical isomer, the solvate, the nitrogen oxide, the prodrug, the isotopic derivative or the pharmaceutically acceptable salt thereof according to claim 1, wherein $R_1$, when present, is each independently selected from: hydrogen, halogen, —OH, amino, $C_{1-6}$ alkyl and $C_{1-6}$ alkoxy.

18. The compound, or the tautomer, the stereoisomer, the optical isomer, the solvate, the nitrogen oxide, the prodrug, the isotopic derivative or the pharmaceutically acceptable salt thereof according to claim 1, wherein $R_{1a}$, when present, is each independently selected from: halogen, —OH, amino, —$NHC_{1-3}$ alkyl, —$N(C_{1-3}$ alkyl$)_2$, and cyano.

19. The compound, or the tautomer, the stereoisomer, the optical isomer, the solvate, the nitrogen oxide, the prodrug, the isotopic derivative or the pharmaceutically acceptable salt thereof according to claim 1, wherein $R_2$ is selected from H, F, —OH, and $C_{1-6}$ alkyl.

20. The compound, or the tautomer, the stereoisomer, the optical isomer, the solvate, the nitrogen oxide, the prodrug, the isotopic derivative or the pharmaceutically acceptable salt thereof according to claim 1, wherein $R_3$ is selected from: H, F, Cl, —OH, methyl, and methoxy.

* * * * *